(12) United States Patent
Omori et al.

(10) Patent No.: US 9,662,131 B2
(45) Date of Patent: May 30, 2017

(54) MANIPULATOR FOR MEDICAL USE

(75) Inventors: Shigeru Omori, Kanagawa-ken (JP); Shuichi Uenohara, Fujinomiya (JP); Makoto Jinno, Tokyo (JP)

(73) Assignee: Karl Storz GmbH & Co. KG, Tuttlingen (DE)

( * ) Notice: Subject to any disclaimer, the term of this patent is extended or adjusted under 35 U.S.C. 154(b) by 1167 days.

(21) Appl. No.: 11/939,287

(22) Filed: Nov. 13, 2007

(65) Prior Publication Data

US 2009/0112229 A1 Apr. 30, 2009

(30) Foreign Application Priority Data

Oct. 31, 2007 (JP) ................................. 2007-283313

(51) Int. Cl.
*A61B 17/29* (2006.01)
*A61B 17/00* (2006.01)
*A61B 34/00* (2016.01)

(52) U.S. Cl.
CPC .............. *A61B 17/29* (2013.01); *A61B 34/70* (2016.02); *A61B 34/71* (2016.02); *A61B 2017/0046* (2013.01); *A61B 2017/00398* (2013.01); *A61B 2017/2927* (2013.01);
(Continued)

(58) Field of Classification Search
CPC .... A61B 2019/2242; A61B 2019/2276; A61B 2017/2927; A61B 17/29; A61B 19/22; A61B 2017/2939; A61B 2017/2929; A61B 2017/2932; A61B 2917/2932; A61B 17/2909; A61B 34/71; A61B 2017/00398; A61B 2017/0046; A61B 2017/291; A61B 2017/2912; A61B 2017/2913; A61B 2017/2919; A61B 2017/2924;
(Continued)

(56) References Cited

U.S. PATENT DOCUMENTS 2,765,930 A * 10/1956 Greer et al. ........................ 414/7
4,782,833 A * 11/1988 Einhorn et al. ................. 606/80
5,649,955 A * 7/1997 Hashimoto et al. .......... 606/205
(Continued)

FOREIGN PATENT DOCUMENTS

DE 41 36 861 A1 5/1993
EP 0 677 275 A2 10/1995
(Continued)

OTHER PUBLICATIONS

Office Action mailed Sep. 19, 2011, in co-pending U.S. Appl. No. 12/261,829.
(Continued)

*Primary Examiner* — Ryan J Severson
(74) *Attorney, Agent, or Firm* — Whitmyer IP Group LLC

(57) ABSTRACT

A medical manipulator comprises a distal end working unit including a gripper as an end effector, an operating unit for operating the distal end working unit, a coupling interconnecting the distal end working unit and the operating unit, and an attitude changing mechanism for changing an attitude of the distal end working unit. When the operating unit is operated by an operator, the end effector is mechanically operated by a transmitting member. The attitude changing mechanism is operated by a bending drive source and a rotational drive source, which are operated when the operating unit is operated by the operator.

5 Claims, 57 Drawing Sheets

(52) U.S. Cl.
CPC ............... *A61B 2017/2929* (2013.01); *A61B 2017/2932* (2013.01); *A61B 2034/742* (2016.02)

(58) Field of Classification Search
CPC .... A61B 2017/2925; A61B 2017/2926; A61B 2017/293; A61B 2017/2931
USPC ........ 606/205, 167, 170, 174, 206; 433/159; 901/31, 34, 36
See application file for complete search history.

(56) References Cited

U.S. PATENT DOCUMENTS

| | | | |
|---|---|---|---|
| 5,792,165 A * | 8/1998 | Klieman | A61B 17/29 606/170 |
| 5,938,678 A * | 8/1999 | Zirps | A61B 17/29 606/167 |
| 6,077,287 A * | 6/2000 | Taylor et al. | 606/170 |
| 6,889,116 B2 * | 5/2005 | Jinno | 700/245 |
| 2003/0236549 A1 | 12/2003 | Bonadio et al. | |
| 2004/0266574 A1 | 12/2004 | Jinno et al. | |
| 2005/0090809 A1 | 4/2005 | Cooper et al. | |
| 2007/0208375 A1 | 9/2007 | Nishizawa et al. | |
| 2009/0112230 A1 | 4/2009 | Jinno | |

FOREIGN PATENT DOCUMENTS

| | | |
|---|---|---|
| EP | 1 707 153 A1 | 10/2006 |
| JP | 63-176092 U | 11/1988 |
| JP | 63-288147 | 11/1988 |
| JP | 8-33628 | 2/1996 |
| JP | 10-179601 | 7/1998 |
| JP | 2001-276091 | 10/2001 |
| JP | 2002-102248 | 4/2002 |
| JP | 2002-282257 | 10/2002 |
| JP | 2003-61969 | 3/2003 |
| JP | 2003-111765 | 4/2003 |
| JP | 3421117 | 4/2003 |
| JP | 2004-122286 | 4/2004 |
| JP | 2004-301275 | 10/2004 |
| JP | 2006-247804 | 9/2006 |

OTHER PUBLICATIONS

Office Action issued Dec. 18, 2012 in Japanese Application No. 2007-283313 (With Partial English Translation).

Japanese Office Action issued Apr. 24, 2012, in Patent Application No. 2007-283323 (with Partial English-language translation).

Office Action issued Apr. 16, 2013 in Japanese Application No. 2007-283313 (With Partial English Translation).

* cited by examiner

omitted …

MANIPULATOR FOR MEDICAL USE

BACKGROUND OF THE INVENTION

Field of the Invention

The present invention relates to a medical manipulator for use in laparoscopic surgery, for example.

Description of the Related Art

In recent years, attention has been drawn to laparoscopic surgery for removal of the appendix and gall bladder, without opening the abdominal cavity, rather than abdominal surgery. During laparoscopic surgery, it is customary to insert four trocars, for example, through the abdominal wall and into the abdominal cavity, to monitor the abdominal cavity with a small camera inserted through one of the trocars, and to manipulate forceps, scissors, an electrosurgical knife, etc., inserted through the other trocars in order to perform a surgical operation on the affected part in the abdominal cavity.

The applicant has proposed a surgical instrument (medical manipulator) for use in such laparoscopic surgery. The proposed surgical instrument comprises a long instrument body and a tip end portion, which can be rotated with respect to the long instrument body, for bringing a medical working unit on the tip end portion into a desired attitude while keeping the medical working unit close to a body region to be surgically treated. For details, reference should be made to Japanese Patent No. 3421117.

The medical manipulator is required to allow the surgeon to perform various appropriate techniques quickly depending on the position and size of the affected part, for removing, suturing, and tying-knot the affected part. According to Japanese Laid-Open Patent Publication Nos. 2002-102248 and 2004-301275, there have been proposed medical manipulators, which can be manipulated simply, with a high degree of freedom.

The medical manipulator disclosed in Japanese Patent No. 3421117, for example, allows the operator to manipulate a rotary manipulating member to directly rotate the medical working unit on the tip end portion. It has been desired that the medical manipulator be operable with greater ease, in order to perform appropriate techniques quickly depending on the position and size of the affected part.

SUMMARY OF THE INVENTION

It is a general object of the present invention to provide a medical manipulator that can be operated with greater ease.

According to an embodiment of the present invention, there is provided a medical manipulator comprising a distal end working unit including an end effector, an operating unit for operating the distal end working unit, a coupling interconnecting the distal end working unit and the operating unit, and an attitude changing mechanism for changing an attitude of the distal end working unit, wherein the end effector is mechanically operated by a transmitting member when the operating unit is operated by the operator, and wherein the attitude changing mechanism is operated by an actuator which is operated when the operating unit is operated by the operator.

With the above structure, the end effector is opened, closed, turned, and otherwise operated mechanically manually by the operator, and the attitude of the distal end working unit is changed by the actuator, which operates the attitude changing mechanism. Therefore, while the end effector can easily and reliably be operated to treat an affected region with desired gripping forces, the attitude of the end effector can quickly and easily be changed by the actuator. The operability of the medical manipulator can thus be increased. In other words, the medical manipulator can easily be operated to open, close, turn, and otherwise operate the end effector, and also to change the attitude of the distal end working unit, whereby the operability of the medical manipulator is increased.

The attitude changing mechanism may comprise a bending mechanism for bending a portion of the coupling, and a rotating mechanism for rotating the distal end working unit about an axis. The rotating mechanism is capable of rotating the distal end working unit about a bent axis when the distal end working unit is bent out of parallelism with an axis of the coupling by the bending mechanism.

If the coupling is detachably mounted on the operating unit, then the distal end working unit, depending on the type of the end effector, can be replaced on the single operating unit. Also, the coupling and the distal end working unit can be sterilized at a high temperature. The medical manipulator can thus have increased versatility and maintainability.

If the operating unit includes a handle that is angularly movable by the operator to move the transmitting member back and forth, then the operability of the medical manipulator for opening and closing the end effector is increased.

The transmitting member may include a flexible member and a cylindrical member around which the flexible member is wound. The cylindrical member around which the flexible member is wound provides a simple and lightweight structure for allowing the attitude of the attitude changing mechanism to be changed so as to not interfere with the state of the end effector.

The attitude changing mechanism may include a rotational shaft comprising a cylindrical member, and the transmitting member may include a flexible member having a portion wound around the cylindrical member, whereby the transmitting member operates the end effector through the flexible member. The flexible member that is wound around the cylindrical member provides a simple and lightweight structure for actuating the end effector through the flexible member, and for changing the attitude of the attitude changing mechanism so as not to interfere with the state of the end effector, using the cylindrical member as the rotational shaft.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Preferred embodiments of medical manipulators according to the present invention will be described in detail below with reference to the accompanying drawings.

Figure 1:
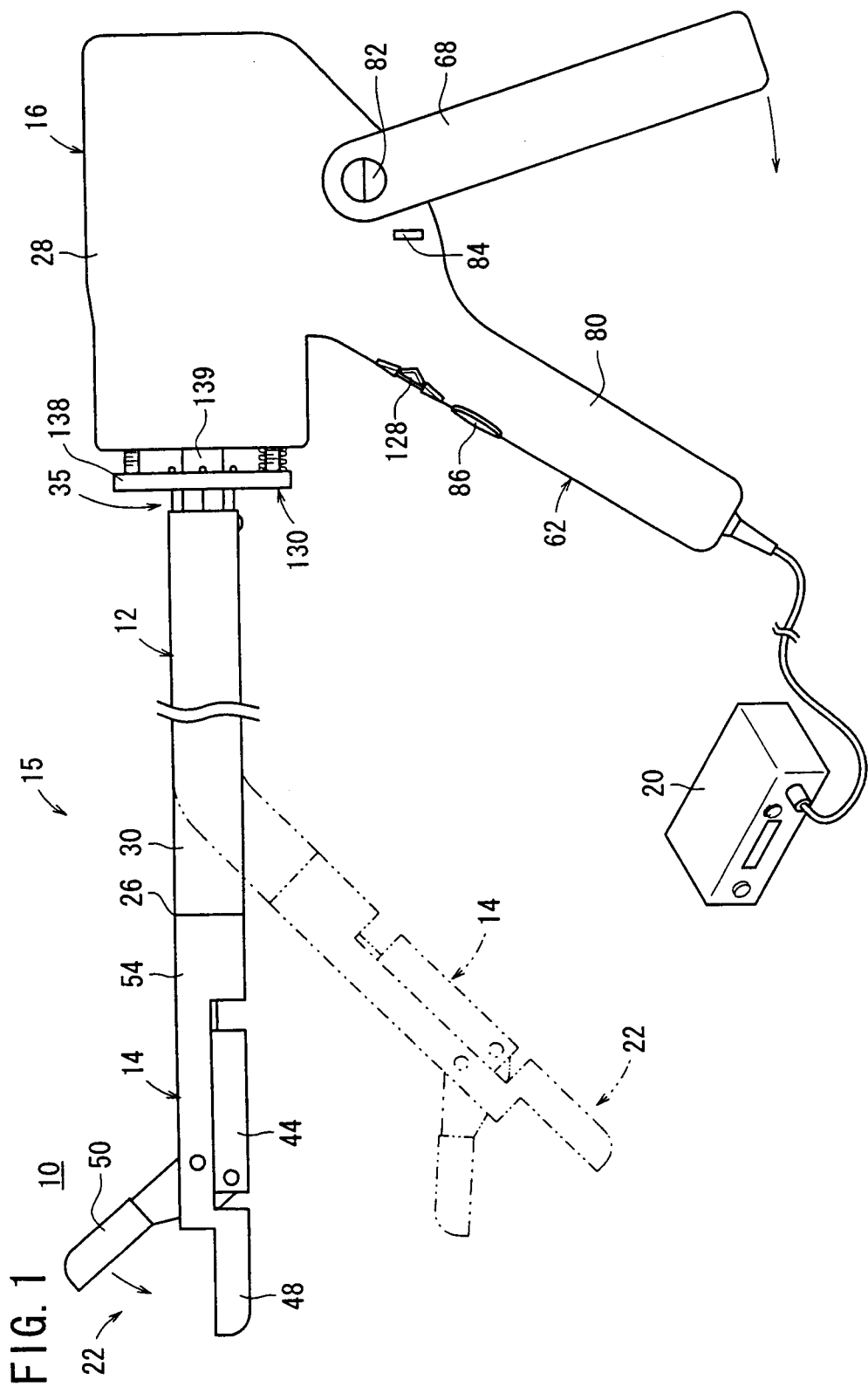
FIG. 1 is a side elevational view showing an overall structure of a medical manipulator according to an embodiment of the present invention.

FIG. 1 is a side elevational view showing an overall structure of a medical manipulator 10 according to an embodiment of the present invention. According to the present embodiment, the medical manipulator 10 will be described for use as a forceps, which is used mainly in laparoscopic surgery. However, the present invention is applicable to various surgical instruments such as pincers, and electric electrosurgical knives, for example, other than forceps. In the following description, the right hand end of the medical manipulator 10 shown in FIG. 1 will be referred to as a proximal end, and the left hand end as a distal end, as well as in the other figures.

The medical manipulator 10 comprises a distal end working unit 14 having a gripper 22 on its distal end as an end effector for performing a surgical operation on the affected part, a working unit (main manipulator body) 15 including an elongate small-diameter coupling 12 coupled to a proximal end of the distal end working unit 14, an operating unit 16 coupled to a proximal end of the coupling 12, and an elongate transmitting member 18 (see FIG. 2) extending through the coupling 12 and connecting the distal end working unit 14 and the operating unit 16 to each other. A controller 20 serving as a control unit for driving and controlling various actuators housed in the medical manipulator 10 is connected to the operating unit 16.

Figure 2:
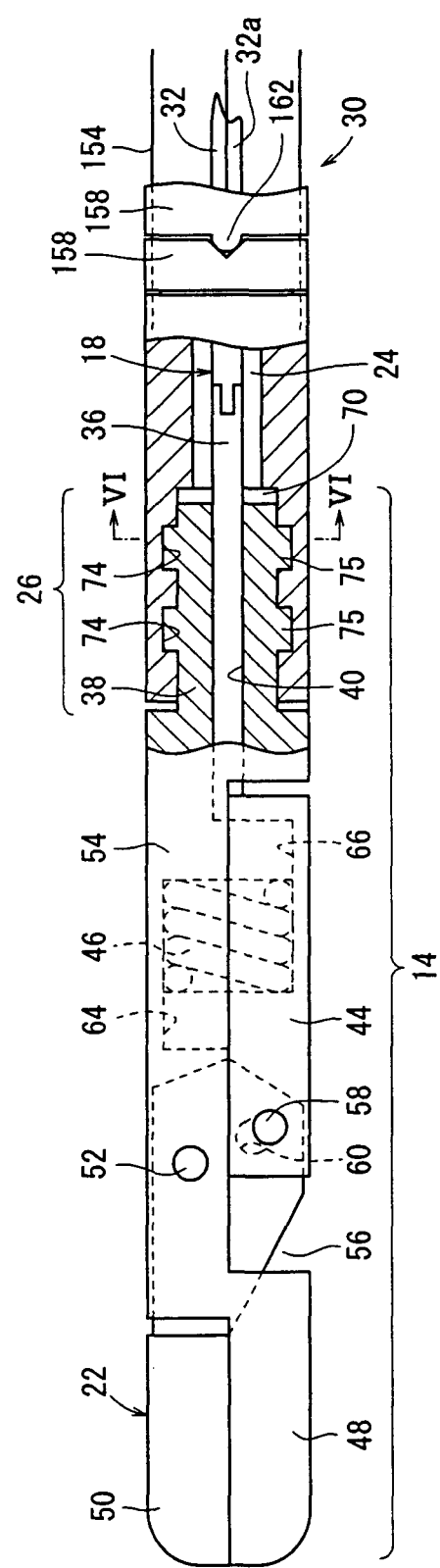
FIG. 2 is an enlarged side elevational view, partly in cross section, of a distal end portion of the medical manipulator shown in FIG. 1.
Figure 3:
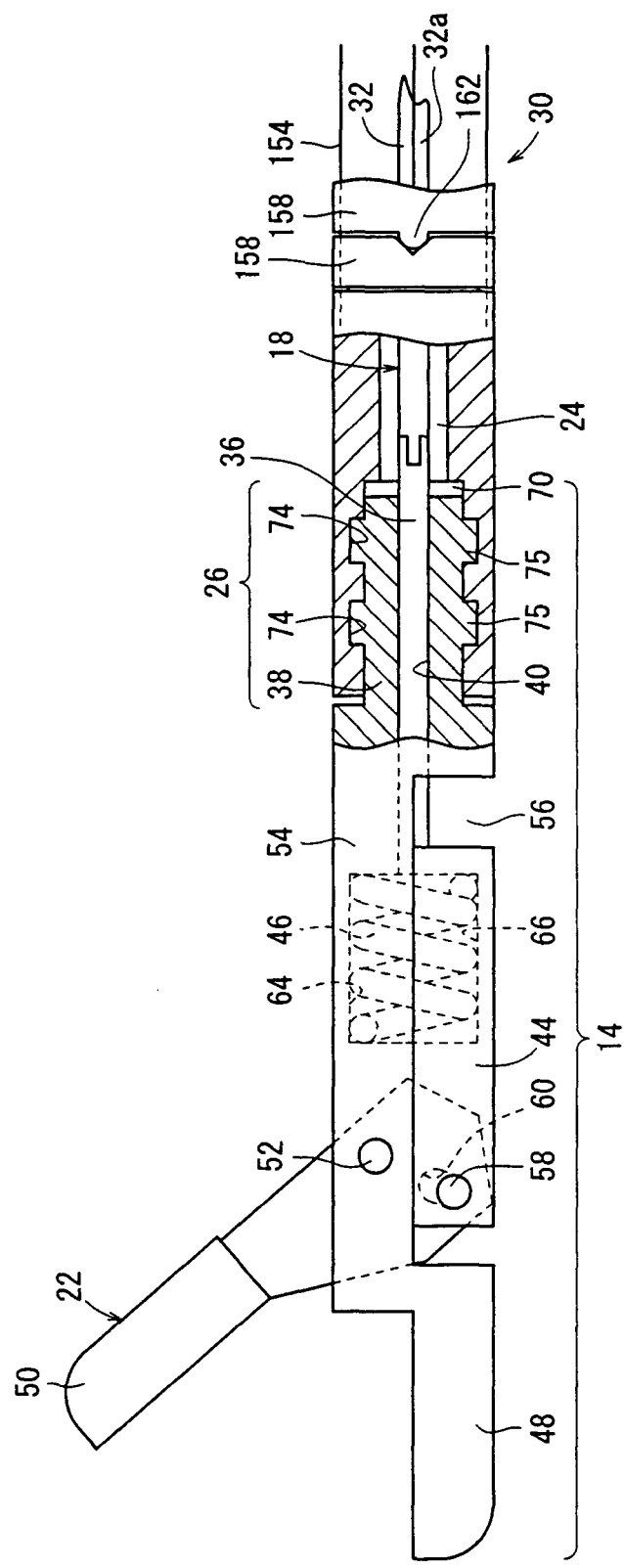
FIG. 3 is an enlarged side elevational view, partly in cross section, of the distal end portion, with a gripper being opened from the state shown in FIG. 2.
Figure 4:
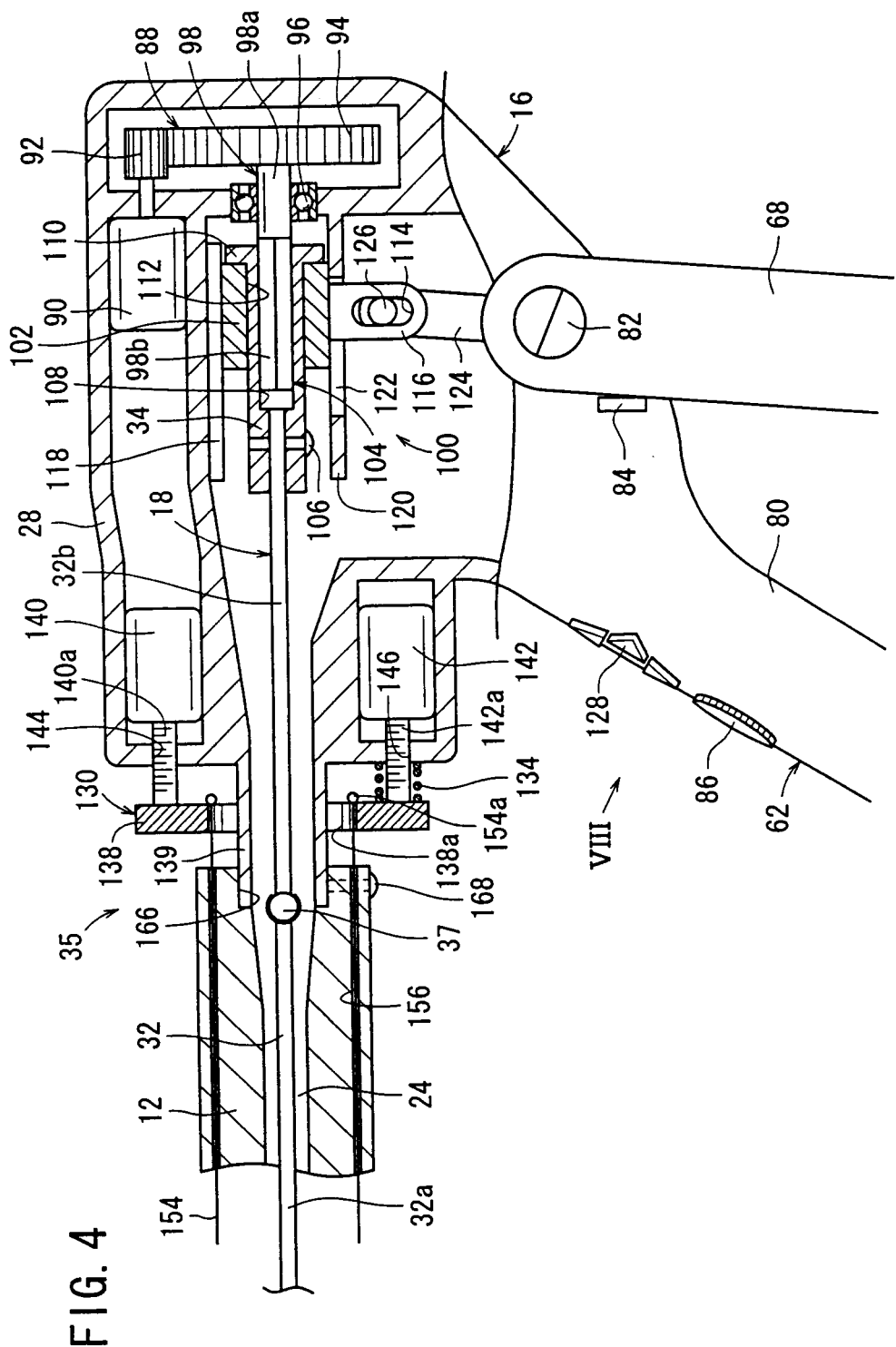
FIG. 4 is an enlarged side elevational view, partly in cross section, of an operating unit of the medical manipulator shown in FIG. 1.
Figure 5:
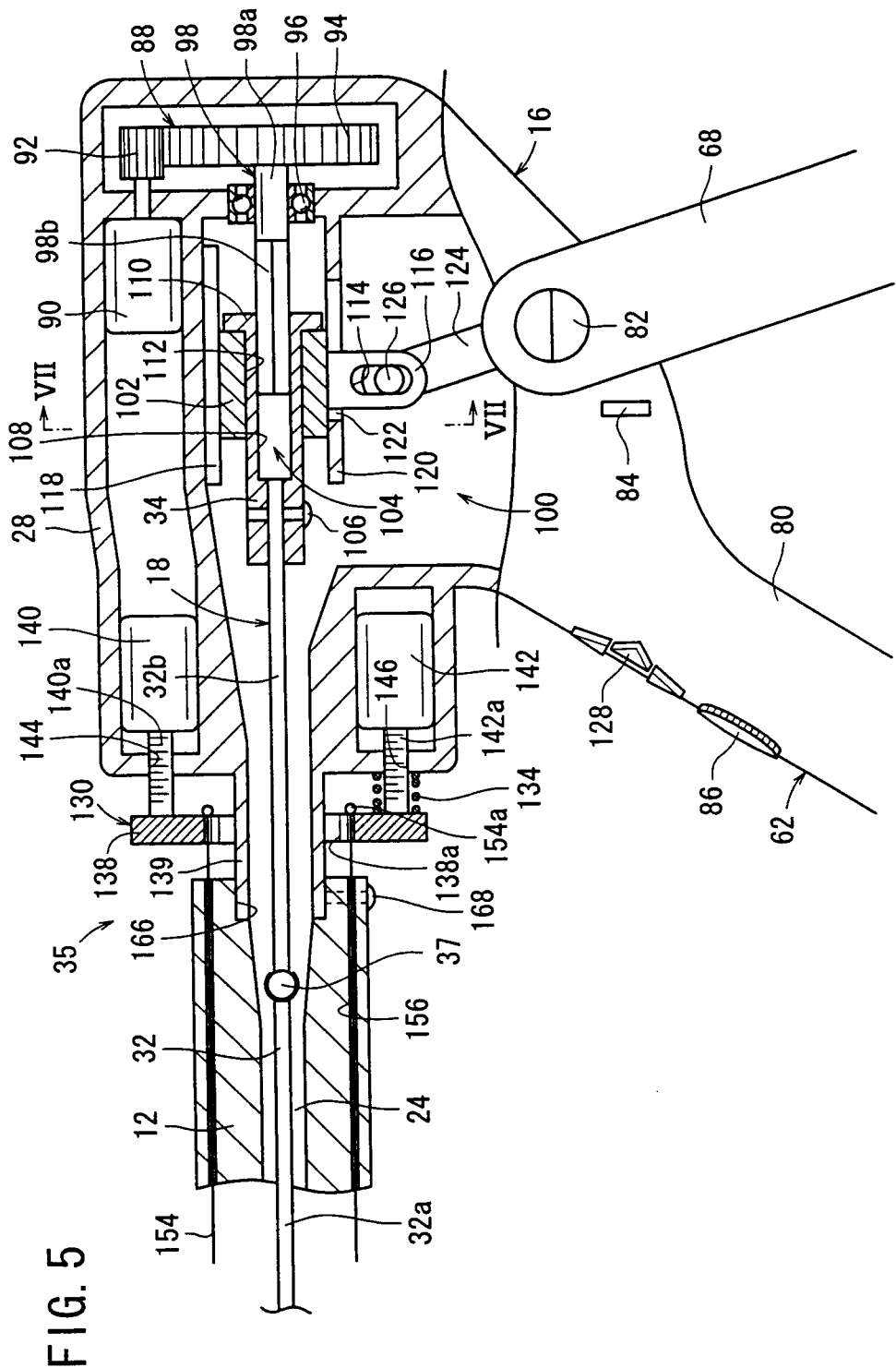
FIG. 5 is an enlarged side elevational view, partly in cross section, of the operating unit, with the gripper being opened from the state shown in FIG. 4.

FIG. 2 is an enlarged side elevational view, partly in cross section, of the distal end working unit 14 of the medical manipulator 10 shown in FIG. 1, showing a condition in which the gripper 22 on the distal end working unit 14 is closed. FIG. 3 is an enlarged side elevational view, partly in cross section, with the gripper 22 being opened from the state shown in FIG. 2. FIG. 4 is an enlarged side elevational view, partly in cross section, of the operating unit 16 of the medical manipulator shown in FIG. 1, showing a condition in which the gripper 22 on the distal end working unit 14 is closed. FIG. 5 is an enlarged side elevational view, partly in cross section, with the gripper 22 being opened from the state shown in FIG. 4.

The coupling 12 comprises a hollow elongate small-diameter member having a space 24 formed therein, which accommodates the transmitting member 18, etc. A joint (an attitude changing mechanism, a rotating mechanism) 26 rotatably coupled to the distal end working unit 14 is disposed on a distal end of the coupling 12 (see FIGS. 1 and 2). The coupling 12 has a proximal end coupled to a main operating unit body 28 of the operating unit 16 (see FIGS. 1 and 4).

Figure 6:
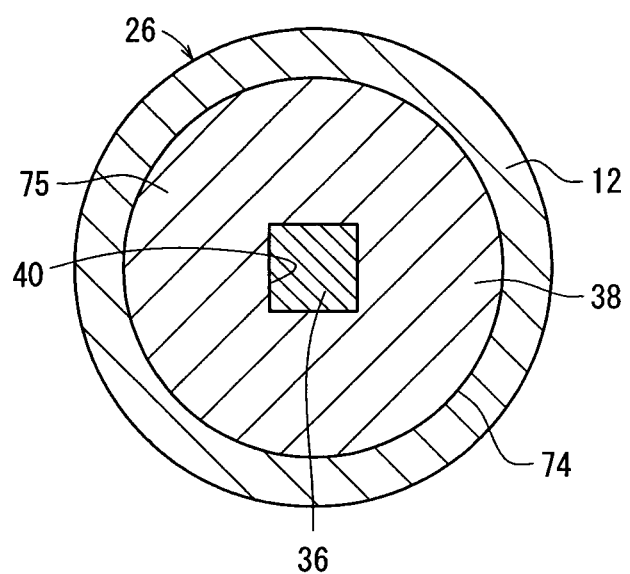
FIG. 6 is a cross-sectional view taken along line VI-VI of FIG. 2.

The coupling 12 has a transverse cross-sectional shape (a cross-sectional shape perpendicular to the axial direction thereof), which may be a circular shape, an elliptical shape, a polygonal shape, or the like, and is not limited to any particular shape. In the present embodiment, as shown in FIG. 6, the coupling 12 has a circular transverse cross-sectional shape, and has an outside diameter that enables the coupling to be inserted into a trocar (not shown), e.g., in the range of from 5 to 10 mm.

In the present embodiment, the coupling 12 has a straight shape, as shown in FIG. 1, but the coupling 12 may be curved or bent in any desired shape. The coupling 12 has at least one curvable portion (an attitude changing mechanism, a bending mechanism) 30, which can be curved (bent) to a desired shape (see FIG. 1), for increasing the range at which a living tissue can be surgically treated with the gripper 22, and for making it possible to perform a surgical treatment at a proper attitude.

Figure 12:
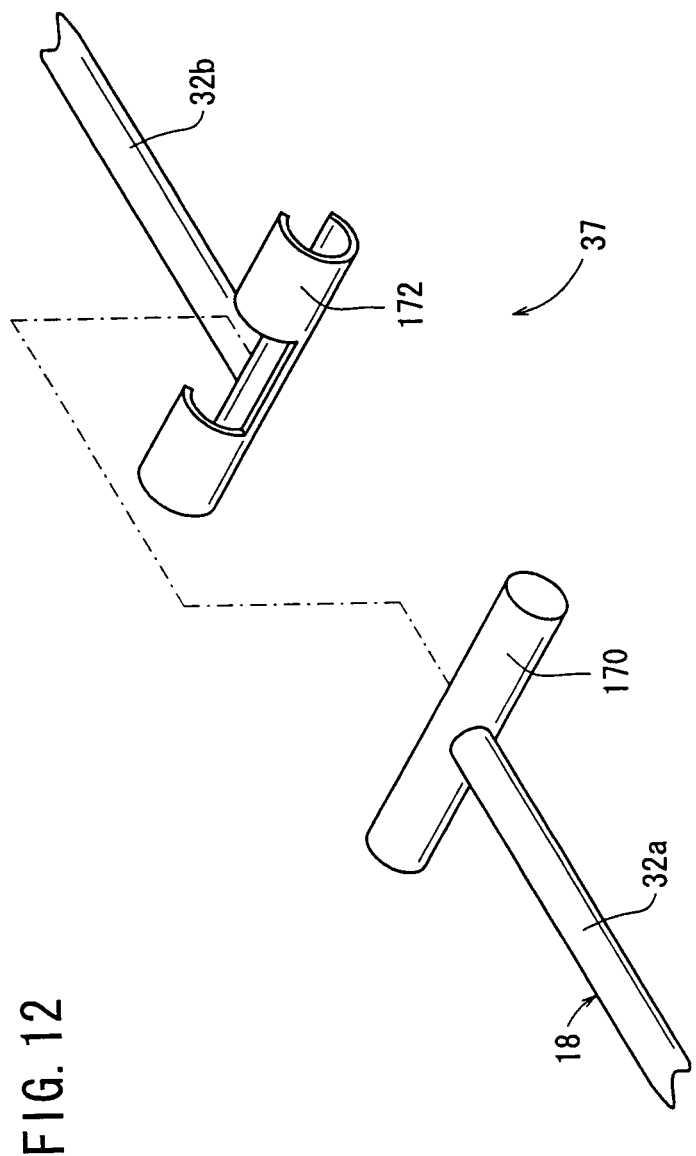
FIG. 12 is a perspective view of a linear body of a transmitting member, which is separated at a connector.

The transmitting member 18 that extends through the coupling 12 comprises a linear body 32, a first coupling member 34 coupled to a proximal end of the linear body 32, and a rod-shaped second coupling member 36 coupled to a distal end of the linear body 32. The linear body 32 has a connector 37 (see FIGS. 4 and 12) positioned near to a detachable joint 35 by which the coupling 12 and the operating unit 16 are detachably joined to each other. The connector 37 allows a distal end portion 32a and a proximal end portion 32b to be detachably joined to each other. The distal end portion 32a extends into the distal end working unit 14, and the proximal end portion 32b extends into the main operating unit body 28 (see FIGS. 2 and 4).

The linear body 32 should preferably be flexible (bendable) over its entire length or over a portion thereof, at least a portion thereof corresponding to the curvable portion 30. The linear body 32 may comprise wires such as metal wires made of stainless steel, tungsten, superelastic alloy, or the like, piano wires, ropes, chains, or the like, or fibers made of a polymeric material that can withstand relatively high tension, such as polyamide (wholly aromatic polyamide), polyester, ultrahigh molecular weight polyethylene, carbon fibers (hereinafter referred to as high-tension fibers), or a cluster of any of such wires, or other composites. The straight portion, other than the portion that corresponds to the curvable portion 30, may comprise a rigid non-flexible body. The linear body 32, in the form of a cluster of wires, should preferably be made up of one or more wires (particularly metal wires), having one or more wires of the same or different types wound (e.g., helically) around the wires, and one or more wires of the same or different types wound therearound in a direction opposite to the last-mentioned one or more wires. The linear body thus constructed is advantageous in that it is excellent in following a pulling action of the operating unit 16, while suppressing a change in length (distortion) due to twisting and bending when the linear body 32 is rotated. The outside diameter of the linear body 32 is not limited to any particular value, but may preferably be in the range of from about 1.0 to 2.5 mm, particularly in the range of from about 1.0 to 1.5 mm, according to the present embodiment.

As shown in FIGS. 2 and 6, the second coupling member 36 has a square transverse cross-sectional shape. The joint 26 includes a protrusion 38 having a passage 40 formed centrally therein. The second coupling member 36 is slidably inserted inside the passage 40. The passage 40 has a transverse cross-sectional shape that is substantially identical to the transverse cross-sectional shape of the second coupling member 36. The second coupling member 36 has a distal end portion extending into the distal end working unit 14, and which is coupled to or integrally combined with the proximal end of a slider 44, described later.

The transverse cross-sectional shape of the second coupling member 36 may be a noncircular shape, e.g., a triangular shape, a hexagonal shape, a semicircular shape, a straight-line shape, a crisscross shape, an L shape, or the like, rather than a square shape, for preventing the second coupling member 36 from rotating with respect to the passage 40. The second coupling member 36 may be made of a metal material such as aluminum, brass, stainless steel, tungsten, carbon steel, a superelastic alloy, or the like, or from a relatively hard resin such as polycarbonate, polyethylene, polypropylene, hard polyvinyl chloride, polyester, or the like, or the high-tension fibers described above.

As shown in FIGS. 2 and 3, the distal end working unit 14 includes a gripper 22 as an end effector for treating the affected part, and a coil spring 46 for biasing the slider 44 to move in one direction (toward the distal end). The gripper 22 serves as a forceps mechanism for gripping a living tissue, and includes a pair of openable/closable members, one of which is movable, i.e., a fixed pinching member 48 and a movable pinching member 50 that is angularly movable with respect to the fixed pinching member 48. The movable pinching member 50 has a proximal end angularly movably mounted on a main distal end body 54 by a pin 52. Although the gripper 22 has only one of its pinching members openable in the present embodiment, both of the pinching members thereof may be openable.

The main distal end body 54 has a recess 56 formed in a lower portion thereof (i.e., the lower portion as shown in FIG. 2). The slider 44 is disposed in the recess 56 so as to be slidable in the longitudinal direction of the distal end working unit 14. The slider 44 has a pin 58 projecting on a distal end thereof, which is inserted in an oblong hole 60 that is formed in a lower portion of the proximal end of the movable pinching member 50.

When a handle unit 62, described later, is operated to pull the transmitting member 18 toward the proximal end so as to position the slider 44 in the proximal end portion of the recess 56, the fixed pinching member 48 and the movable pinching member 50 are in a closed position (see FIG. 2). When the gripping force on the handle unit 62 is reduced or removed, the transmitting member 18 is moved toward the distal end, thereby moving the slider 44 toward the distal end of the recess 56. The pin 58 presses an inner peripheral surface of the oblong hole 60, turning and opening the movable pinching member 50 about the pin 52 (see FIG. 3). The oblong hole 60 may be dispensed with, and as the slider 44 moves, the slider 44 may be distorted to absorb the vertical movement in FIG. 2 of the pin 58.

The coil spring 46 is housed in a compressed state within a recess 64 formed in the main distal end body 54 and a recess 66 formed in the slider 44. The coil spring 46 comprises a biasing means for biasing the slider 44 toward the distal end under a resilient force thereof, i.e., for biasing the movable pinching member 50 in an opening direction. Since the medical manipulator 10 according to the present embodiment includes the coil spring 46 as the biasing means in the distal end working unit 14, it is unnecessary to provide a leaf spring or the like inside the handle unit 62 for biasing a movable handle 68 in an opening direction, for example. Thus, the operating unit 16 is simple in structure for enabling better operability.

As shown in FIGS. 2 and 3, the joint 26 includes a recess 70 having a circular transverse cross-sectional shape, which communicates with the space 24 in the coupling 12 and which is open at the distal end face of the coupling 12. The protrusion 38 has a circular transverse cross-sectional shape, which projects from the proximal end of the main distal end body 54 and is inserted into the recess 70.

The protrusion 38 includes the passage 40 formed axially centrally therein and having a transverse cross-sectional shape, which is substantially identical to the transverse cross-sectional shape of the second coupling member 36. When the second coupling member 36 is inserted in the passage 40, the rotational force of the transmitting member 18 can be transmitted to the protrusion 38 and the main distal end body 54.

Two ring-shaped grooves 74, which are axially spaced from each other by a predetermined distance, are formed in the inner circumferential surface of the recess 70. The protrusion 38 has two ring-shaped lands 75 extending circumferentially at respective positions corresponding to the grooves 74. The lands 75 are inserted respectively into the grooves 74. The lands 75 are not limited to having continuous ring shapes, but may be disposed intermittently in the circumferential direction.

The joint 26 of the above structure allows the distal end working unit 14 to rotate (roll) with respect to the coupling 12, but makes the distal end working unit 14 unable to move axially. Therefore, the joint 26 is reliably capable of preventing the distal end working unit 14 from becoming dislodged or experiencing wobbling. The joint 26 may have a rotational resistance reducing means (not shown) for reducing the rotational resistance of the distal end working unit 14. According to a specific example, the rotational resistance reducing means may comprise a lubricant, such as lubricating oil or a layer of a low-friction material such as polytetrafluoroethylene, silicone, polyethylene, polyacetal, or the like, interposed between the recess 70 and the protrusion 38. The rotational resistance reducing means allows the distal end working unit 14 to rotate more smoothly.

As shown in FIGS. 1, 4, and 5, the operating unit 16 is mounted on the proximal end of the coupling 12 for remotely opening and closing (turning) the gripper 22, bending the distal end working unit 14 in the curvable portion 30, and rotating the distal end working unit 14 with respect to the coupling 12.

The operating unit 16 includes the handle unit 62, which comprises a fixed handle 80 fixed to or integrally combined with the main operating unit body 28, and a movable handle 68 which can be opened and closed (turned) with respect to the fixed handle 80. The movable handle 68 has an upper end thereof angularly movably mounted on the main operating unit body 28 by a shaft member 82.

Figure 13:
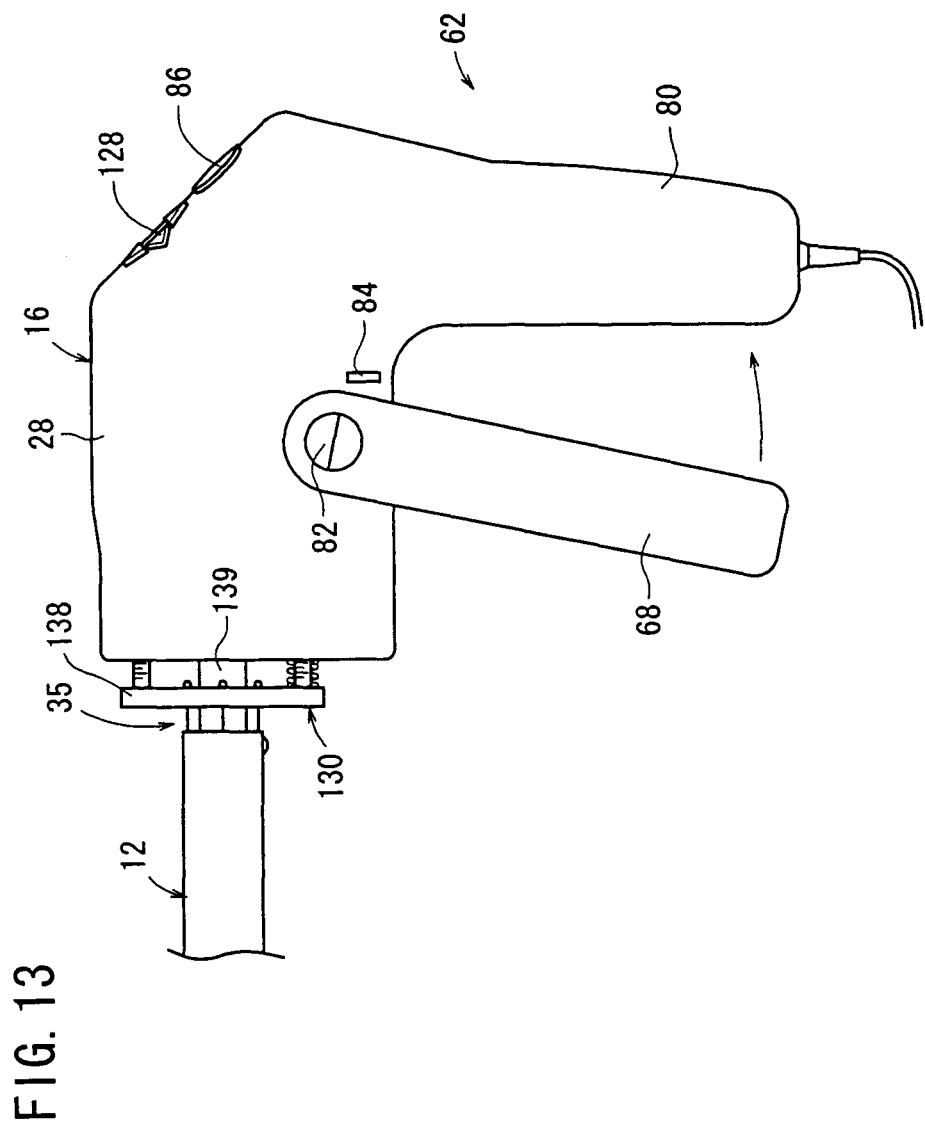
FIG. 13 is a side elevational view showing another structural example of the medical manipulator shown in FIG. 1.

A stopper 84 projects from the outer surface of a lower portion of the main operating unit body 28, for engaging the movable handle 68 so as to limit an angularly movable range thereof, for thereby preventing the transmitting member 18 from being broken when an excessive gripping force is applied to the handle unit 62. As shown in FIG. 13, the fixed handle 80 and the movable handle 68 may be switched in position. According to such a modification, a rotating action input unit 86 and a bending action input unit 128, to be described later, may be placed on an upper portion of the proximal end of the main operating unit body 28, for enabling better operability.

Figure 8:
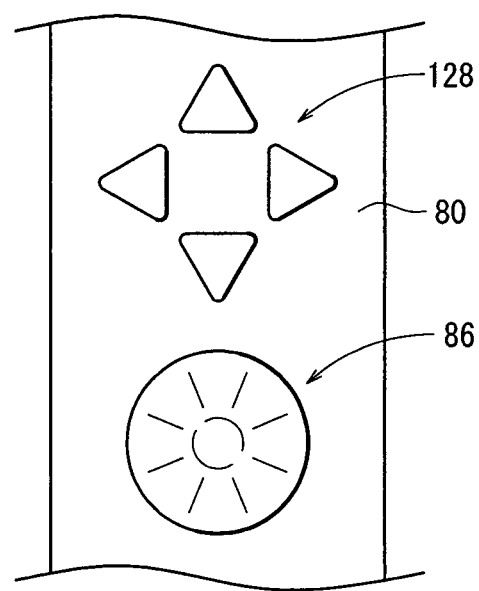
FIG. 8 is a front elevational view, partially omitted from illustration, as viewed in the direction indicated by the arrow VIII in FIG. 4.

The operating unit 16 has a rotating action mechanism 88 disposed in the proximal end of the main operating unit body 28, which can be actuated by operation of a disk-shaped rotating action input unit 86 (see FIG. 8) mounted on the fixed handle 80.

The rotating action mechanism 88 comprises a rotational drive source (actuator) 90 such as a motor, for example, a small-diameter drive gear 92 coupled to the rotational shaft of the rotational drive source 90, a large-diameter driven gear 94 held in mesh with the drive gear 92, and a bearing 96 by which the driven gear 94 is rotatably supported on the proximal end of the main operating unit body 28. The rotational drive source 90 is energized under the control of the controller 20, based on operation of the rotating action input unit 86. The driven gear 94 has a rotational shaft 98, comprising a cylindrical portion 98a on its proximal end portion and a prismatic portion 98b on its distal end portion. The cylindrical portion 98a is supported by the bearing 96.

The main operating unit body 28 houses therein a converting means 100 for converting angular movement of the movable handle 68 into longitudinal movement of the transmitting member 18, and transmitting a rotational force produced by rotation of the driven gear 94 to the transmitting member 18. The converting means 100 comprises a support member 102 by which the first coupling member 34 is rotatably supported, and a rotational force transmitting mechanism 104 for transmitting rotational force from the driven gear 94 to the first coupling member 34.

Figure 7:
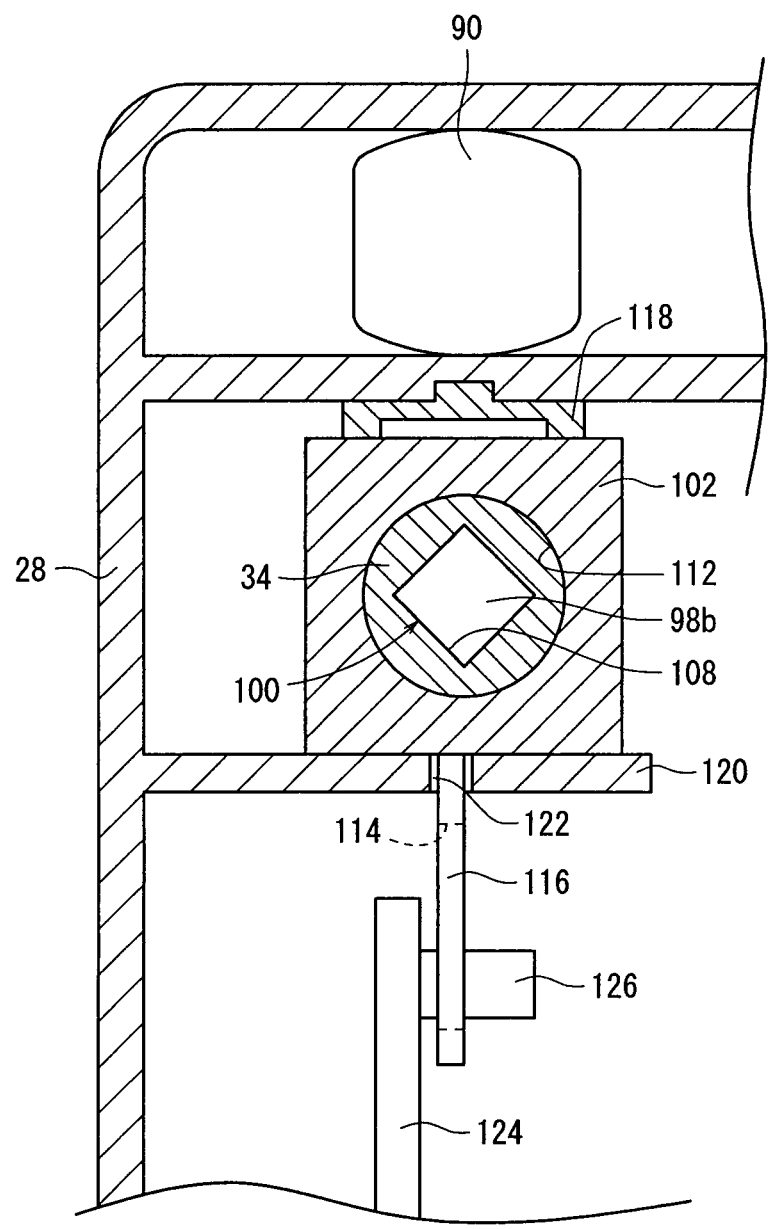
FIG. 7 is a cross-sectional view taken along line VII-VII of FIG. 5.

The proximal end portion 32b of the linear body 32 is fixed to the distal end portion of the first coupling member 34 by a pin 106. The first coupling member 34 comprises a hollow cylindrical member having a passage 108 with a square transverse cross-sectional shape formed centrally therein (see FIG. 7), in which the prismatic portion 98b of the rotational shaft 98 of the driven gear 94 is inserted. The first coupling member 34 includes a flange 110 on a proximal end thereof, which engages with the proximal end face of the support member 102.

The support member 102 has a through hole 112 with a circular transverse cross-sectional shape formed therein, in which the first coupling member 34 is inserted. A tongue 116 with an oblong hole 114 formed therein projects from a lower portion of the support member 102. The support member 102 is supported by guide members 118, 120 disposed in the main operating unit body 28, for enabling sliding movement in the longitudinal direction of the transmitting member 18. The tongue 116 projects downwardly through a slit 122 formed in the lower guide member 120.

The movable handle 68 has a projecting member 124 on an upper portion thereof, which is inserted into the main operating unit body 28. A pin 126 mounted on the upper end of the projecting member 124 is inserted into the oblong hole 114 of the tongue 116 (see FIGS. 4 and 7).

The rotational force transmitting mechanism 104 is made up of the prismatic portion 98b of the rotational shaft 98 of the driven gear 94, together with the passage 108 into which the prismatic portion 98b is inserted. The prismatic portion 98b is axially movable with respect to the passage 108, but cannot be rotated with respect to the passage 108 regardless of the depth at which the prismatic portion 98b is inserted into the passage 108. Therefore, the rotational force of the driven gear 94 is transmitted through the prismatic portion 98b and the passage 108 to the first coupling member 34, thereby rotating the transmitting member 18 in its entirety.

The transverse cross-sectional shape of the prismatic portion 98b may be a noncircular shape, e.g., a triangular shape, a hexagonal shape, a semicircular shape, a straight-line shape, a crisscross shape, an L shape, or the like, rather than a square shape, for preventing the prismatic portion 98b from rotating with respect to the passage 108. The rotational force transmitting mechanism 104 comprises a mechanism for mechanically transmitting rotational force from the rotational drive source 90 to the transmitting member 18. The rotational force transmitting mechanism 104 may be actuated by a wire, a chain, a timing belt, a link, a rod, a gear, or the like. Preferably, the rotational force transmitting mechanism 104 is actuated by a mechanical component in the form of a solid body that is nonelastic in the power transmitting direction. Although a wire, a chain, or the like, is slightly elongatable inevitably under tension, it is still regarded as a mechanical component in the form of a nonelastic solid body. The actuating mechanisms may be used to allow the rotating action mechanism 88 and the distal end working unit 14 to rotate in opposite directions, or at different speeds.

The operating unit 16 has a bending action mechanism 130 disposed on the distal end of the main operating unit body 28, which can be actuated by operation of the bending action input unit 128 for bending the curvable portion 30. The bending action input unit 128 is mounted on the fixed handle 80 and comprises four triangular buttons pointing in upper, lower (front, rear), left, and right directions.

Figure 9:
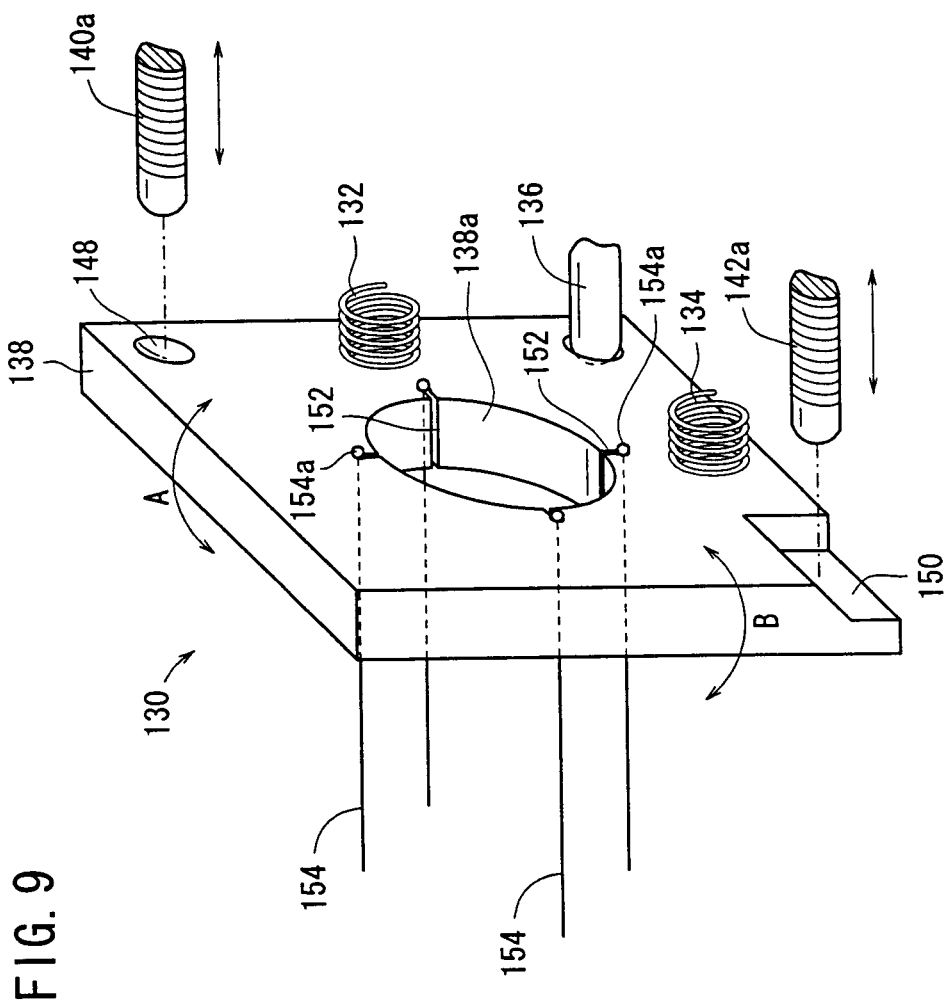
FIG. 9 is an exploded perspective view showing a structural example of a bending mechanism for bending a curvable portion of a coupling.

As shown in FIGS. 4, 5, and 9, the bending action mechanism 130 comprises two coil springs 132, 134 projecting from the distal end face of the main operating unit body 28, a pivotal shaft (bearing ball) 136 disposed parallel to the coil springs 132, 134, and a tilt plate (swing plate) 138 coupled to distal ends of the coil springs 132, 134, and spaced a predetermined distance from the distal end face of the main operating unit body 28, in confronting relation thereto. The tilt plate 138 has a hole 138a formed centrally therein, through which there is inserted a protrusion 139 having a substantially hollow cylindrical shape that projects on the distal end of the main operating unit body 28, and which is coupled to the coupling 12.

The bending action mechanism 130 also includes two bending drive sources (actuators) 140, 142 disposed in the main operating unit body 28, comprising geared motors, for example. The bending drive sources 140, 142 have respective drive shafts with respective axially movable screws 140a, 142a coupled thereto. The axially movable screws 140a, 142a are threaded respectively into threaded holes 144, 146 formed in the distal end of the main operating unit body 28, and have distal ends held respectively in abutment against two respective bearing surfaces 148, 150 on diagonally opposite corners of the tilt plate 138.

The bending action mechanism 130 operates as follows: When the bending drive sources 140, 142 are energized under the control of the controller 20, the axially movable screws 140a, 142a are moved axially so as to tilt the tilt plate 138 through a desired angle in desired directions (the directions indicated by the arrows A, B in FIG. 9) about the spherical distal end surface of the pivotal shaft 136, while being resiliently supported by the coil springs 132, 134. Since one of the bearing surfaces 150 is horizontally elongate, even when the tilt plate 138 is in a tilted state, the axially movable screw 142a is reliably held against the bearing surface 150 and the tilt plate 138 can swing smoothly while the other axially movable screw 140a is held against the bearing surface 148. The tilt plate 138 of the bending action mechanism 130 may be tilted using a mechanism that includes a general structure for swinging an optical mirror.

The hole 138a of the tilt plate 138 includes four slits 152 formed in upper, lower, left, and right directions thereof, as shown. Wires 154 are inserted from the inner circumferential portion of the hole 138a into the respective slits 152. The wires 154 have larger-diameter portions 154a on respective proximal ends thereof, which engage the proximal end face of the tilt plate 138. The wires 154 extend through four respective through holes 156 formed axially in the coupling 12, and extend to the curvable portion 30.

Figure 10:
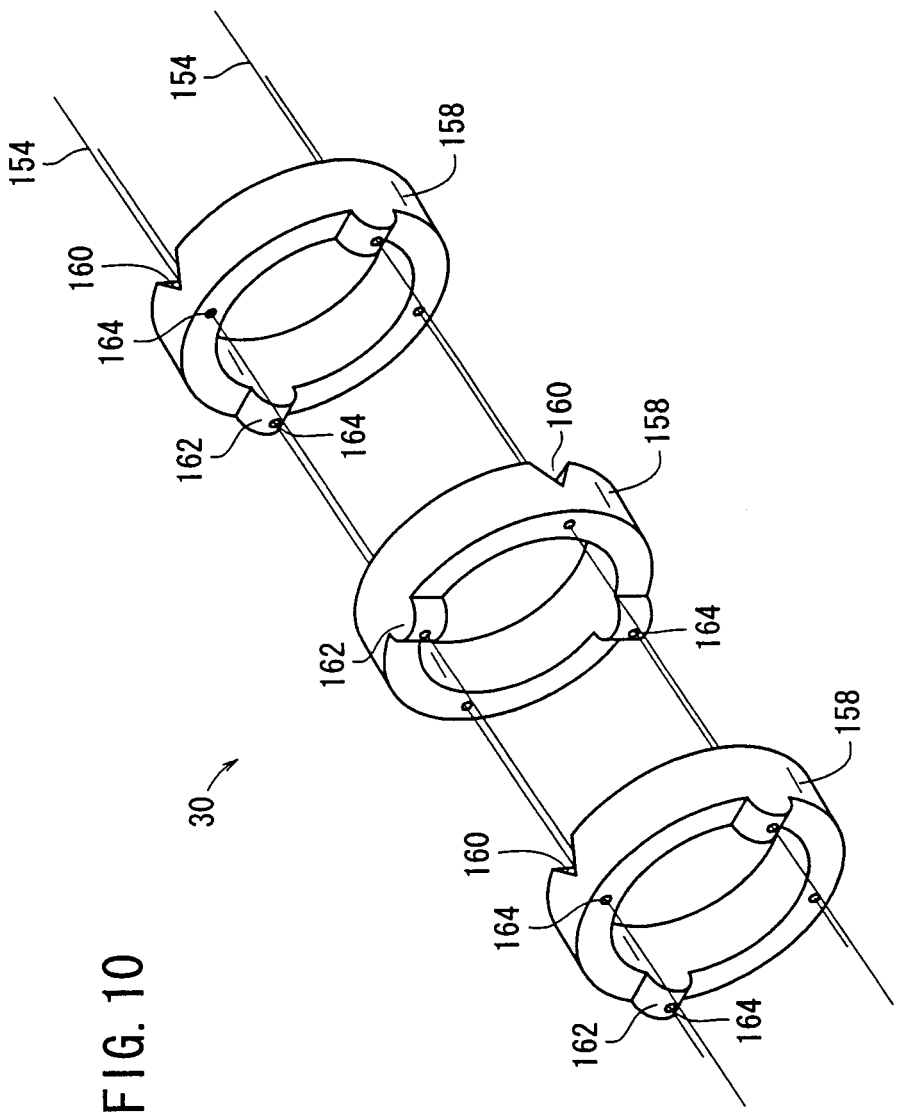
FIG. 10 is an exploded perspective view showing a portion of a structural example of the curvable portion of the coupling.

FIG. 10 is an exploded perspective view showing a portion of a structural example of the curvable portion 30 of the coupling 12. The curvable portion 30 comprises a plurality of nodal rings 158, which are joined together and angularly movable with respect to each other. In FIG. 10, the curvable portion 30 will be described as comprising three nodal rings 158, for example. However, the curvable portion 30 is not limited to being made up of three nodal rings 158, but may comprise four through thirty nodal rings 158.

Each of the nodal rings 158 includes a pair of V-shaped slots 160 formed in one of the surfaces, in diametrically opposite relation to each other across the center of the nodal ring 158, and a pair of semicylindrical ridges 162 disposed on the other surface, in diametrically opposite relation to each other across the center of the nodal ring 158. The semicylindrical ridges 162 are angularly displaced by 90° from the slots 160. Two adjacent nodal rings 158 are oriented such that the slots 160 thereof are angularly displaced from each other by 90°. The nodal rings 158 are joined such that the ridges 162 of one of the nodal rings 158 are inserted into corresponding slots 160 of the other nodal ring 158.

Each of the nodal rings 158 has through holes 164 formed therein at the slots 160 and the ridges 162. The four wires 154, whose larger-diameter portions 154a engage with the tilt plate 138, are inserted through the corresponding through holes 164 of the nodal rings 158. The wires 154 have respective distal ends coupled to the nodal ring 158 disposed in the distal end of the curvable portion 30 (see FIGS. 2 and 3). In this manner, the nodal rings 158 are placed together and combined substantially integrally with one another.

When the ridges 162 are inserted into the slots 160, a gap is created between two adjacent nodal rings 158, thereby allowing the ridges 162 to move angularly within the slots 160 and further allowing the adjacent nodal rings 158 to move angularly with respect to each other. Although the angle through which the adjacent pair of nodal rings 158 is angularly movable is small, the sum of the angles of a plurality of adjacent pairs of nodal rings 158 is large enough so as to allow the entire curvable portion 30 to be curved through a desired angle (e.g., in a range of from 60 to 120°), thus making it possible to bend the distal end working unit 14 (gripper 22) such that it is not parallel to the longitudinal axis of the coupling 12.

When the bending action input unit 128 is operated, the bending action mechanism 130 is actuated under the control of the controller 20 to tilt the tilt plate 138 through a desired angle, and to axially move the wires 154 respective distances for thereby bending the curvable portion 30 upwardly, downwardly (forwardly, rearwardly), leftwardly, and rightwardly through desired angles on the transverse cross-sectional plane of the coupling 12. Specifically, the curvable portion 30 is actively bent or curved when pulled by the tilt plate 138 through the wires 154. The directions in which the curvable portion 30 is curved, and the number of such directions (the degree of freedom), are not limited to any particular values. Although not shown, the outer circumferential surface of each nodal ring 158 may be covered with a layer made up of an elastic or a flexible material.

The curvable portion 30 is not limited to having the illustrated structure, but may comprise a bellows tube or a flexible tube. The coupling 12 may comprise a hard pipe serving as the distal end portion together with a hard pipe serving as the proximal end portion, wherein the hard pipes are angularly movably connected by a single shaft or a plurality of shafts for bending the curvable portion 30. Alternatively, the curvable portion 30 may comprise a bending mechanism having a pivot shaft.

Figure 11:
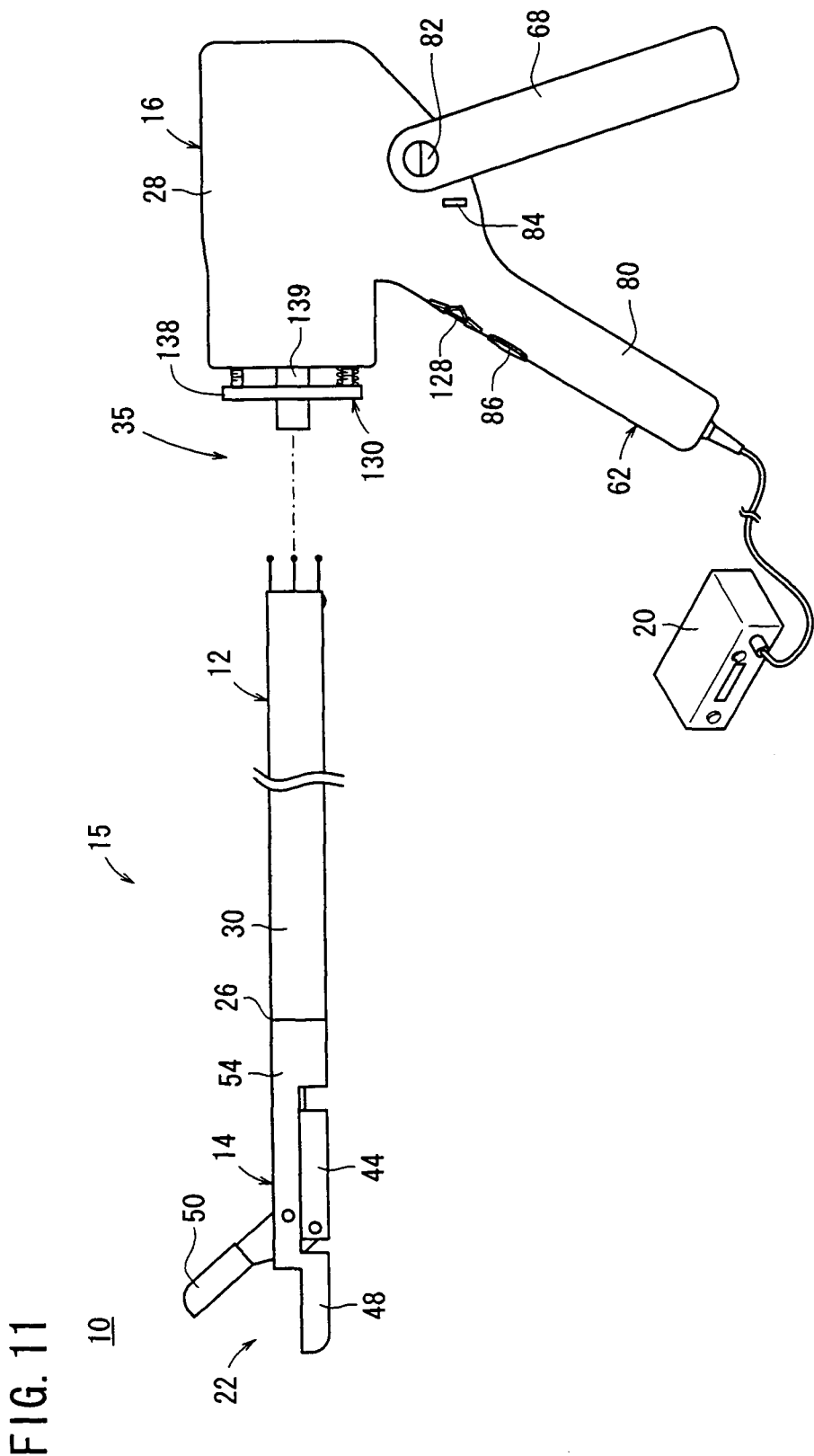
FIG. 11 is a side elevational view of the medical manipulator shown in FIG. 1, which is separated at the coupling.

As shown in FIG. 11, in the medical manipulator 10 according to the present embodiment, the operating unit 16 and the coupling 12 are detachably (separably) connected to each other by means of the detachable joint 35. Specifically, in the detachable joint 35, by which the coupling 12 and the operating unit 16 are detachably joined to each other, the protrusion 139 that projects on the distal end of the operating unit 16 is inserted into a hole 166 formed in the proximal end of the coupling 12, and a setscrew 168 is tightened against the protrusion 139 from the outer circumferential surface toward the inner circumferential surface of the coupling 12, thereby fastening the coupling 12 and the operating unit 16 together (see FIGS. 4 and 5).

In order to separate the coupling 12 and the operating unit 16 from each other, therefore, the wires 154 are released from the slits 152 of the tilt plate 138, the setscrew 168 is loosened, and the protrusion 139 of the operating unit 16 is pulled out of the hole 166 of the coupling 12 (see FIG. 11). At this time, the linear body 32 can easily be divided when the distal end portion 32a and the proximal end portion 32b are separated from each other at the connector 37, by releasing a T-shaped bar 170 on the distal end of the distal end portion 32a from a T-shaped hook 172 provided on the distal end of the proximal end portion 32b (see FIG. 12). Accordingly, various working units 15, with distal end working units having various end effectors, may easily be replaced and used on a single operating unit 16, so that the medical manipulator 10 has increased versatility and is low in cost. Since the working unit 15 can easily be separated from the operating unit 16, the working unit 15 (the distal end working unit 14) is easily maintained, enabling replacement, cleaning, and/or high-temperature sterilization thereof.

With the medical manipulator 10 thus constructed, as the gripper 22 is operated (opened and closed or angularly rotated), and the distal end working unit 14 is rotated by the single transmitting member 18, the installation space of the transmitting member 18 within the coupling 12 may be small. Accordingly, the coupling 12 may be thinner, while the distal end working unit 14 and the operating unit 16 may both be simpler in structure. The medical manipulator 10 according to the present embodiment can thus appropriately be used for performing laparoscopic surgery, brain surgery, thoracoscopic surgery, urologic surgery, or the like.

Operations of the medical manipulator 10 shall be described below.

In an initial state (non-operated state), the gripper 22 is open under the bias of the coil spring 46, and the movable handle 68 is open (see FIGS. 1, 3, and 5). When the operator grips the handle unit 62 by the hand, and turns the movable handle 68 in the direction indicated by the arrow in FIG. 1, the projecting member 124 is turned clockwise about the shaft member 82, thus causing the pin 126 to be pressed against the inner peripheral surface of the proximal end of the oblong hole 114 in order to move the tongue 116 and the support member 102 along the guide members 118, 120 (the state shown in FIG. 4). Since the flange 110 engages with the proximal end of the support member 102, the first coupling member 34 moves in the same direction as the support member 102, thereby pulling the transmitting member 18 toward the proximal end. Since the support member 102 moves toward the proximal end, the distal end of the prismatic portion 98b is inserted relatively deeply into the passage 108.

When the transmitting member 18 is pulled toward the proximal end, the slider 44 moves within the recess 56 toward the proximal end thereof, against the bias of the coil spring 46. Therefore, the pin 58 presses the inner peripheral surface of the proximal end of the oblong hole 60, thereby turning the movable pinching member 50 counterclockwise in FIG. 2 about the pin 52, and hence closing the movable pinching member 50 (the state shown in FIG. 2).

When the operator releases the hand from the handle unit 62, or reduces the gripping force on the handle unit 62, the slider 44 moves within the recess 56 toward the distal end thereof under the bias of the coil spring 46. Therefore, the pin 58 presses the inner peripheral surface of the distal end of the oblong hole 60, turning the movable pinching member 50 clockwise in FIG. 3 about the pin 52, and hence opening the movable pinching member 50 (the state shown in FIG. 3).

As the slider 44 moves toward the distal end, the transmitting member 18 also moves in the same direction. At the proximal end of the transmitting member 18, the flange 110 presses the support member 102, thereby moving the support member 102 and the tongue 116 toward the distal end along the guide members 118, 120. The inner peripheral surface of the proximal end of the oblong hole 114 presses the pin 126, turning the projecting member 124 and the movable handle 68 clockwise in FIG. 5 about the shaft member 82. The movable handle 68 now returns to its original open state (the state shown in FIG. 5). As the support member 102 moves toward the direction of the distal end, the distal end of the prismatic portion 98*b* moves nearly to the center of the passage 108 along the longitudinal direction thereof.

The movable pinching member 50 is opened and closed in mechanically (directly) ganged relation to the movable handle 68 when it is opened and closed. Therefore, if the gripper 22 grips an object (a surgical instrument or living tissue) when the movable handle 68 is manually pulled to a certain extent, then the gripper 22 and the slider 44 are unable to move further, so that the operator can feel through the fingertips that the object has been gripped.

If the object is a hard object, such as a surgical instrument, then the movable handle 68 is no longer movable at all in the closing direction. The operator can feel that the hard object has been gripped, and can reliably grip the object with strong forces, because the operator can transmit manual forces mechanically and directly to the gripper 22, rather than via an electromagnetic means. If gripping forces equivalent to manual forces were to be generated by a motor, then the motor would need to be considerably large in size and heavy, such a motor could not be housed readily in the main operating unit body 28, and would make the medical manipulator 10 heavier.

If the object is a soft object, such as a living tissue or the like, then the movable handle 68 can be displaced slightly in the closing direction, depending on the elasticity of the object. Therefore, the operator can feel that the soft object has been gripped, while recognizing how soft the object is, and can adjust the forces at which the object is gripped.

When the transmitting member 18 or the like is worn or degraded, friction increases and is transmitted to the movable handle 68, allowing the operator to sense a change in state, or an abnormal state, of the drive system, and hence, the operator can judge the timing of maintenance more appropriately.

As described above, since the movable pinching member 50 is opened and closed in a mechanically (directly) ganged relation to the movable handle 68 when it is opened and closed, the opening (gripping) forces of the fixed pinching member 48 and the movable pinching member 50 correspond to the opening (gripping) forces of the fixed handle 80 and the movable handle 68. Therefore, the operator can easily operate the gripper 22 with any desired opening (gripping) forces.

Specifically, the manual operation of the movable handle 68 is mechanically transmitted so as to open and close the gripper 22. The transmitting member 18, the slider 44, etc., provide an operation transmitting unit, which serves as a means for mechanically transmitting manual operations between the movable handle 68 and the gripper 22.

The term "mechanically" as used herein refers to a system for transmitting manual operations via a wire, a chain, a timing belt, a link, a rod, a gear, or the like, which is actuated primarily by a mechanical component in the form of a nonelastic solid body in the power transmitting direction, as described above. Although a wire, a chain, or the like is slightly elongatable inevitably under tension, it is still regarded as a mechanical component in the form of a nonelastic solid body. For example, although the transmitting member 18 has a flexible portion corresponding to at least the curvable portion 30, the transmitting member 18 is placed under an appropriate tension by the coil spring 46. When the gripper 22 is closed, the transmitting member 18 is pulled toward the operating unit 16 by the movable handle 68, and the transmitting member 18 essentially is not elastically deformed, or is inevitably elastically deformed only to an extent that is trouble-free in operation, thereby providing a mechanical connecting means (mechanical transferring means).

When the rotating action input unit 86 is operated in order to energize the rotational drive source 90 to rotate the driven gear 94, regardless of whether the movable pinching member 50 is opened or closed (regardless of the degree of opening thereof), rotating forces are transmitted successively to the prismatic portion 98*b* of the rotational shaft 98, the passage 108, the first coupling member 34, the linear body 32, the second coupling member 36, the passage 40, the protrusion 38, and the main distal end body 54, thereby rotating the distal end working unit 14. Thus, the rotating action mechanism 88 and the joint 26 function as a rotating mechanism, for rotating the distal end working unit 14 about its own axis. The direction that the driven gear 94 is driven is the same as the direction in which the distal end working unit 14 rotates.

The gripper 22 can be opened and closed, and the distal end working unit 14 can be rotated, when the coupling 12 is straight, bent, or curved. With the medical manipulator 10 according to the present embodiment, since the curvable portion 30 is not rotated, but rather only the distal end working unit 14 is rotated, even when the coupling 12 is bent or curved (i.e., the state indicated by the two-dot-and-dash lines in FIG. 1), as it rotates, the distal end working unit 14 is not swung about an axis that extends from the curvable portion 30 toward the proximal end. Therefore, the attitude of the gripper 22 (the direction in which the living tissue is gripped) can be changed, while the gripper 22 remains proximate to the region that is to be surgically treated.

With respect to the bending action mechanism 130, by simply operating the bending action input unit 128 to energize the bending drive sources 140, 142, regardless of whether the movable pinching member 50 is opened or closed (regardless of the degree of opening thereof), it is possible to tilt the tilt plate 138 to any desired angle, thereby easily bending the coupling 12 to a desired angle at the curvable portion 30. Specifically, the curvable portion 30 and the bending action mechanism 130 function as a bending mechanism for bending the gripper 22 in a direction crossing the axial direction of the coupling 12, so as to change the attitude of the gripper 22 easily and quickly.

With the medical manipulator 10 according to the present embodiment, as described above, the coupling 12 can be bent by the bending action mechanism 130, and the curvable portion 30 and the distal end working unit 14 can be rotated by the rotating action mechanism 88 easily and quickly through the bending drive sources 140, 142 and the rotational drive source 90, which serve as actuators, under the control of the controller 20, simply when the operator uses his fingertips to operate the bending action input unit 128 and the rotating action input unit 86 on the operating unit 16. Accordingly, the medical manipulator 10 has high operability. Specifically, in the medical manipulator 10, the bending mechanism for bending a portion (the curvable portion 30) of the coupling 12, and the rotating mechanism for rotating the distal end working unit 14 function cooperatively as an attitude changing mechanism, for changing the attitude of the distal end working unit 14, and such mechanisms operate through the actuators. The gripper 22 of the distal end working unit 14 is opened and closed (angularly moved) by the operator, who manually operates the fixed handle 80 and the movable handle 68 mechanically (directly) independently of the operation of the bending action mechanism 130, etc. Since the gripper 22 can be operated for acquiring desired gripping forces, the operator can treat the affected part more appropriately, while feeling the hardness of the gripped object. Specifically, it is ideal to operate the end effector (the gripper 22) by transmitting a manual action mechanically and directly thereto. Further, the best approach is to simplify operations of the bending action mechanism 130, the curvable portion 30, and the rotating action mechanism 88, which provide other attitude axes, i.e., the operation of the attitude changing mechanism, using the actuators (the bending drive sources 140, 142 and the rotational drive source 90). In other words, according to the present invention, since the distal end working unit 14 can easily be changed in attitude simply by pressing buttons with a single fingertip, for example, the attitude changing actions do not interfere with other actions of the operator to open and close the gripper 22 and to move the medical manipulator 10 in its entirety using the arm, thereby allowing the operator to perform a more intuitive surgical treatment.

Figure 14:
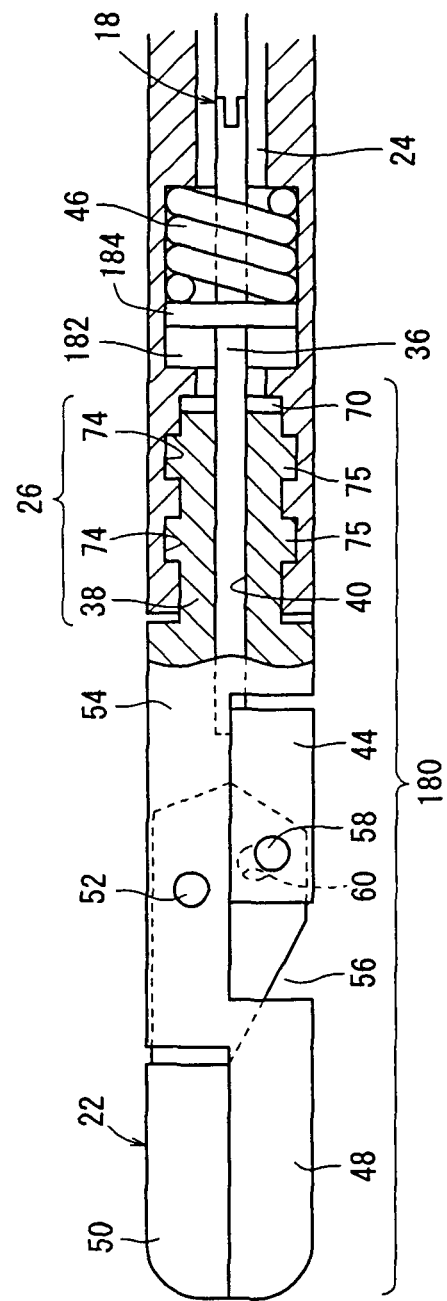
FIG. 14 is an enlarged side elevational view, partly in cross section, showing another structural example of the distal end portion of the medical manipulator shown in FIG. 1.

FIG. 14 is an enlarged side elevational view, partly in cross section, showing another structural example of the distal end portion of the medical manipulator 10 shown in FIG. 1.

A distal end working unit 180, as shown in FIG. 14, is arranged to have a biasing means, for biasing the movable pinching member 50 in the opening direction, disposed in the vicinity of the distal end working unit 14. The coil spring 46 is housed in a large-diameter portion 182, which is greater in diameter than the space 24, formed at a position adjacent to the proximal end of the joint 26 of the coupling 12. Within the large-diameter portion 182, the second coupling member 36 extends through the coil spring 46, and a disk-shaped flange 184 is fixed to or integrally combined with a portion of the second coupling member 36, which extends from the coil spring 46 toward the distal end. The coil spring 46 in the compressed state has a proximal end thereof held against the proximal end face of the large-diameter portion 182, and a distal end held against the flange 184, and biases the second coupling member 36 toward the distal end.

The biasing means is not limited to the coil spring 46, but may comprise another spring, such as a torsion spring, a leaf spring, or the like, or an elastic material such as rubber, or a permanent magnet or an electromagnet. The biasing means may be disposed within the operating unit 16.

During surgical operations, a large peeling force may be required in the direction (peeling direction) in order to open the gripper 22 for peeling off tissue. If the coil spring 46 is replaced with a tension spring, and the pushing action of the movable handle 68 is transmitted directly to the gripper 22 via the slider 44, then a large peeling force can be produced. On the medical manipulator 10, the force applied in the opening direction of the gripper 22 is transmitted to the movable handle 68. Specifically, when the gripper 22 abuts against a living tissue or a surgical instrument in the opening direction thereof at the time the gripper 22 is opened, the movable handle 68 stops moving in the opening direction. Thus, the operator can feel that the gripper 22 has come into abutment against something.

The rotating action mechanism 88, the bending action mechanism 130, the joint 26, the converting means 100, the operating unit 16, the detachable joint 35, the connector 37, etc., are not limited to the aforementioned illustrated structural details. In the present embodiment, the surgical operation means may comprise a pair of opening and closing members, which are angularly movable, or which may be openable and closable by being translated. Further, the surgical operation means may comprise a single member, which is angularly movable, such as a bendable forceps, an electrosurgical knife, an ultrasonic knife, or the like.

The rotational drive source 90 and the bending drive sources 140, 142, which are actuators for actuating the rotating action mechanism 88 and the bending action mechanism 130, may comprise fluid-pressure actuators, using a fluid such as a gas, a liquid, or the like, for example, rather than electric motors.

The rotating action input unit 86 and the bending action input unit 128 may also be constructed as foot switches, rather than being provided on the operating unit 16. In this case, foot switches may be placed at the operator's feet for allowing the operator to perform manual techniques more smoothly.

The movable handle 68, the rotating action input unit 86, and the bending action input unit 128 on the operating unit 16 are not limited to the positions, forms, and operating methods that have been illustrated above. The rotating action input unit 86 may be replaced with operating rollers, buttons, or a joystick. Further, various positions and methods that allow the manipulator to be easily operated may be selected and designed.

A medical manipulator 1010 according to another embodiment will be described below with reference to FIGS. 15 to 57.

Figure 15:
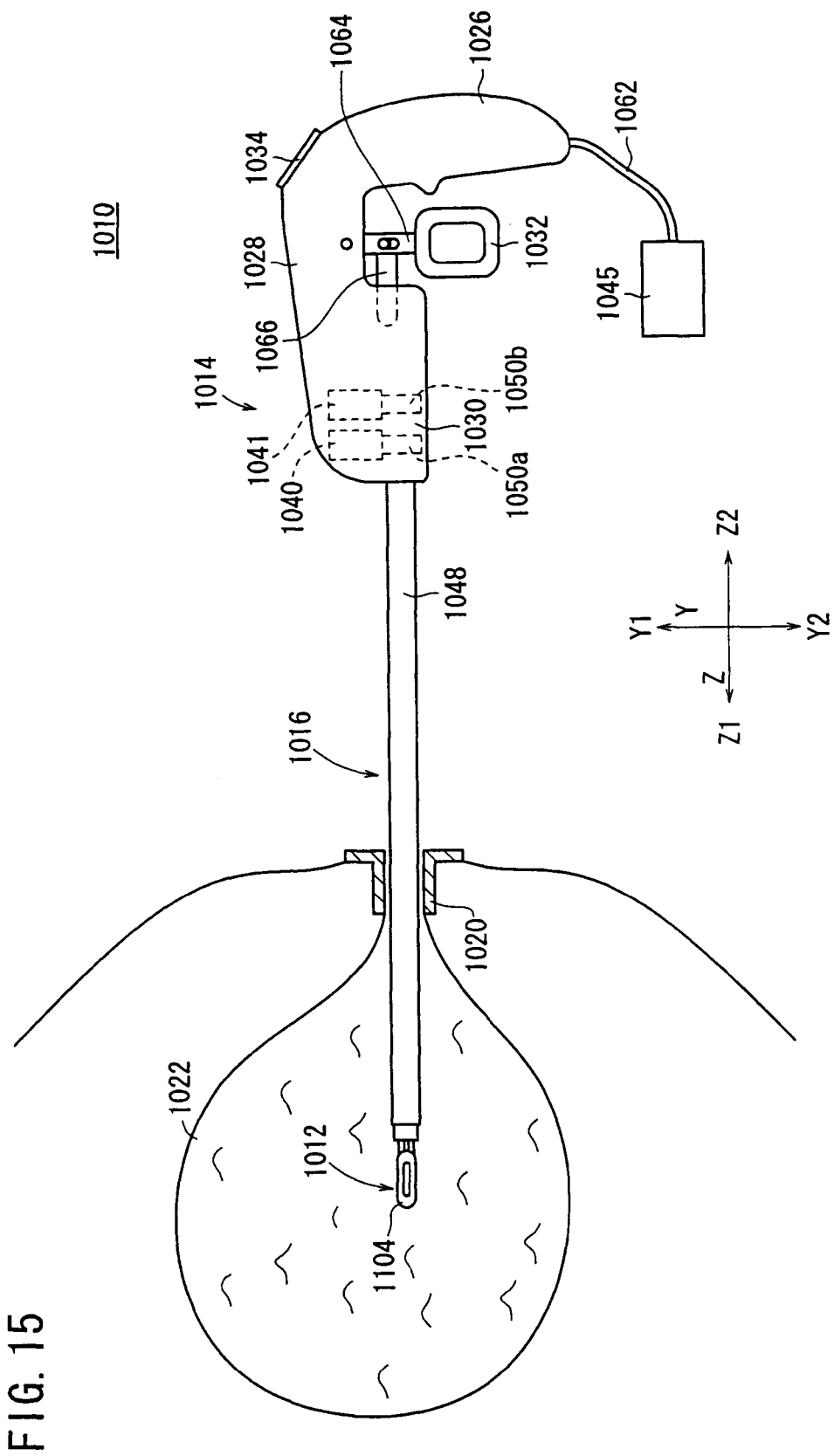
FIG. 15 is a side elevational view of a medical manipulator according to another embodiment of the present invention.

As shown in FIG. 15, the medical manipulator 1010 according to the present embodiment makes up part of a medical manipulator system, and is connected to a controller 1045.

The controller 1045, which serves to control the medical manipulator 1010 electrically, is connected via a connector to a cable 1062 extending from a lower end of a grip handle 1026. The controller 1045 can control a plurality of medical manipulators 1010 independently of each other. Of course, a controller for controlling a single medical manipulator 1010 may also be used.

The medical manipulator 1010 includes a distal end working unit 1012 for gripping a portion of a living tissue, and a curved needle, or the like for performing a given surgical treatment. The medical manipulator 1010 usually is referred to as a gripping forceps or a needle driver (needle holder).

Figure 16:
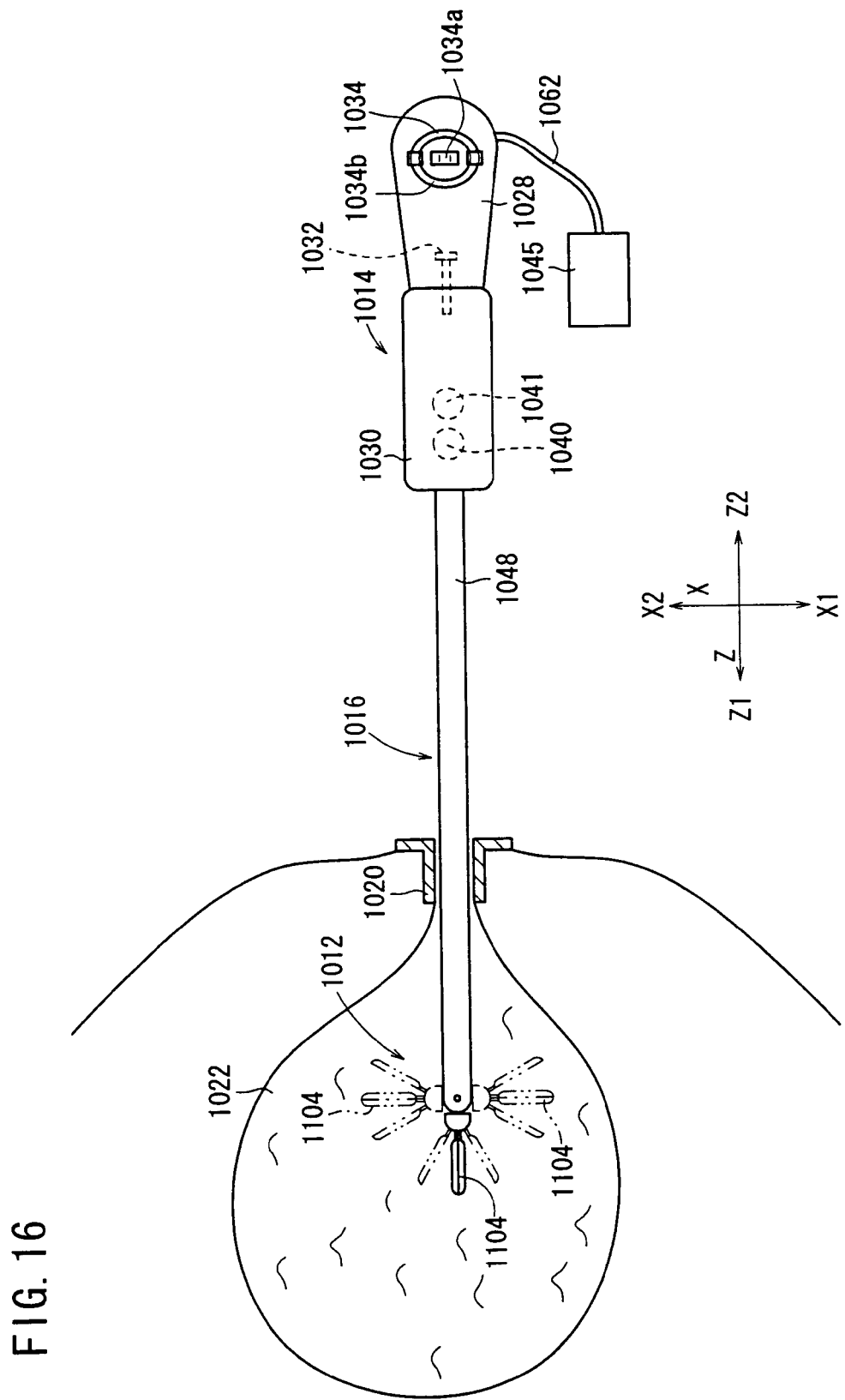
FIG. 16 is a plan view of the medical manipulator shown in FIG. 15.
Figure 17:
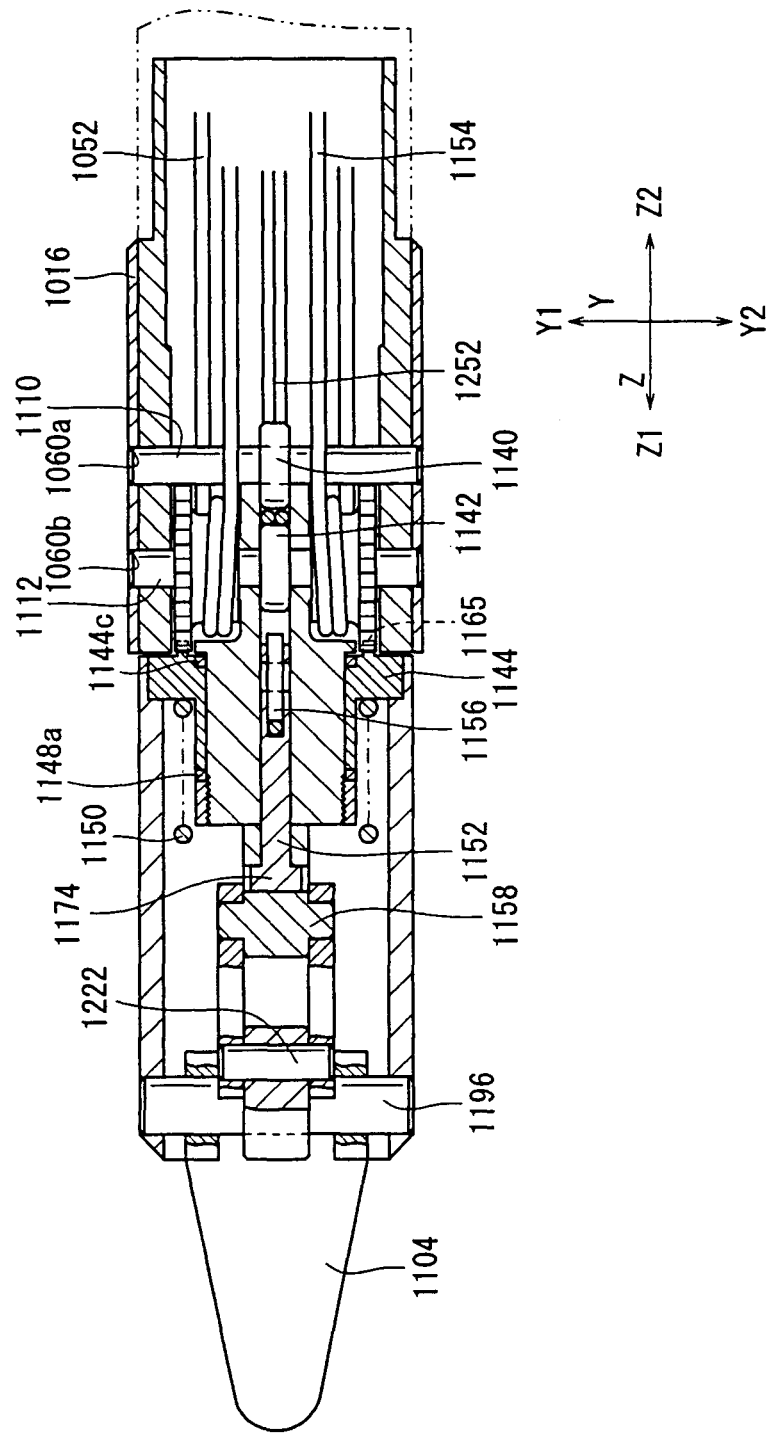
FIG. 17 is a sectional side elevational view of a distal end working unit according to a first structural example.
Figure 18:
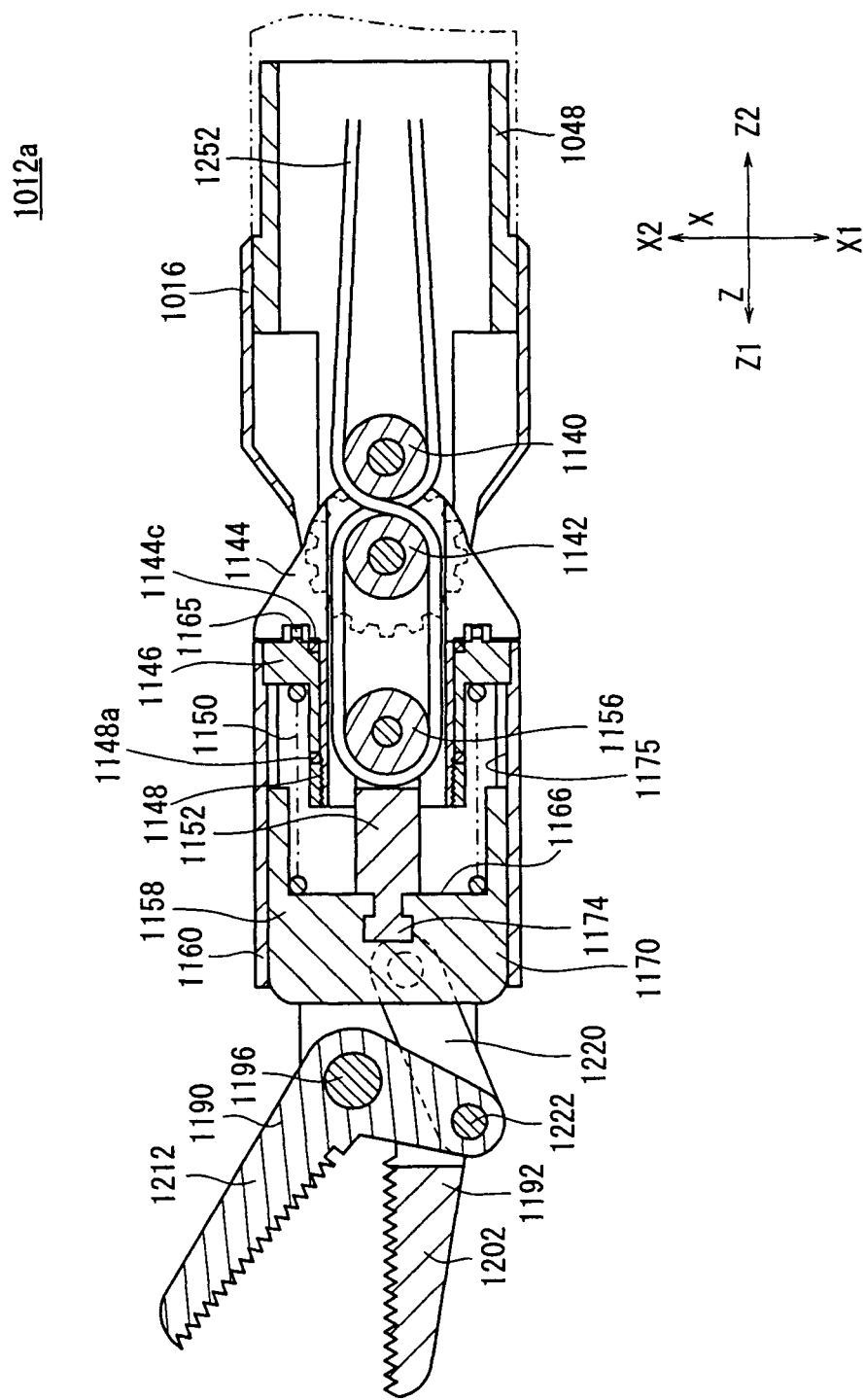
FIG. 18 is a sectional plan view of the distal end working unit according to the first structural example.

As shown in FIGS. 15 and 16, the medical manipulator 1010 comprises an operating unit 1014, which is held and operated by the hand, and a working unit 1016 fixed to the operating unit 1014. The operating unit 1014 and the working unit 1016 are integrally combined with each other. However, depending on conditions, the operating unit 1014 and the working unit 1016 may be separable from each other.

In the following description, it shall be assumed that transverse directions in FIGS. 15 and 16 are referred to as X directions, vertical directions as Y directions, and longitudinal directions of a connector shaft 1048 as Z directions. Among the X directions, the rightward direction as viewed from the distal end is referred to as an X1 direction, and the leftward direction as an X2 direction. Among the Y directions, the upward direction is referred to as a Y1 direction, and the downward direction as a Y2 direction. Among the Z directions, the forward direction is referred to as a Z1 direction, and the rearward direction as a Z2 direction. Unless otherwise noted, these directions represent directions of the medical manipulator 1010 when it is in a neutral posture. The above definitions of directions are for illustrative purposes only. The medical manipulator 1010 can be used in any of various orientations, e.g., it may be used upside down.

The working unit 1016 comprises a distal end working unit 1012 for performing working operations, and an elongate hollow connector shaft (coupling) 1048 coupling the distal end working unit 1012 and the operating unit 1014 to each other. The distal end working unit 1012 and the connector shaft 1048 have a small diameter, and can be inserted into a body cavity 1022 through a trocar 1020 in the form of a hollow cylinder mounted inside an abdominal region or the like of the patient. The working unit 1012 is actuated by a composite input unit 1034 in order to perform various techniques to grip, remove, suture, or tie-knot an affected part of the patient's body within the body cavity 1022.

The operating unit 1014 includes a grip handle 1026, which is gripped by the hand, a bridge 1028 extending from an upper portion of the grip handle 1026, and an actuator block 1030 and a trigger lever (input unit) 1032, which are connected to a distal end of the bridge 1028.

As shown in FIG. 15, the grip handle 1026 of the operating unit 1014 extends in the Y2 direction from the end of the bridge 1028, and has a length suitable for being gripped by the hand. The composite input unit 1034 is disposed on the grip handle 1026.

The cable 1062 connected to the controller 1045 is disposed on a lower end of the grip handle 1026 while being integrally connected to the grip handle 1026. The grip handle 1026 and the cable 1062 may be connected to each other by a connector.

The composite input unit 1034 makes up a composite input means for imparting rotational commands in rolling (shaft rotating) and yawing (left and right) directions to the distal end working unit 1012. For example, commands in the yawing direction are given by a first input means 1034a, which operate in the lateral direction, whereas commands in the rolling direction are given by a second input means 1034b, which operate in the shaft rotating direction. The trigger lever 1032 comprises an input means for imparting opening and closing commands for an end effector 1104 (see FIG. 15) of the distal end working unit 1012. Although the end effector 1104 is available in various forms, the medical manipulator 1010 employs an openable and closable gripper.

The composite input unit 1034 includes an input sensor for detecting a control variable, and supplies a detection operation signal (e.g., an analog signal) to the controller 1045.

The trigger lever 1032 comprises a lever disposed below the bridge 1028 and is disposed at a position where it can easily be operated by the index finger. The trigger lever 1032 is connected to the actuator block 1030 by a first link 1064 and a second link 1066, and is movable toward and away from the grip handle 1026. The first link 1064 pivots swingably about a portion of the bridge 1028, and the trigger lever 1032 is mounted on the end of the first link 1064 in the Y2 direction. The second link 1066 projects in the Z2 direction from the actuator block 1030 and engages in an oblong hole 1064a formed in the first link 1064. The second link 1066 is movable back and forth in the longitudinal direction in the oblong hole 1064a when the trigger lever 1032 is moved.

The second link 1066 is connected to an end of a wire (drive member) 1056. When the trigger lever 1032 is pulled, the wire 1056 also is pulled in unison therewith. Since the wire 1056 is used as a drive member (transmitting member) connected to the second link 1066, the number of parts used can be reduced, and the medical manipulator 1010 is reduced in weight.

The drive member connected to the second link 1066 may comprise a rigid linearly movable rod (or link), for example, rather than the wire 1056. Since a rod is generally more rigid than the wire, the rod may be used as a linearly movable member for producing large gripping forces. The rod and the second link 1066 may be combined integrally with each other.

Links, gears, etc., may be operatively disposed between the second link 1066 and the wire 1056, for adjusting the operating forces and strokes of the operator.

The actuator block 1030 houses motors (attitude axis actuators) 1040, 1041 therein corresponding to the respective mechanisms of two out of three degrees of freedom, which are incorporated in the distal end working unit 1012. The motors 1040, 1041 are arrayed in parallel with each other in the longitudinal direction of the connector shaft 1048. The motors 1040, 1041 correspond to movements in both rolling and yawing directions of the distal end working unit 1012, i.e., movements of the attitude changing mechanism, for changing the attitude of the distal end working unit 1012. The motors 1040, 1041 are small in size and diameter, thus enabling the actuator block 1030 to be compact and flat in shape. The motors 1040, 1041 can be energized to rotate the drive shafts under the control of the controller 1045, based on operation of the operating unit 1014. The motors 1040, 1041 are combined with angle sensors, for detecting rotational angles and supplying the detected angle signals to the controller 1045. The angle sensors may comprise rotary encoders, for example. Rather than electric motors, the actuators may comprise fluid-pressure actuators, using a fluid such as a gas, liquid, or the like, for example.

The actuator block 1030 houses pulleys 1050a, 1050b therein, which are connected, respectively, to the drive shafts of the motors 1040, 1041.

Wires 1052, 1054 are wound respectively around the pulleys 1050a, 1050b, and extend through a hollow region 1048a (see FIG. 20) in the connector shaft 1048 toward the distal end working unit 1012. The wires 1052, 1054 may both be of the same type and have the same diameter.

The composite input unit 1034 and the trigger lever 1032 of the operating unit 1014 are not limited to the above-described and illustrated positions, forms, and operating methods. For example, the composite input unit 1034 may be replaced with operating rollers, buttons, or a joystick. Further, other positions and methods, which allow the manipulator to be easily operated, may be selected and designed.

A manual operation applied to the trigger lever 1032 is mechanically transmitted to open and close the end effector 1104. The first link 1064, the second link 1066, the wire 1056, and an end effector driving mechanism 1260, to be described later, serve as a means (transmitting members) for mechanically transmitting a manual action between the trigger lever 1032 and the end effector 1104, and make up an operation transmitting unit.

The term "mechanically" refers to a system for transmitting manual operations via a wire, a chain, a timing belt, a link, a rod, a gear, or the like, which is mainly actuated in the power transmitting direction by a mechanical component in the form of a nonelastic solid body. Although a wire, a chain, or the like, is slightly elongatable inevitably under tension, it is still regarded as a mechanical component in the form of a nonelastic solid body.

First through fifth structural examples 1012*a* through 1012*e*, and a modification 1012*f* of the distal end working unit 1012, shall be described below.

As shown in FIGS. 17, 18, 19, 20, and 21, the distal end working unit 1012*a* according to the first structural example comprises a wire-driven mechanism 1100, a composite mechanism 1102, and an end effector 1104. The distal end working unit 1012 incorporates therein mechanisms providing three degrees of freedom. These mechanisms include a mechanism having a first degree of freedom for angularly moving a portion of the distal end working unit 1012 that is positioned ahead of a first rotational axis Oy extending along the Y direction, in a yawing direction about the first rotational axis Oy, a mechanism having a second degree of freedom for angularly moving the portion of the distal end working unit 1012 in a rolling direction about a second rotational axis Or, and a mechanism having a third degree of freedom for opening and closing the end effector 1104 on the distal end of the distal end working unit 1012 about a third rotational axis Og.

The first rotational axis Oy of the mechanism having the first degree of freedom may be angularly movable out of parallelism with an axis C, which extends from the proximal end to the distal end of the connector shaft 1048. The second rotational axis Or of the mechanism having the second degree of freedom may be angularly movable, about an axis along the direction in which the distal end (the end effector 1104) of the distal end working unit 1012 extends, with the distal end portion thereof being rotatable in the rolling direction.

The mechanism having the first degree of freedom (i.e., which is movable in the yawing direction) comprises a bending mechanism having an operable range of ±90° or greater, for example. The mechanism having the second degree of freedom (i.e., which is movable in the rolling direction) comprises a rotating mechanism having an operable range of ±180° or greater, for example. The mechanism having the third degree of freedom (i.e., the end effector 1104) may be opened through 400 or greater, for example.

The end effector 1104 comprises a member for performing actual work during an operation. The first rotational axis Oy and the second rotational axis Or are attitude axes of the attitude changing mechanism, for changing the attitude of the end effector 1104 for facilitating the work. Generally, the mechanism having the third degree of freedom for opening and closing the end effector 1104 is referred to as a gripper (or a gripper axis). The mechanism having the first degree of freedom for turning in a yawing direction is referred to as a yaw axis, and the mechanism having the second degree of freedom for turning in a rolling direction is referred to as a roll axis.

The wire-driven mechanism 1100 is disposed between a pair of tongue pieces 1058 and serves to convert reciprocating movement of the respective wires 1052, 1054 into rotational movement, and to transmit such rotational movement to a composite mechanism 1102. The wire-driven mechanism 1100 includes a shaft 1110, which is inserted into shaft holes 1060*a*, 1060*a*, and a shaft 1112, which is inserted into shaft holes 1060*b*, 1060*b*. The shafts 1110, 1112 are press-fitted or welded securely to the shaft holes 1060*a*, 1060*b*. The shaft 1112 is aligned axially with the first rotational axis Oy.

Gear bodies 1126, 1130, which are symmetrically shaped in the Y direction, are mounted respectively on both ends of the shaft 1112, respectively, in the Y direction. The gear body 1126 comprises a tubular member 1132 and a first gear 1134 disposed concentrically on an upper portion of the tubular member 1132. The gear body 1130 is essentially identical in shape to the gear body 1126, and is aligned with the gear body 1126 in the Y direction. The gear body 1130 comprises a tubular member 1136 and a second gear 1138 disposed concentrically on a lower portion of the tubular member 1136. The gears 1134, 1138 are held in mesh with upper and lower ends of the face gear 1165 of a gear body 1146, to be described later.

The tubular member 1136 is substantially identical in diameter and shape to the tubular member 1132. Wires 1052, 1054 are wound around the tubular members 1132, 1136 and have portions fastened thereto by a securing means. The wires 1052, 1054 are wound 1.5 turns (540°) around the tubular members 1132, 1136.

When the wires 1052, 1054 are rotated, the gear bodies 1126, 1130 are rotated about the shaft 1112. When the gear bodies 1126, 1130 are rotated at the same speed and in the same direction, the gear body 1146 swings with respect to the shaft 1112 and moves in a yawing direction. When the gear bodies 1126, 1130 are rotated at the same speed and in the opposite direction, the gear body 1146 is rotated about the second rotational axis Or and moves in a rolling direction. When the gear bodies 1126, 1130 are rotated at different speeds, the gear body 1146 undergoes a composite motion in both yawing and rolling directions. The gear body 1126, the gear body 1130, and the gear body 1146 collectively make up a differential mechanism.

An idle pulley (a cylindrical member, a transmitting member) 1140 is rotatably supported substantially centrally on the shaft 1110. A guide pulley (a cylindrical member, a transmitting member) 1142 is rotatably supported substantially centrally on the shaft 1112. The idle pulley 1140 serves to keep a driven wire (a flexible member, a transmitting member) 1252 wound around the guide pulley 1142 through a constant angle (about 180° on both sides) at all times. Instead of using the idle pulley 1140, the driven wire 1252 may also be wound one or more turns around the guide pulley 1142. The idle pulley 1140 and the guide pulley 1142 may have a smooth surface, and may be made of a material having a small coefficient of friction, in order to reduce slippage and frictional wear on the driven wire 1252 (see FIG. 22). The guide pulley 1142 is disposed around the yaw axis Oy of the attitude changing mechanism.

A main shaft 1144 is rotatably supported on the shaft 1112 between the gear body 1126 and the guide pulley 1142, as well as between the guide pulley 1142 and the gear body

1130. The main shaft 1144 has a sleeve projecting toward the composite mechanism 1102. The main shaft 1144 has a square hole 1144a formed axially therein. The main shaft 1144 includes two auxiliary plates 1144b disposed on one end in the Z2 direction for holding both surfaces of the guide pulley 1142 in the Y direction. The auxiliary plates 1144b have respective holes through which the shaft 1112 extends. The auxiliary plates 1144b have chevron shapes, which become progressively wider in the Z1 direction, for preventing foreign matter such as threads from entering therein.

The composite mechanism 1102 includes an opening/closing mechanism for opening and closing the end effector 1104, and an attitude changing mechanism for changing the attitude of the end effector 1104.

The composite mechanism 1102 comprises a gear body 1146 rotatably fitted over the circumferential surface of the sleeve of the main shaft 1144, a nut 1148 mounted on the distal end of the main shaft 1144, a spring 1150, a rod (a transmitting member) 1152 with a square cross-sectional shape and having an end in the Z2 direction, which is inserted into the hole 1144a, a driven pulley (a cylindrical member, a transmitting member) 1156 rotatably supported on the end in the Z2 direction of the rod 1152 by a pin 1154, a driven plate (a transmitting member) 1158, and a hollow cylindrical cover 1160. The spring 1150 comprises a compression spring. The end in the Z2 direction of the rod 1152 is channel-shaped for improving slidability thereof with respect to the driven pulley 1156, and the end of the rod 1152 projects largely in the Z2 direction.

A thrust bearing 1144c made of resin is disposed on the portion of the main shaft 1144 that abuts against the gear body 1146. A further thrust bearing 1148a made of resin is disposed on the portion of the nut 1148 that abuts against the gear body 1146. The thrust bearings 1144c and 1148a have a low coefficient of friction, for reducing wear and torque on the abutting portions, and for preventing loads from being applied directly to the face gear 1165. The thrust bearings 1144c, 1148a comprise slide bearings, for example, but may comprise rolling bearings, thereby allowing the medical manipulator to operate smoothly about the roll axis even when the end effector 1104 is strongly closed or opened, i.e., even when the gear body 1146 abuts firmly against the main shaft 1144.

The gear body 1146 is of a stepped shape, comprising a large-diameter portion 1162 in the Z2 direction, a small-diameter portion 1164 in the Z1 direction, and a face gear 1165 on the end of the large-diameter portion 1162 in the Z2 direction. The face gear 1165 is held in mesh with the gears 1134, 1138. The gear body 1146 prevents the nut 1148 from becoming dislodged from the main shaft 1144. The large-diameter portion 1162 has an externally threaded outer circumferential surface.

The driven plate 1158 has a recess 1166 in the Z2 direction, an engaging cavity 1168 formed in the bottom of the recess 1166, axial ribs 1170 disposed respectively on both surfaces in the Y direction, and a link hole 1172. The engaging cavity 1168 has a shape that is engageable with a mushroom-shaped knob 1174 on the distal end of the rod 1152. When the mushroom-shaped knob 1174 engages in the engaging cavity 1168, the driven plate 1158 and the rod 1152 are capable of rotating relatively with respect to each other about the roll axis. The driven plate 1158 has a width that is substantially equal to the inside diameter of the cover 1160.

The cover 1160 has a size that is large enough to cover the composite mechanism 1102 substantially in its entirety, and serves to prevent foreign matter (living tissue, medications, threads, etc.) from entering into the composite mechanism 1102 and the end effector 1104. The cover 1160 has two axial grooves 1175 formed in an inner circumferential surface thereof in diametrically confronting relation to each other. The ribs 1170 of the driven plate 1158 are fitted respectively in the grooves 1175 for axially guiding the driven plate 1158. Since the knob 1174 engages in the engaging cavity 1168 of the driven plate 1158, the driven pulley 1156 is axially movable back and forth within the hole 1144a, in unison with the driven plate 1158 and the rod 1152, and can roll about the rod 1152. The cover 1160 is fixed to the large-diameter portion 1162 of the gear body 1146 by threaded engagement therewith, or by a press-fitted engagement, or the like.

The spring 1150 is fitted between the step of the gear body 1146 and the recess 1166 of the driven plate 1158, for normally biasing the driven plate 1158 to move forward into abutment against a stopper.

The end effector 1104 comprises a first end effector member 1190, a second end effector member 1192, and a pin 1196. The pin 1196 is disposed on the third rotational axis Og.

The first end effector member 1190 has a pair of side walls 1200 facing each other laterally, holes 1200a formed respectively in the distal ends of the side walls 1200, and a first gripper 1202 projecting in the Z1 direction from lower portions of the distal ends of the side walls 1200. The hole 1200a has a diameter such that the pin 1196 can be press-fitted into the hole 1200a. The first gripper 1202 becomes progressively narrower in the Z1 direction and includes an arcuate distal end portion. The first gripper 1202 has a number of conical teeth disposed closely together over the entire surface thereof, which faces in the Y1 direction. The first end effector member 1190 is coupled to the cover 1160 by a given coupling means. For example, the first end effector member 1190 and the cover 1160 may be of an integral structure, providing a composite tubular body 1230.

The cover 1160 is coupled at a proximal portion to the gear body 1146 (by threaded engagement, press-fitted engagement, welding, or the like). When the gear body 1146 is rotated, the cover 1160 and the first end effector member 1190 operate about the roll axis.

The second end effector member 1192 is L-shaped, comprising a second gripper 1212 extending in the Z direction, and a lever 1214 bent about 60° with respect to the second gripper 1212. The second end effector member 1192 has a hole 1216 formed in the L-shaped bent corner, and the lever 1214 has a hole 1218 formed therein near to the end portion thereof. When the pin 1196 is inserted into the hole 1216, the second end effector member 1192 is swingable about the third rotational axis Og. The second gripper 1212 has a shape that is identical to the first gripper 1202, yet is disposed in an inverted fashion. When the second end effector member 1192 is angularly moved about the third rotational axis Og, the second end effector member 1192 abuts against the first gripper 1202 for gripping a curved needle or the like.

The lever 1214 and the driven plate 1158 are joined to each other by two parallel gripper links 1220. Specifically, a pin 1222 is inserted into holes 1220a formed in respective ends of the gripper links 1220 and the hole 1218, whereas a pin 1124 is inserted into holes 1220b formed respectively in other ends of the gripper links 1220 and the hole 1172.

Figure 19:
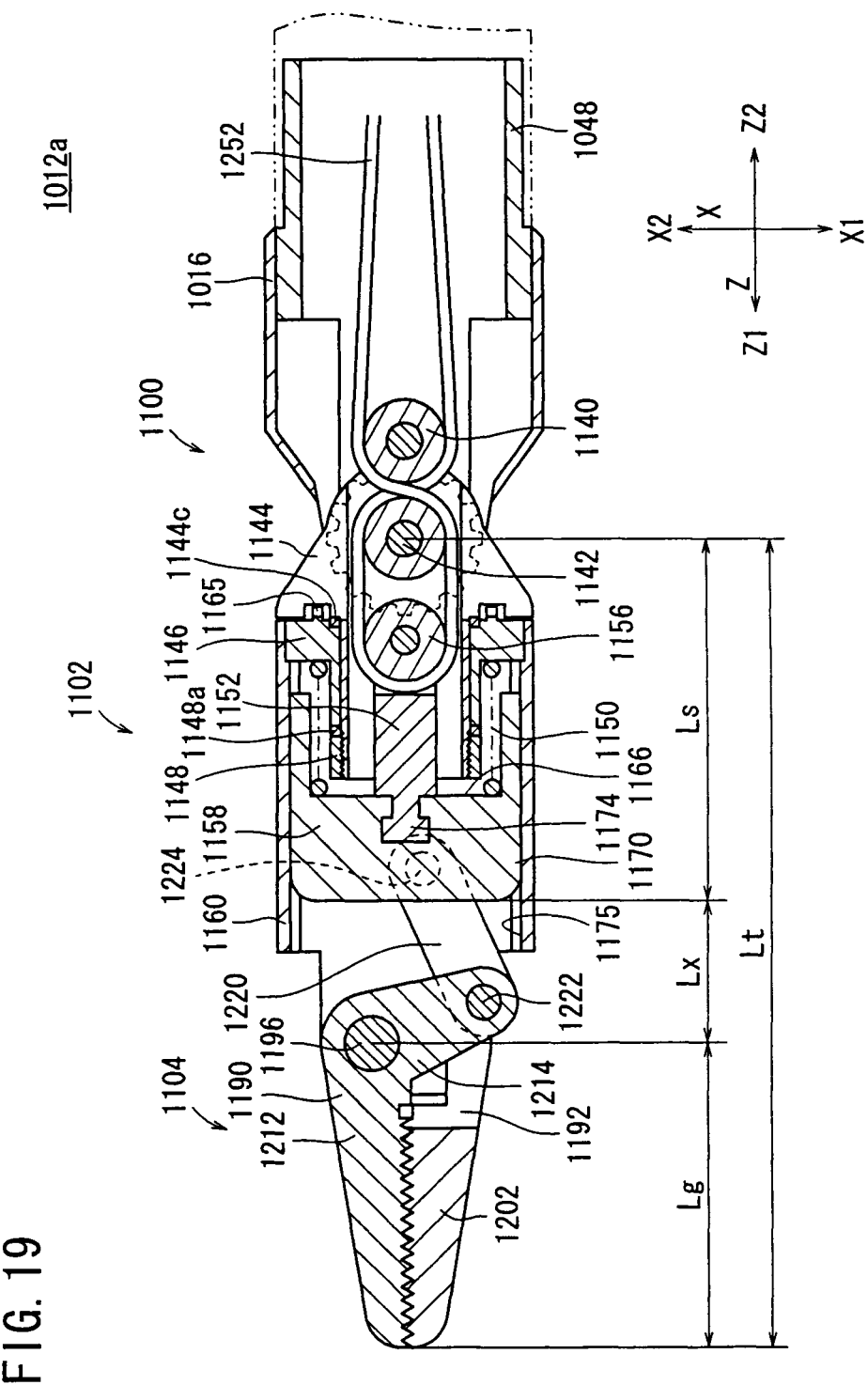
FIG. 19 is a sectional side elevational view of the distal end working unit according to the first structural example, with a gripper being closed.
Figure 20:
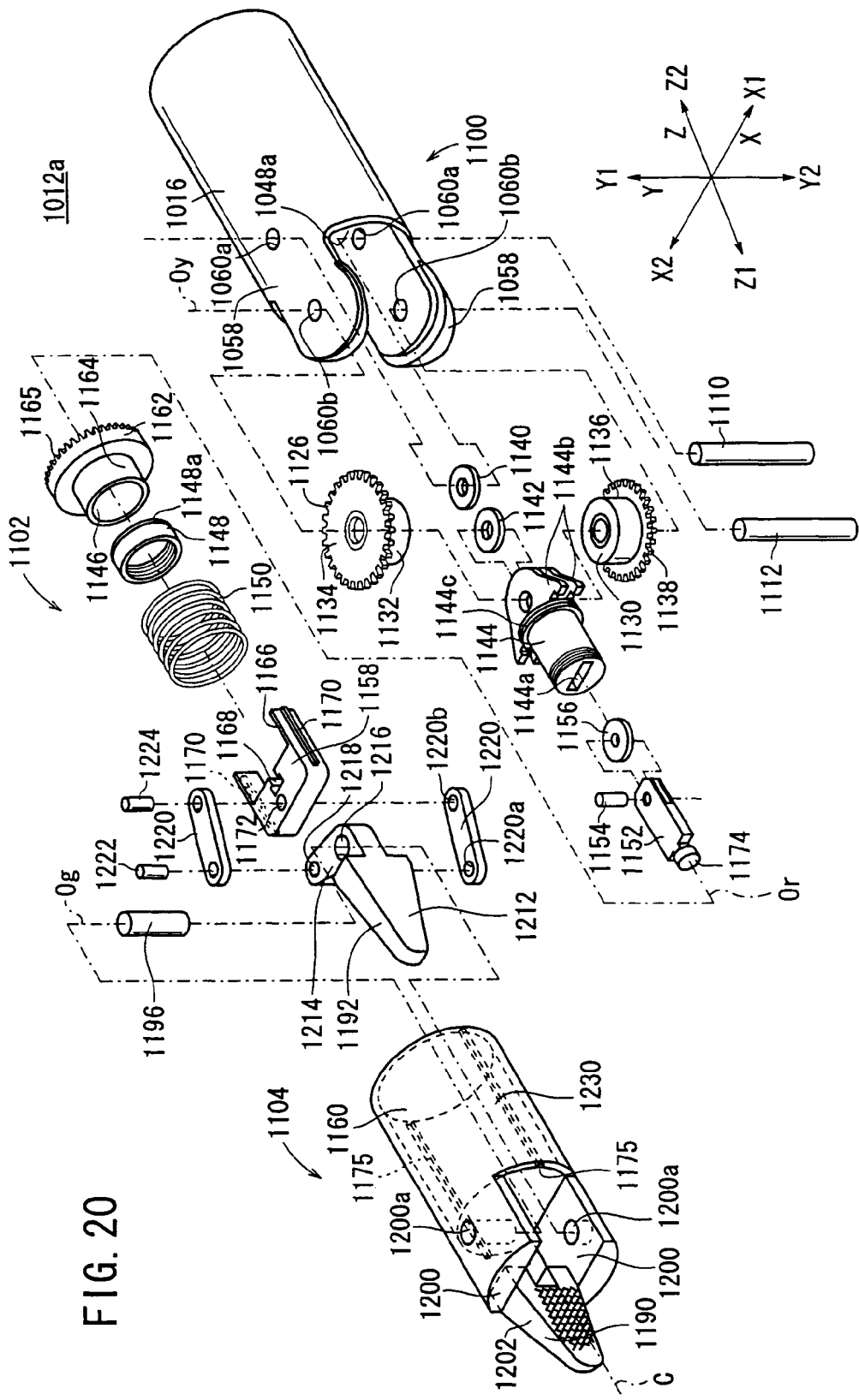
FIG. 20 is an exploded perspective view of the distal end working unit according to the first structural example.

The position of the pin 1124, by which the gripper links 1220 are pivotally supported, is slightly offset from the central axis in FIG. 19 (as viewed in side elevation). However, the pin 1124 may be positioned on the central axis as viewed in side elevation. The position of the pin 1124 may be determined in view of the balance of acting forces, the space, and the ease with which to assemble the parts. The pins may be integrally combined with the gripper links 1220.

Two gripper links 1220 are disposed in parallel to each other, for adequately balancing the forces, and for preventing the application of inadvertent moment loads. Depending on design conditions, only one gripper link may be employed.

When the driven pulley 1156, the rod 1152, and the driven plate 1158 are moved in the Z2 direction, the lever 1214 also is pulled in the Z2 direction, causing the second gripper 1212 to move toward the first gripper 1202 so as to grip an object therebetween. Conversely, when the driven pulley 1156, the rod 1152, and the driven plate 1158 are moved in the Z1 direction by action of the spring 1150, the lever 1214 also is pushed in the Z1 direction, causing the second gripper 1212 to move away from the first gripper 1202 and open the end effector 1104. Since the driven plate 1158 is normally biased by the spring 1150 to move in the Z1 direction, when the medical manipulator is not manually operated, the second gripper 1212 is spaced from the first gripper 1202 thereby opening the end effector 1104. The spring 1150 is effective to keep the wire 1056 and the driven wire 1252 under a suitable tension and prevent them from sagging. Therefore, play between the various parts is prevented and the medical manipulator is capable of gripping objects with high responsiveness.

For the sake of brevity, the term "end effector 1104" will hereinafter be used to refer to the first gripper 1202 and the second gripper 1212.

Figure 21:
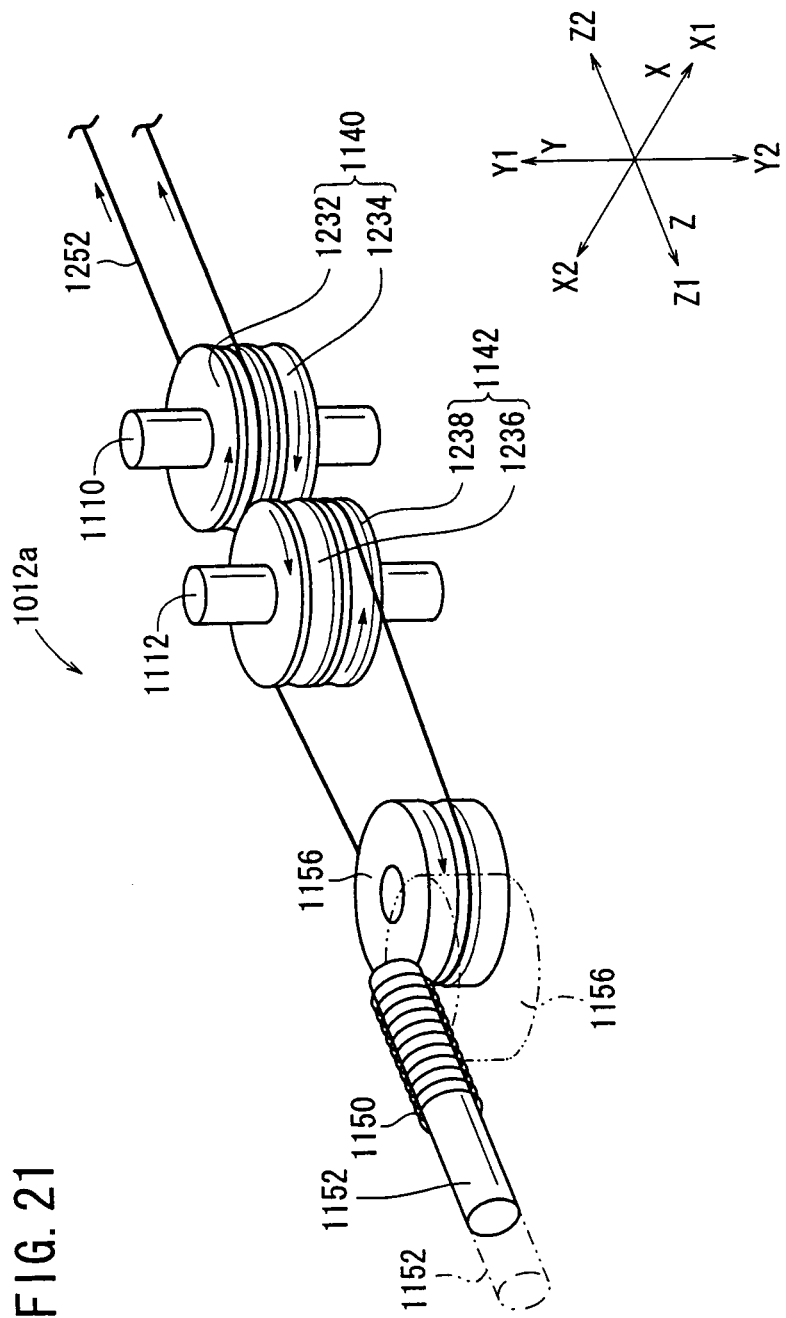
FIG. 21 is a schematic structural view of the distal end working unit according to the first structural example.

As shown in FIG. 21, the idle pulley 1140 comprises two parallel pulleys, i.e., a first layer idle pulley (first layer idle cylindrical body) 1232 and a second layer idle pulley (second layer idle cylindrical body) 1234, which are aligned coaxially with each other. The guide pulley 1142 comprises two parallel pulleys, i.e., a first layer guide pulley (first layer guide cylindrical body) 1236 and a second layer guide pulley (second layer guide cylindrical body) 1238, which are aligned coaxially with each other.

At the end in the Z2 direction in FIG. 21, one of the stretches of the driven wire 1252 is held against surfaces of the first layer idle pulley 1232 in the X1 and Z1 directions, and also is held against surfaces of the first layer guide pulley 1236 in the Z2 and X2 directions, while extending to the driven pulley 1156.

At the end in the Z2 direction in FIG. 21, the other stretch of the driven wire 1252 is held against surfaces of the second layer idle pulley 1234 in the X2 and Z1 directions, and also is held against surfaces of the second layer guide pulley 1238 in the Z2 and X1 directions, while extending to the driven pulley 1156.

When the wire 1056 (see FIG. 22) is pulled in the Z2 direction, for example, the first layer idle pulley 1232 and the second layer guide pulley 1238 are rotated counterclockwise as viewed in plan, whereas the second layer idle pulley 1234 and the first layer guide pulley 1236 are rotated clockwise as viewed in plan. Since each of the idle pulley 1140 and the guide pulley 1142 comprises two parallel coaxial pulleys, the pulleys are rotatable in opposite directions when the driven wire 1252 held thereagainst is moved, and hence the pulleys operate smoothly.

Figure 22:
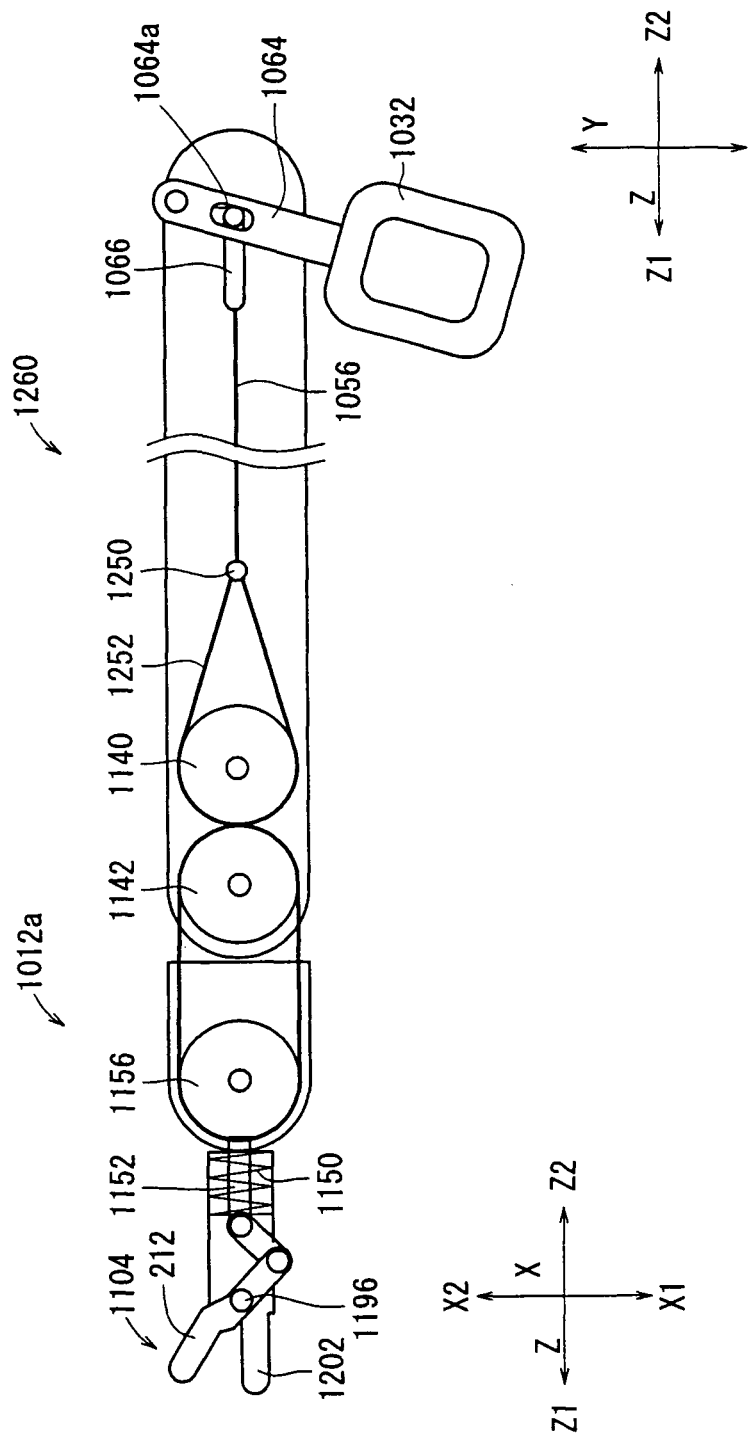
FIG. 22 is a schematic side elevational view of the distal end working unit according to the first structural example, with a trigger lever being in a non-operated state.

As shown in FIG. 22, the end of the wire 1056 in the Z1 direction is connected to both ends of the driven wire (a flexible member) 1252 by a terminal 1250 (or welding, through hole, etc.). The driven wire 1252 is in the form of a ring-like flexible member, having a portion thereof connected to the wire 1056, and may alternatively comprise a rope, a resin wire, a piano wire, a chain, or the like. The term "ring-shaped" should be interpreted in a broad sense. The flexible member does not necessarily need to be applied to the entire length. That is, at least the portion of the driven wire 1252, which is wound around each of the pulleys, may be a flexible member with the linear portion thereof being connected by a rigid member. The driven wire 1252 may make up part of the wire 1056.

The driven wire 1252 passes from the wire 1056, serving as a drive member, along the idle pulley 1140 in the X1 direction (first side) and extends to the X2 direction (second side), and then passes along the guide pulley 1142 in the X2 direction and extends to the surface of the driven pulley 1156 in the X2 direction. The driven wire 1252 is then wound in a half turn around the surface of the driven pulley 1156 in the Z1 direction and extends to the surface thereof in the X1 direction, and while oriented in the X2 direction, the driven wire 1252 passes along the idle pulley 1140 in the X2 direction and extends to the terminal 1250.

The driven wire 1252 thus passes through a circulatory path, having its starting and ending points at the terminal 1250. The driven wire 1252 passes along both sides of the idle pulley 1140 and is wound around the driven pulley 1156, while crossing over itself between the idle pulley 1140 and the guide pulley 1142, thereby making up a substantially 8-shaped configuration. The terminal 1250 and the driven wire 1252 are mechanically connected to the trigger lever 1032 by the wire 1056.

The term "mechanically" refers to a system for actuating members via a mechanical component, in the form of a solid body that is nonelastic in the power transmitting direction. Although the wire 1056 is a flexible member, it is appropriately tensioned by the spring 1150. For closing the end effector 1104, the wire 1056 is pulled in the Z2 direction by the trigger lever 1032 and essentially is not elastically deformed, or inevitably is elastically deformed only to an extent that is trouble-free in operation, thereby providing a mechanical connecting means. The driven wire 1252 crosses over itself as viewed in plan.

The idle pulley 1140, the guide pulley 1142, and the driven pulley 1156 have substantially the same diameter, which is a sufficiently large diameter, to the extent possible by the layout, such that the driven wire 1252 will not become bent. The terminal 1250 is disposed in a position appropriately spaced from the idle pulley 1140, so that the driven wire 1252 will not be bent excessively. Both ends of the driven wire 1252 form an acute angle at the terminal 1250. Since the spring 1150 (see FIG. 18) biases the driven plate 1158 to move in the Z1 direction, the driven pulley 1156 and the driven plate 1158 undergo forces in the Z1 direction. The driven wire 1252 and the wire 1056 are thus placed appropriately in a state of tension, and are not slackened. The gap between the idle pulley 1140 and the guide pulley 1142 is small, e.g., substantially the same as the width of the driven wire 1252.

The idle pulley 1140, the guide pulley 1142, and the driven pulley 1156 may have flanges on upper and lower surfaces thereof, or may have concave side surfaces for preventing the driven wire 1252 from dropping off.

For illustrative purposes, the wire 1056, the driven wire 1252, the idle pulley 1140, the guide pulley 1142, the driven pulley 1156, and the end effector 1104, shall be referred to collectively as an end effector driving mechanism 1260. In the end effector driving mechanism 1260, as shown in FIG. 22, the driven wire 1252, the idle pulley 1140, the guide pulley 1142, and the driven pulley 1156 are arranged along the central line from a proximal end to a distal end. The end effector 1104 is coupled to the driven pulley 1156 by the rod 1152.

Operation of the medical manipulator 1010 thus constructed shall be described below.

As shown in FIG. 22, when the trigger lever 1032 is not touched, the end effector 1104 is opened under the resiliency of the spring 1150. The X direction in FIGS. 22, 23, 24, 25, 36, 37, 52, 53, and 55 is indicated with respect to the distal end working unit 1012a, and the vertical direction of the trigger lever 1032 corresponds to the Y directions.

Figure 23:
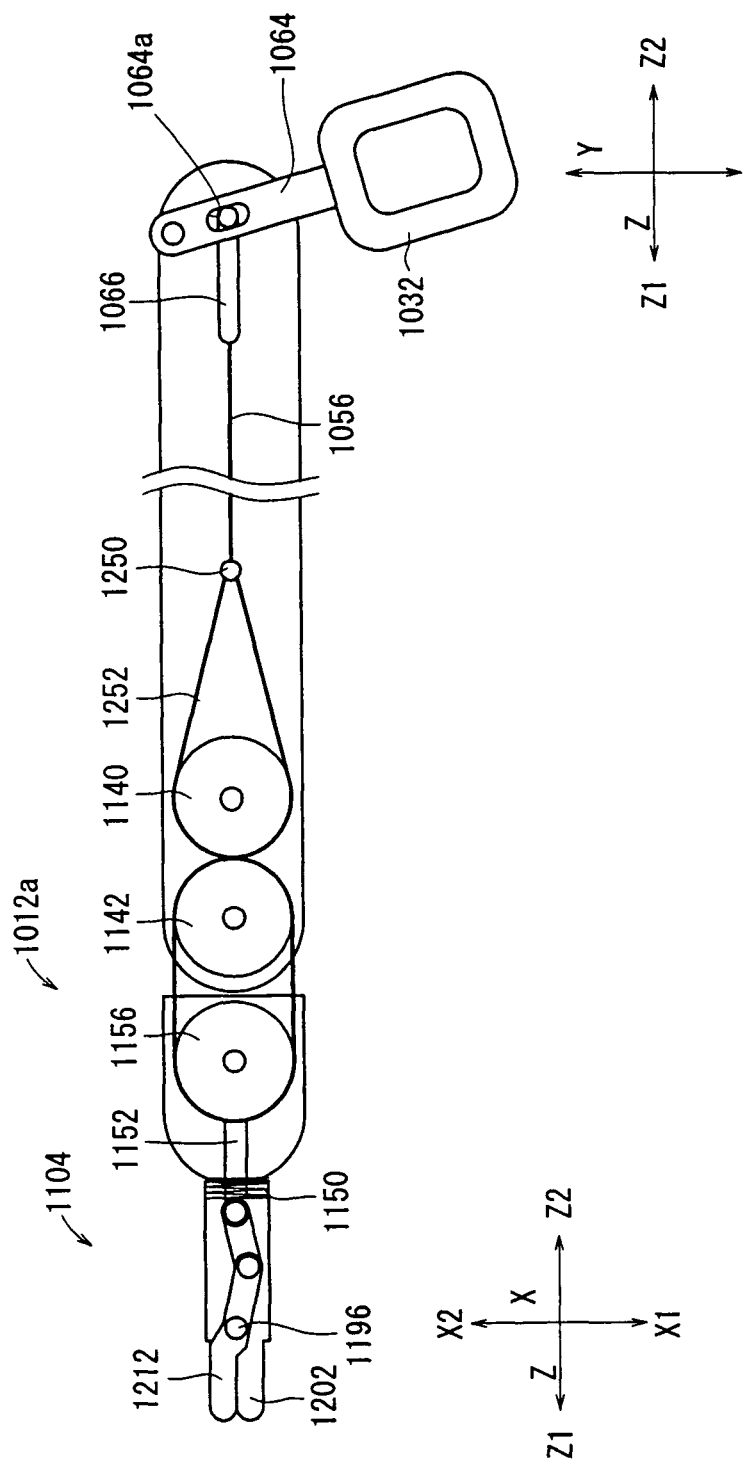
FIG. 23 is a schematic side elevational view of the distal end working unit according to the first structural example, with the trigger lever being fully pulled.

As shown in FIG. 23, when the trigger lever 1032 is fully pulled by hand, the wire 1056 pulls the driven wire 1252, moving the driven pulley 1156 and the rod 1152 in the Z2 direction while compressing the spring 1150, thereby closing the end effector 1104. In other words, the end effector 1104 is closed when the transmitting members, including the wire 1056, the driven wire 1252, and the driven pulley 1156, are pulled. At this time, the trigger lever 1032 requires forces for compressing the spring 1150. For opening the end effector 1104, the force applied to the trigger lever 1032 is released, thereby allowing the rod 1152 to be pushed toward the distal end under the restorative force of the spring 1150, and returning the end effector 1104 to the open state.

Since the driven wire 1252 is ring-shaped, it provides two left and right stretches. Therefore, the forces applied to close the end effector 1104 are divided into substantially equal forces, which act as tensile forces on respective stretches of the driven wire 1252. Therefore, the driven wire 1252 may have a diameter that is smaller than the wire 1056, and may be sufficiently flexible.

Figure 24:
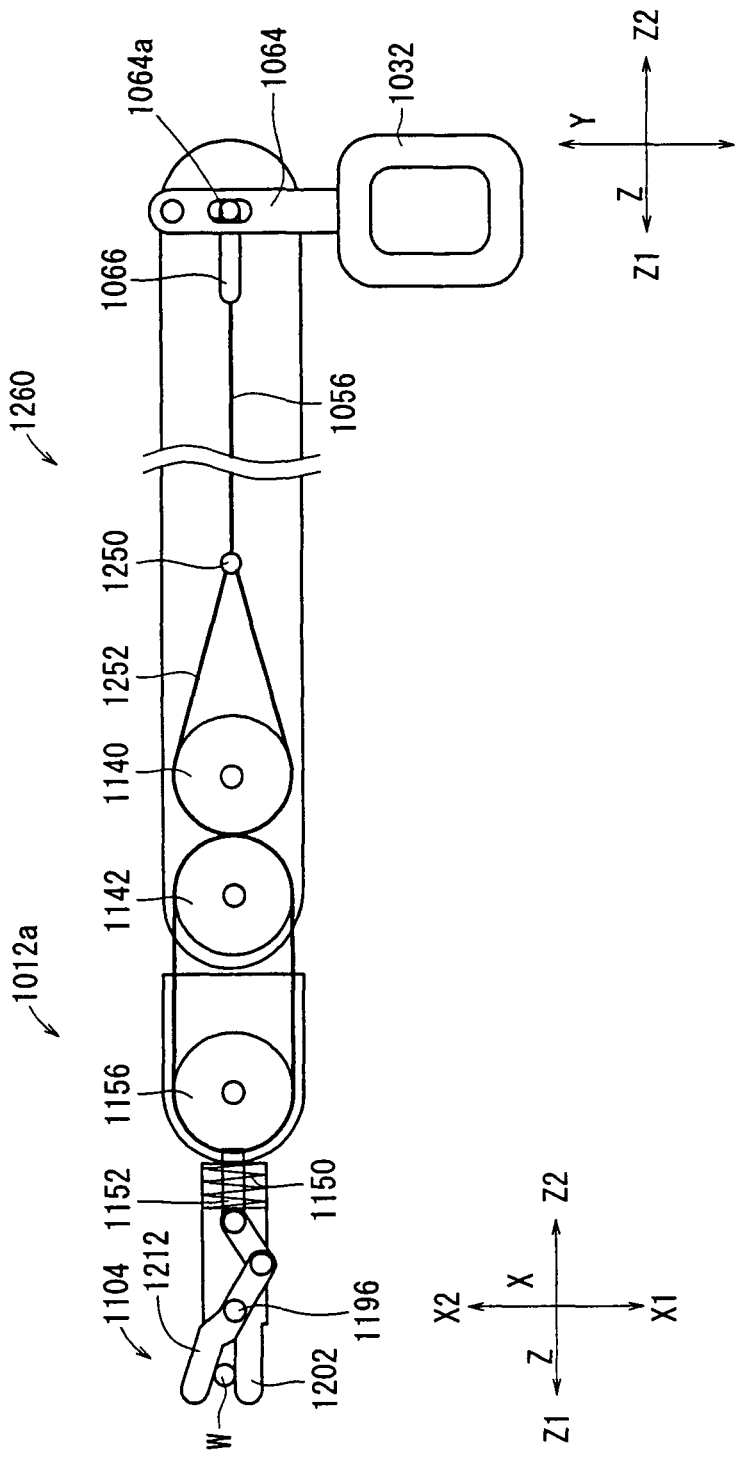
FIG. 24 is a schematic side elevational view of the distal end working unit according to the first structural example, with the trigger lever being pulled to an intermediate position.

As shown in FIG. 24, when the end effector 1104 grips an object (a surgical instrument, a living tissue, or the like) W at the time the trigger lever 1032 is pulled to a certain extent by the hand, the end effector 1104, the driven plate 1158, the rod 1152, and the driven pulley 1156 are essentially no longer moved further, or are moved only a distance corresponding to the elastic deformation of the driven wire 1252 and other components and the elastic deformation of the object W. The driven wire 1252, the wire 1056, and the trigger lever 1032 are not moved further in the Z2 direction, thereby allowing the operator to feel, with the fingertip, that the end effector 1104 has gripped the object W.

If the object W is a hard object such as a surgical instrument or the like, then the trigger lever 1032 is essentially unable to move in the Z2 direction. The operator can thus feel that the end effector 1104 has gripped something hard, and the end effector 1104 can reliably grip the object W with strong forces, because the operator can transmit manual forces mechanically and directly to the end effector 1104, rather than via electromagnetic means. If gripping forces equivalent to such manual forces were to be generated by a motor, then the motor would need to be considerably large and heavy, and could not be housed readily inside the actuator block 1030, and further, would make the medical manipulator 1010 heavier.

If the object W is a soft object such as a living tissue or the like, then the trigger lever 1032 is slightly displaceable in the Z2 direction depending on the resiliency of the object W. The operator can thus feel that the end effector 1104 has gripped something soft, and can recognize how soft the object W is as well as adjust the forces with which the object W is gripped.

When the wires, etc., are worn or become degraded, friction increases and is transmitted to the trigger lever 1032, allowing the operator to sense a change in state, or an abnormal state, of the drive system. Hence, the operator can judge the timing of maintenance more appropriately.

Figure 25:
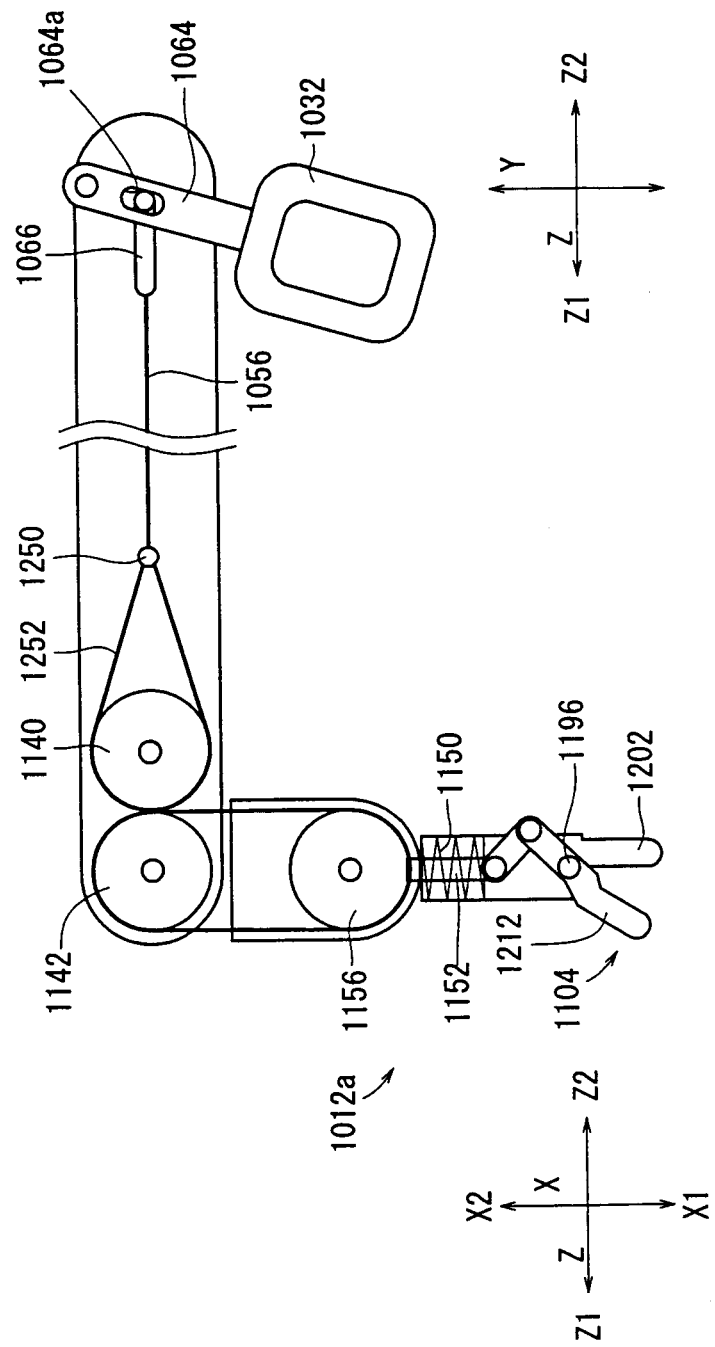
FIG. 25 is a schematic side elevational view of the distal end working unit according to the first structural example, with a roll axis being operated in one direction.

As shown in FIG. 25, when the end effector 1104 is operated about the yaw axis, the driven pulley 1156 rotates about itself, while revolving around the guide pulley 1142. Since the distance between the driven pulley 1156 and the guide pulley 1142 remains unchanged, the rod 1152 is not relatively actuated and there is no mechanical interference. When the end effector 1104 is operated about the roll axis, since the rod 1152 is disposed so as to pass through the center of the roll axis, the rod 1152 is not actuated and there is no mechanical interference. In other words, the effector driving mechanism 1260 provides a non-interfering construction.

Since the idle pulley 1140 and the guide pulley 1142 are sufficiently close to each other, even when the end effector 1104 is actuated 90° about the yaw axis, the angle through which the driven wire 1252 is wound around the driven pulley 1156 remains essentially unchanged, and substantially no torque that interferes with the yaw and roll axes is generated in response to the gripping action.

If the idle pulley 1140 and the guide pulley 1142 are spaced from each other by a certain distance, then when the end effector 1104 is operated significantly about the roll axis, the driven wire 1252 is spaced from one of the surfaces of the guide pulley 1142. The driven wire 1252 is thus brought out of balance in the X direction (reference state) about the yaw axis, producing an interference torque about the yaw axis. For maximizing the operating range about the yaw axis, it is desirable to position the idle pulley 1140 and the guide pulley 1142 sufficiently close to each other. Actually, inasmuch as the driven wire 1252 passes between the idle pulley 1140 and the guide pulley 1142, a certain gap is needed therebetween. Also, the gap between portions of those pulleys (except for the flanges on the upper and lower surfaces) around which the driven wire 1252 is wound may be of a size that is 1 to 2 times the thickness of the driven wire 1252.

If the operating range about the yaw axis does not need to be increased, then the idle pulley 1140 and the guide pulley 1142 may be appropriately spaced from each other. Even if the yaw axis is bent, the end effector 1104 can be opened and closed by operating the trigger lever 1032, so as to cause the driven wire 1252 to actuate the driven pulley 1156.

As the yaw-axis operation and the roll-axis operation do not cause mechanical interference with opening and closing operations of the end effector 1104, the drive mechanism of the distal end working unit 1012a for actuating the end effector 1104 does not require any correcting means for compensating for interference, or any other type of correcting means (e.g., corrective actuators and assisting mechanisms) including mechanisms and actuators. Therefore, the medical manipulator 1010 is simple and lightweight in structure. Operating forces applied to the trigger lever 1032 can efficiently be transmitted to the end effector 1104 without affecting other drive systems. Consequently, the end effector 1104 can exert strong gripping (or peeling) forces. Inasmuch as the medical manipulator 1010 is lightweight, the operator can reduce the forces needed to support the medical manipulator 1010. As a result, the medical manipulator 1010 enables the operator to perform techniques suitably over a long period of time, and also to better feel the forces at which tissue is pierced with a suture needle, along with reactive forces from the tissue.

The medical manipulator 1010 is an energy saver because the end effector 1104 can be opened and closed manually by the trigger lever 1032.

A link mechanism, which is a reversal of the above link mechanism, may be used, such that the end effector 1104 is closed when it is not operated on by the hand. In this case, the end effector 1104 can be opened when the trigger lever 1032 is pulled. The reversal link mechanism may be such that the closed state of the end effector 1104, i.e., the state in which the second gripper 1212 is superposed on the first gripper 1202, as shown in FIG. 22 for example, is an initial state. When the trigger lever 1032 is pulled in the initial state, the second gripper 1212 is turned counterclockwise and spaced from the first gripper 1202, thereby opening the end effector 1104.

During surgical operations, a large peeling force may be required in a direction (peeling direction) to open the end effector 1104, for the purpose of peeling off tissue. If the pulling action of the trigger lever 1032 is directly transmitted to the end effector 1104 through the reversal link structure, then a large peeling force can be produced.

In this case, with the medical manipulator 1010, the forces in the opening direction of the end effector 1104 are transmitted to the trigger lever 1032. In other words, when the end effector 1104 is opened and abuts against living tissue, a surgical instrument, or the like, in the opening direction, the trigger lever 1032 is unable to move in the Z1 direction. The operator thus can sense that the end effector 1104 abuts against something.

Since the difference between the yaw axis and the pitch axis of the distal end working unit 1012 represents an initial attitude or a relative attitude with respect to the operating unit, the yaw axis may be replaced with the pitch axis. Therefore, the distal end working unit 1012 may have the yaw axis and the pitch axis. The attitude axes (corresponding to the yaw axis and the roll axis on the distal end working unit 1012) may be actuated by rods, links, torque tubes, or the like, for example, or any combination thereof, rather than by means of wires (flexible members) and gears.

The idle pulley 1140, the guide pulley 1142, and the driven pulley 1156 may not necessarily be pulleys, but may comprise cylindrical bodies (cylindrical members) around which wires can be wound, if they allow the flexible member to slip thereon. The cylindrical bodies are to be interpreted in a broad sense, and include hollow cylindrical bodies and arcuate columnar bodies. If the angle of the operational range of a pulley is small according to design conditions, then the wire may be wound in less than one turn around the pulley. In this case, the pulley may be an arcuate columnar body.

If the driven pulley 1156 is nonrotatable with respect to the pin 1154 (the driven pulley 1156 is fixed to the rod 1152), then since the driven wire 1252 is not held in abutment against a semiarcuate portion of the driven pulley 1156 that is closer to the guide pulley (in the Z2 direction), the semiarcuate portion of the driven pulley 1156 is not required, and hence the driven pulley 1156 may be in the form of a cylindrical body, having only a semiarcuate portion closer to the distal end thereof. If a return pulley 1350, similarly, has a portion held out of abutment against the driven wire 1252, then the return pulley 1350 may be a partly arcuate cylindrical body, thereby enabling the composite mechanism 1102 to be reduced in length.

Modifications of the junction at the end of the driven wire 1252, which correspond to the terminal 1250, shall be described below with reference to FIGS. 26 to 31.

Figure 26:
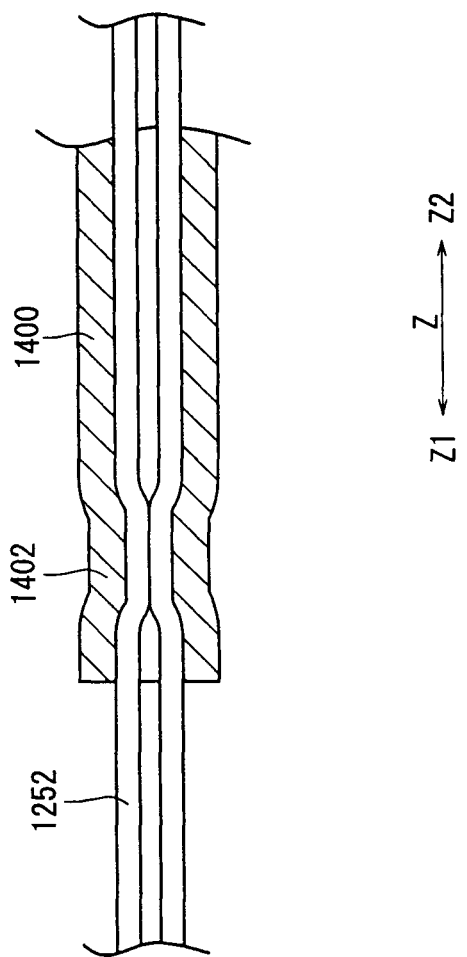
FIG. 26 is a schematic view of a connected portion of an end of a passive wire according to a first modification.

According to a first modification of the function at the end of the driven wire 1252, as shown in FIG. 26, both ends of the driven wire 1252 are inserted into the opening at the distal end of a pipe (driving member) 1400, and a portion 1402 proximate the opening at the distal end is pressed so as to compress the inserted ends. The driven wire 1252 can thus be secured in place easily.

Figure 27:
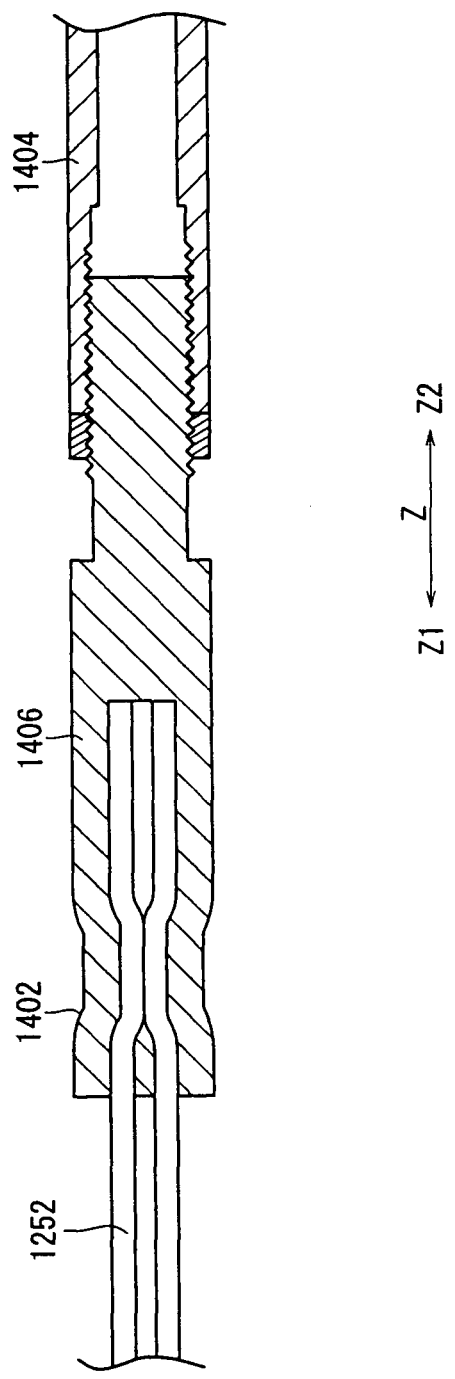
FIG. 27 is a schematic view of a connected portion of an end of a passive wire according to a second modification.

According to a second modification of the function at the end of the driven wire 1252, as shown in FIG. 27, a pipe 1406 is threaded into the distal end of a rod (driving member) 1404. Similar to the pipe 1400 shown in FIG. 26, the pipe 1406 compresses both ends of the driven wire 1252. Thus, with this arrangement, the rod 1404 and the pipe 1406 are detachably connected to each other, for facilitating assembly and maintenance. Such threaded engagement allows the pipe 1406 to project adjustably from the rod 1404, for adjusting the length and tension of the driven wire 1252. The pipe 1406 may further be secured by a double-nut structure.

Figure 28:
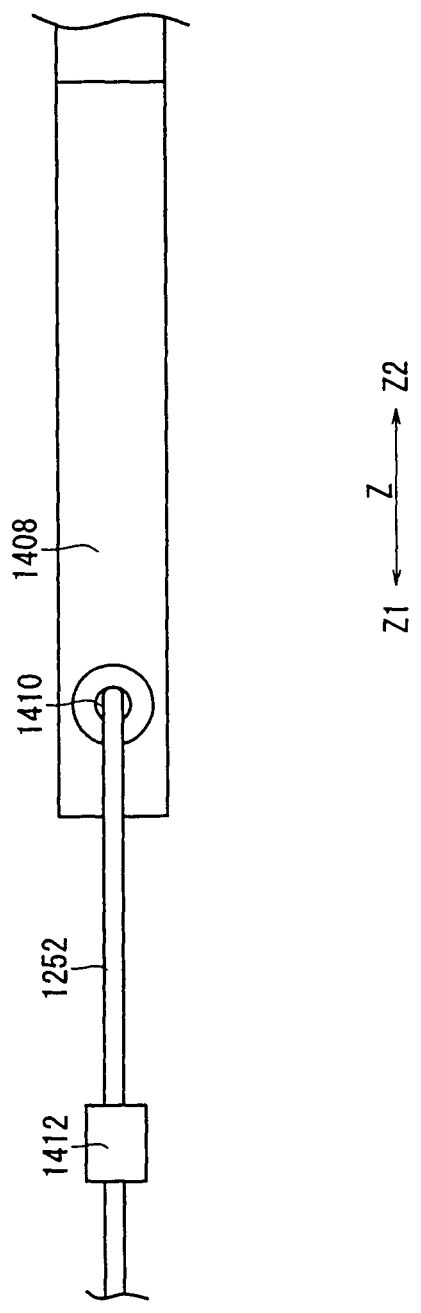
FIG. 28 is a schematic plan view of a connected portion of an end of a passive wire according to a third modification.
Figure 29:
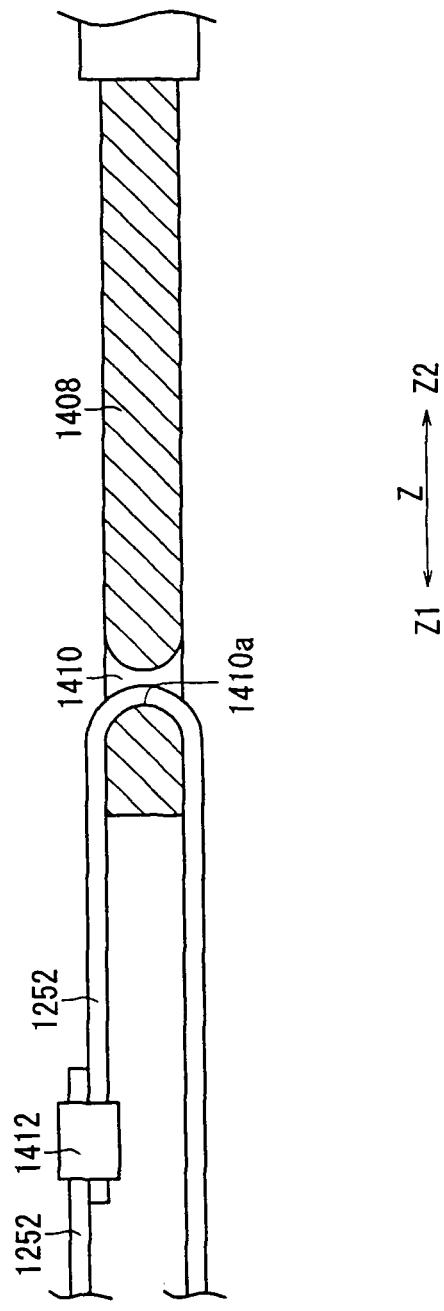
FIG. 29 is a schematic sectional side elevational view of the connected portion of the end of the passive wire according to the third modification.

According to a third modification of the function at the end of the driven wire 1252, as shown in FIGS. 28 and 29, the driven wire 1252 is inserted through a hole 1410 formed in the distal end of a rod (driving member) 1408. The hole 1410 has an arcuate wall 1410*a* facing in the Z2 direction, which is engaged by the driven wire 1252. The driven wire 1252 slides against the arcuate wall 1410*a*. When the rod 1408 is pulled in the Z2 direction, the driven wire 1252 can be pulled in the X direction with good balance.

The driven wire 1252, which comprises a single wire, has both ends thereof fixed to a securing member 1412, and hence is of a ring shape. The securing member 1412 is disposed in a location other than the junction to the rod 1408 as a driving member, and allows the length and tension of the driven wire 1252 to be adjusted. Hence, the third modification is simple in structure.

Figure 30:
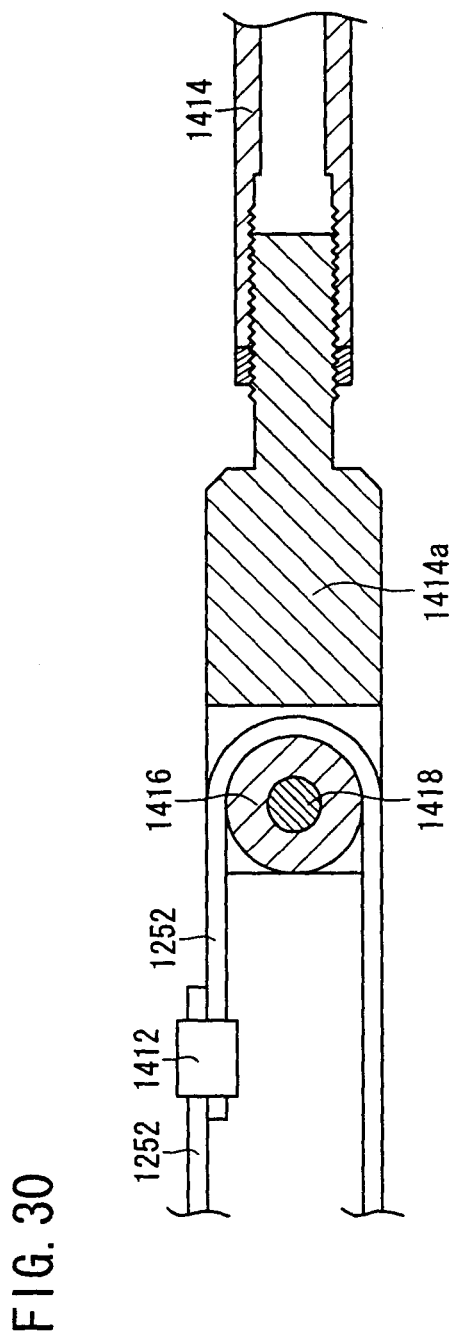
FIG. 30 is a schematic sectional plan view of a connected portion of an end of a passive wire according to a fourth modification.
Figure 31:
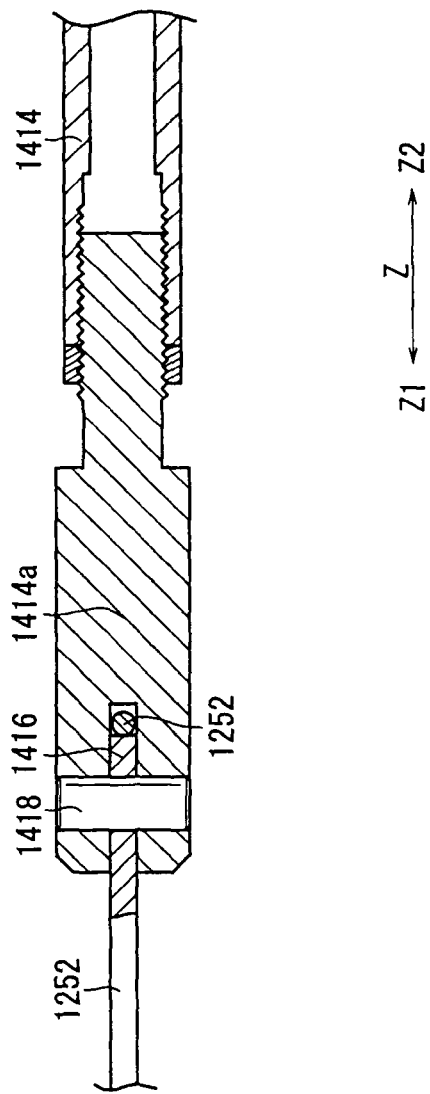
FIG. 31 is a schematic sectional side elevational view of the connected portion of the end of the passive wire according to the fourth modification.

According to a fourth modification of the function at the end of the driven wire 1252, as shown in FIGS. 30 and 31, a roller 1416 is mounted at a distal end portion 1414*a* of a rod (driving member) 1414, and the driven wire 1252 is wound around the roller 1416. The roller 1416 is rotatably supported on a pin 1418. The driven wire 1252, as it is wound around the roller 1416, is movable back and forth. When the rod 1414 is pulled in the Z2 direction, the driven wire 1252 can be pulled in the X direction with good balance, even if the yaw axis is not bent. The distal end portion 1414*a* is threaded into the rod 1414. According to the fourth modification, the paired stretches of the driven wire 1252, which are spaced in the Y direction, are tensioned uniformly so as to lengthen the service life of the driven wire 1252 and to make the paired upper and lower stretches of the driven wire 1252 parallel to each other.

Since the paired stretches of the driven wire 1252, which are spaced in the Y direction, are parallel to each other, the rod 1414 may be disposed in a position close to the distal end working unit 1012*a*, thereby shortening the driven wire 1252 and reducing elongation of the driven wire 1252, so as to increase the responsiveness thereof.

A distal end working unit 1012*b* according to a second structural example will be described below. Those parts of the distal end working unit 1012*b* (as well as the distal end working units 1012*c* through 1012*f*) that are identical to those of the distal end working unit 1012*a* shall be denoted by identical reference characters, and these features will not be described in detail below.

Figure 32:
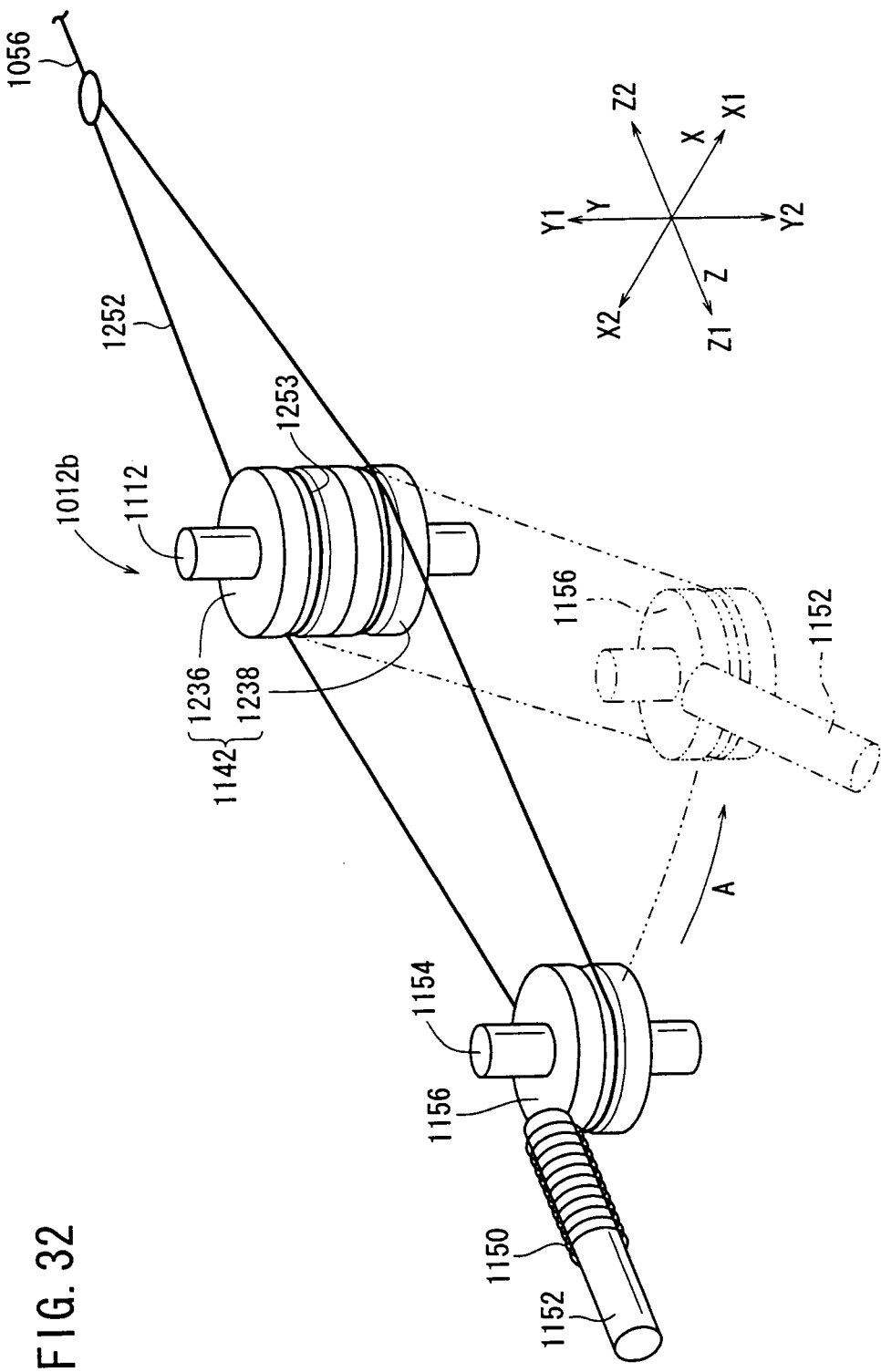
FIG. 32 is a schematic structural view of a distal end working unit according to a second structural example.

As shown in FIG. 32, the distal end working unit 1012*b* is of a structure that is similar to the distal end working unit 1012*a*, except that the idle pulley 1140 (see FIG. 21) is dispensed with. In the distal end working unit 1012*b*, the driven wire 1252 is wound in one turn or more around the guide pulley 1142 from two directions. Specifically, the driven wire 1252 is wound around the first layer guide pulley 1236 from the X2 direction, and is wound around the second layer guide pulley 1238 from the X1 direction. The distal end working unit 1012b operates in the same manner as the distal end working unit 1012a. When the driven wire 1252 is pulled in the Z2 direction, the guide pulley 1142 and the driven pulley 1156 are pulled to operate the end effector 1104, and also to operate the end effector 1104 in the yawing directions, about the shaft 1112 (see the imaginary lines in FIG. 32). If the operation range about the yaw axis is one-sided (0° to 90°), then only one stretch of the driven wire 1252 may be wound in one turn or more around the guide pulley 1142. For example, in FIG. 32, in order to operate the end effector 1104 only in one direction, as indicated by the arrow A, about the yaw axis, the turn 1253 of the driven wire 1252, which is wound around the first layer guide pulley 1236 in the X1 direction, is not required. The driven wire 1252 may be held only against the surface of the first layer guide pulley 1236, which faces in the X2 direction.

The distal end working unit 1012b is simpler in structure than the distal end working unit 1012a, because it does not require the idle pulley 1140. On the other hand, with the distal end working unit 1012a, the length of the driven wire 1252, which is wound around the guide pulley 1142, is shorter for providing less friction, and the overall length of the driven wire 1252 is shorter than in the case of the distal end working unit 1012b. Since the number of turns around the guide pulley 1142 is smaller, the guide pulley 1142 may be thinner. Whether the distal end working unit 1012a or the distal end working unit 1012b is to be employed may be determined depending on design conditions.

The structures shown in FIGS. 26 to 32 are also applicable to the distal end working units 1012c through 1012f, to be described below.

The distal end working unit 1012c according to a third structural example will be described below.

Figure 33:
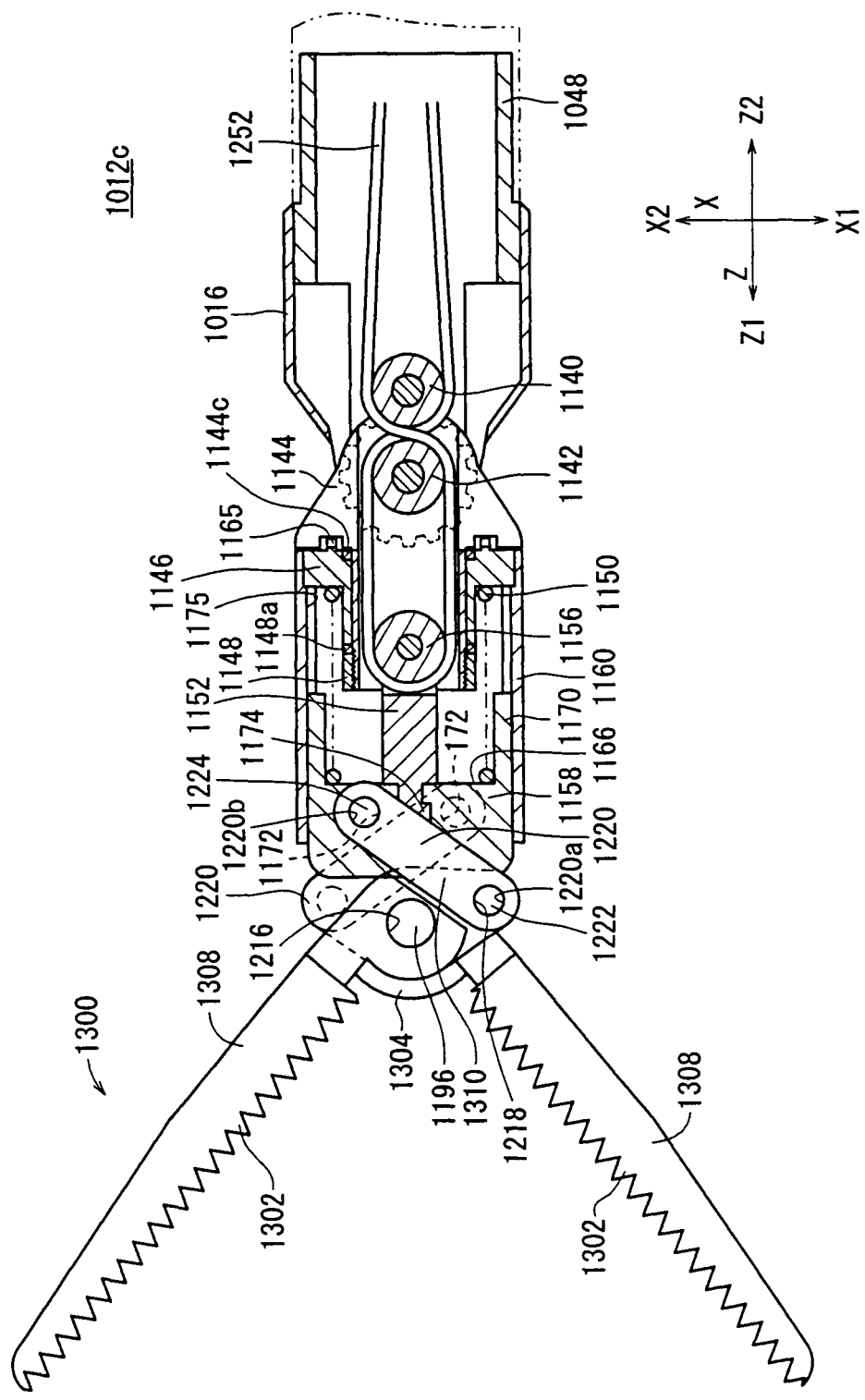
FIG. 33 is a sectional side elevational view of a distal end working unit according to a third structural example.

As shown in FIG. 33, the distal end working unit 1012c is different from the distal end working unit 1012a in terms of the structure of the end effector 1104.

The distal end working unit 1012c includes an end effector 1300 having a double-sided-open type structure, with a pair of grippers 1302 being movable thereon. The end effector 1300 comprises a gripper base 1304 integrally combined with the cover 1160, a pair of end effector members 1308 movable about a pin 1196 mounted on the gripper base 1304, and a pair of gripper links 1220.

Each of the end effector members 1308 has an L shape, similar to the second end effector member 1192, and comprises a gripper 1302 extending in the Z1 direction and a lever 1310 bent about 35° and extending from the gripper 1302. The L-shaped bent corner includes a hole 1216 formed therein, and the pin 1196 is inserted into the hole 1216, so that the end effector members 1308 are swingable about the third rotational axis Og.

Each of the end effector members 1308 is coupled to a pin 1224 on the driven plate 1158 by a single side gripper link 1220. The driven plate 1158 has two link holes 1172 disposed in symmetrical positions with respect to the Y direction in FIG. 33. The gripper links 1220 cross each other, as viewed in side elevation.

The wire-driven mechanism 1100 and the composite mechanism 1102, other than the end effector 1300 of the distal end working unit 1012c, are identical in structure to those of the distal end working unit 1012a described above.

Since the grippers 1302 are disposed in confronting positions, the distal end working unit 1012c is capable of exerting well-balanced forces, without imposing inadvertent moment loads.

Figure 34:
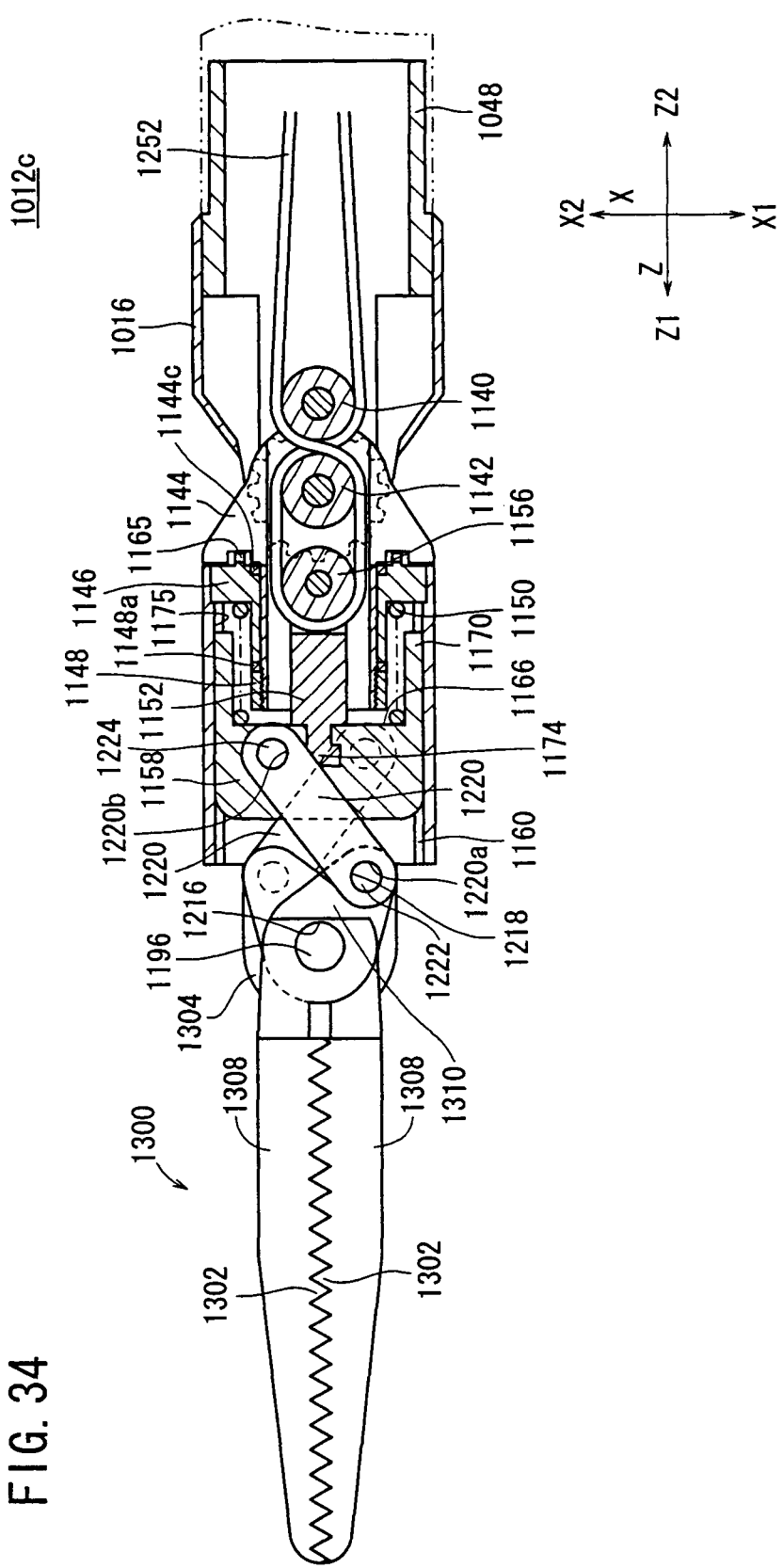
FIG. 34 is a sectional side elevational view of the distal end working unit according to the third structural example, with a gripper being closed.

As shown in FIGS. 33 and 34, the end effector members 1308 are basically actuated in synchronism in response to operation of the rod 1152. Therefore, the end effector members 1308 are openable and closable symmetrically with respect to the central axis.

Figure 35:
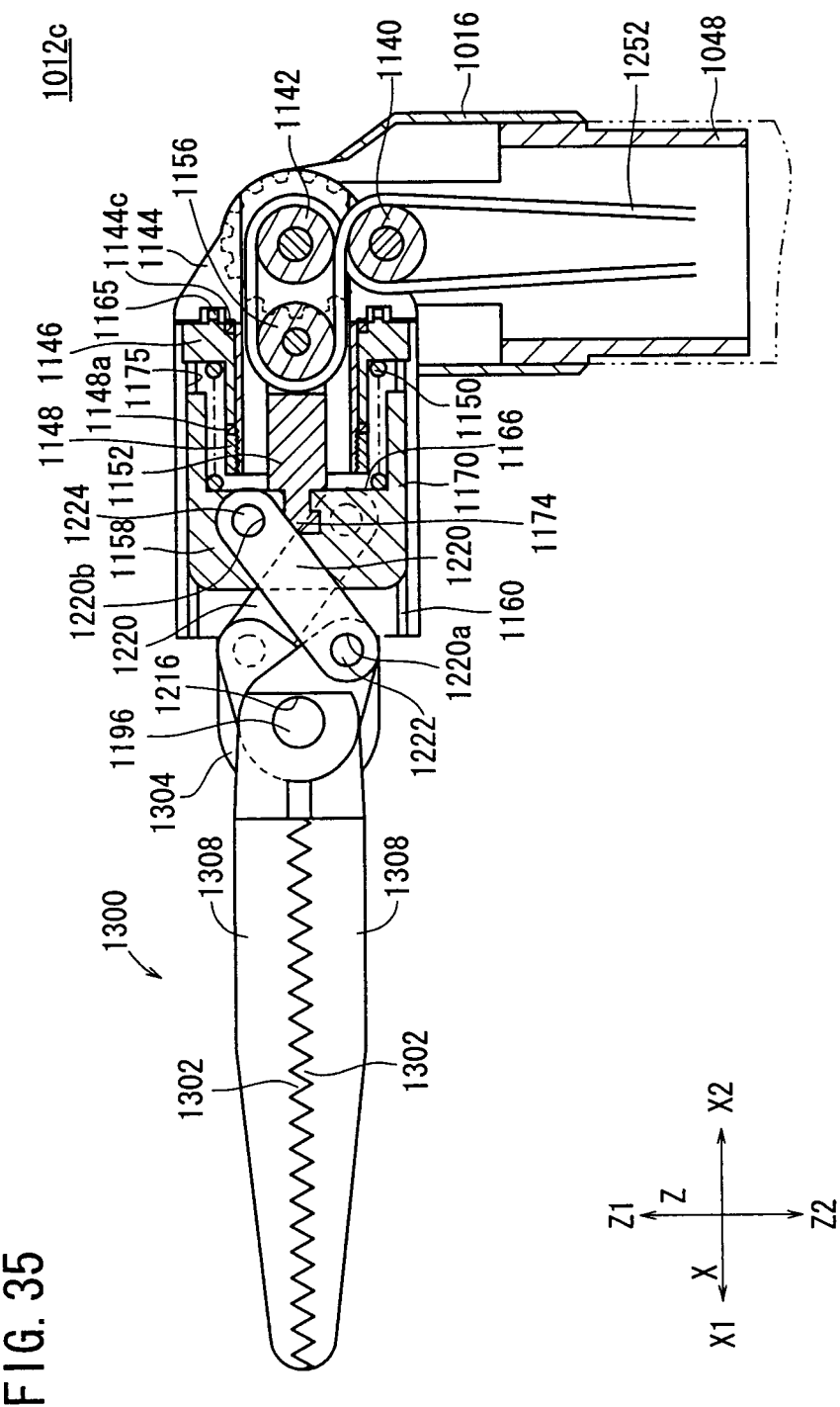
FIG. 35 is a schematic side elevational view of the distal end working unit according to the third structural example, with a roll axis being operated in one direction.

As shown in FIG. 35, when the end effector 1300 moves about the yaw axis, since the yaw-axis mechanism and the mechanism for actuating the end effector 1300 are held out of interference with each other, the degree of opening of the end effector 1300 does not change. Conversely, when the end effector 1300 is opened and closed, the end effector 1300 does not move about the yaw axis or the roll axis.

Since the end effector 1300 is mechanically connected directly to the trigger lever 1032, the end effector 1300 produces strong gripping forces, wherein the forces applied to the end effector 1300 are transmitted to the trigger lever 1032.

The distal end working unit 1012d according to a fourth structural example will be described below. With the distal end working units 1012a through 1012c described above, the trigger lever 1032 is pulled actively (i.e., the grippers are closed/opened) by a manual force, and the trigger lever 1032 is passively returned by the force of the spring 1150, so that the force is applied in one direction only for opening/closing the grippers. With the distal end working unit 1012d according to the fourth structural example (as well as with the distal end working unit 1012e), a manual force is applied actively to pull and return the trigger lever 1032, whereby a force is applied in both directions. The spring 1150 for generating forces is dispensed with. The distal end working unit 1012d may be used as a gripping forceps as well as a peeling forceps.

Figure 36:
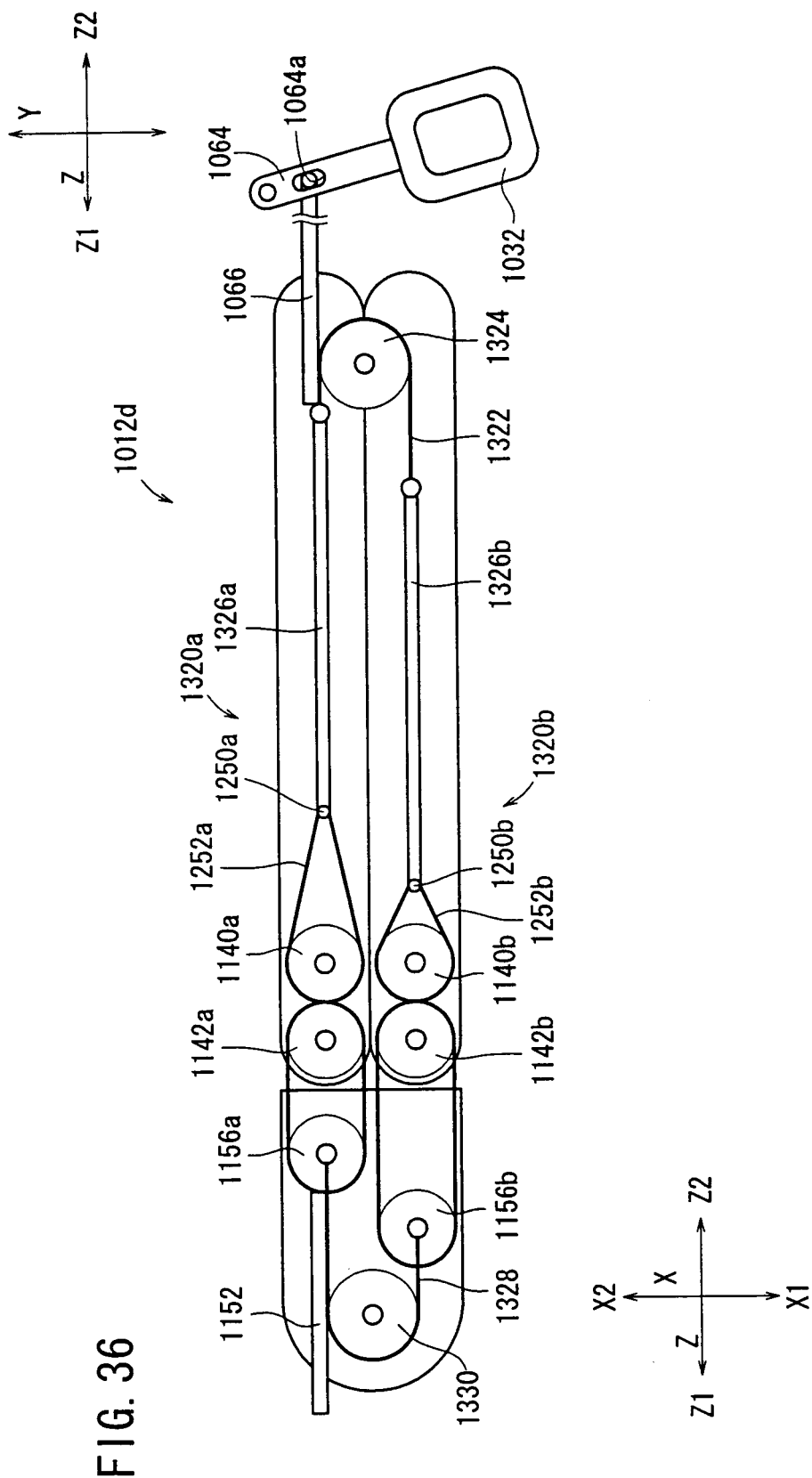
FIG. 36 is a schematic side elevational view of a distal end working unit according to a fourth structural example, with a trigger lever being pushed out.
Figure 37:
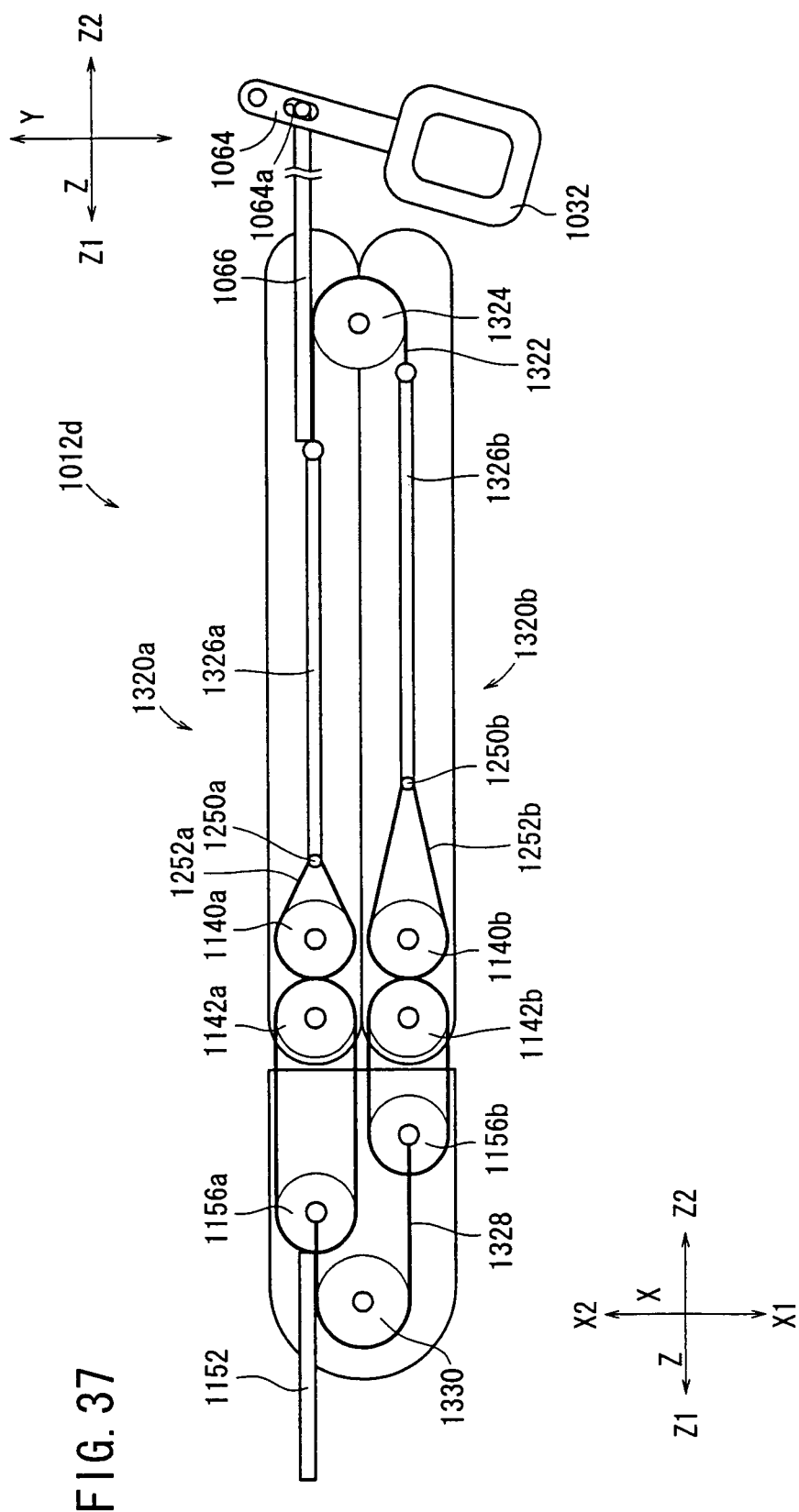
FIG. 37 is a schematic side elevational view of the distal end working unit according to the fourth structural example, with the trigger lever being fully pulled.
Figure 38:
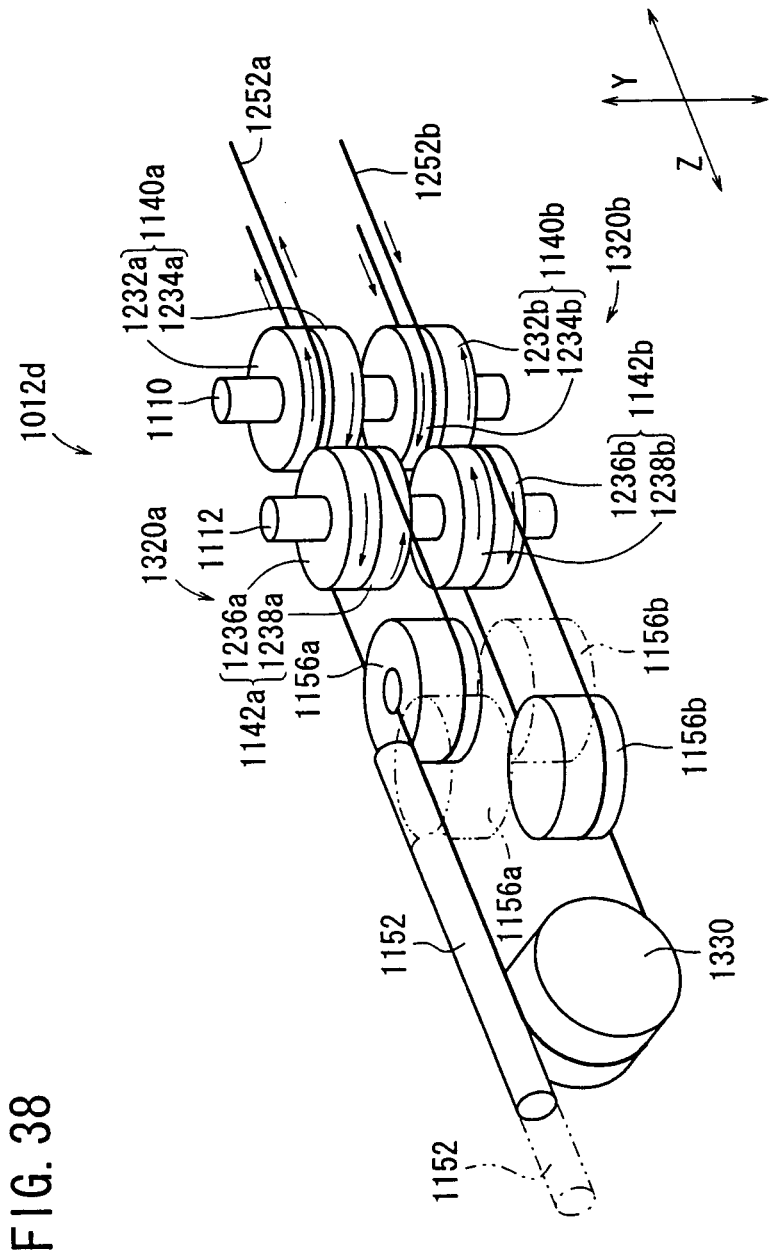
FIG. 38 is a schematic structural view of a distal end working unit according to a fourth structural example.

As shown in FIG. 36, the distal end working unit 1012d includes two mechanisms, i.e., a first end effector driving mechanism 1320a and a second end effector driving mechanism 1320b, corresponding to the end effector driving mechanism 1260 (see FIG. 22). Components of the first end effector driving mechanism 1320a are denoted by reference characters with an "a" appended thereto, and components of the second end effector driving mechanism 1320b are denoted by reference characters with a "b" appended thereto, so that they can be distinguished from each other. In FIGS. 36 and 37 (as well as FIGS. 52 and 53), the first end effector driving mechanism 1320a and the second end effector driving mechanism 1320b are shown in parallel with each other on the sheets, for facilitating understanding. If the distal end working unit 1012d is incorporated in an actual medical manipulator 1010, then, as shown in FIG. 38 (and FIG. 51), the pulleys are juxtaposed axially (i.e., in the Y direction) such that the rotational shafts of the idle pulleys (cylindrical members, transmitting members) 1140a, 1140b are disposed coaxially with each other, and the rotational shafts of the guide pulleys (cylindrical members, transmitting members) 1142a, 1142b also are disposed coaxially with each other. In other words, the idle pulleys 1140a, 1140b are supported commonly on the shaft 1110 (see FIG. 38), whereas the guide pulleys 1142a, 1142b are supported commonly on the shaft 1112. The guide pulleys 1142a, 1142b, which are coaxial with each other, simplify the yaw axis operating mechanism.

The distal end working unit 1012d comprises a first end effector driving mechanism 1320a, a second end effector driving mechanism 1320b, a drive coupling wire (a drive coupling flexible member, a transmitting member) 1322, and a drive coupling pulley (a cylindrical member, a transmitting member) 1324, around which the drive coupling wire 1322 is wound. With this arrangement, the first end effector driving mechanism 1320*a* and the second end effector driving mechanism 1320*b* can be operated in opposite phase, so as to move a drive link (a transmitting member) 1326*a* and a drive link (a transmitting member) 1326*b* easily in opposite directions.

Although not illustrated, the distal end working unit 1012*d* includes a wire-driven mechanism 1100, a composite mechanism 1102, and an end effector 1104, which are identical to those of the distal end working unit 1012*a*.

The drive coupling wire 1322 has one end thereof connected to the proximal end of the drive link 1326*a* of the first end effector driving mechanism 1320*a*, and the other end thereof connected to the proximal end of the drive link 1326*b* of the second end effector driving mechanism 1320*b*. The drive links 1326*a*, 1326*b* correspond to the wire 1056, and are connected to terminals 1250*a*, 1250*b* at respective ends of driven wires 1252*a*, 1252*b*. In the distal end working unit 1012*d*, the drive links 1326*a*, 1326*b* may be replaced with wires. In such a case, the drive coupling wire 1322 may have both ends thereof directly connected to the terminals 1250*a*, 1250*b*.

The second link 1066 (see FIG. 22) has one end connected to the drive link 1326*a*, which can be moved back and forth by the trigger lever 1032. Since the drive coupling wire 1322 and the drive link 1326*b* are connected to the drive link 1326*a* around the drive coupling pulley 1324, the drive link 1326*a* and the drive link 1326*b* are moved back and forth in opposite directions when the second link 1066 is moved back and forth.

The trigger lever 1032 can actuate the drive link 1326*a* and the drive link 1326*b* through a rack and pinion mechanism, which includes a rack mounted on the second link 1066, and a pinion mounted on the drive coupling pulley 1324. The drive coupling pulley 1324 may be disposed in the distal end working unit 1012*d* (i.e., on a distal end of the connector shaft 1048), or may be disposed in the operating unit 1014.

The distal end working unit 1012*d* also includes a driven coupling wire (a driven coupling flexible member, a transmitting member) 1328, having one end connected to a driven pulley (a flexible member, a transmitting member) 1156*a* of the first end effector driving mechanism 1320*a* and another end connected to a driven pulley (a flexible member, a transmitting member) 1156*b* of the second end effector driving mechanism 1320*b*, and a driven coupling pulley (a cylindrical member, a transmitting member) 1330 around which the driven coupling wire 1328 is wound. In this arrangement, the first end effector driving mechanism 1320*a* and the second end effector driving mechanism 1320*b* can be operated in opposite phase so as to move the rod 1152 back and forth.

Either one of the driven pulley 1156*a* and the driven pulley 1156*b* is rotatably held by the rod 1152. The rod 1152 may be fixed to a linear portion of the driven coupling wire 1328. The rod 1152 may also be connected to the driven coupling pulley 1330 by a rack and pinion mechanism. In other words, the rod 1152 may bring about back-and-forth movement of the driven pulleys 1156*a*, 1156*b* or the driven coupling wire 1328.

If the drive coupling wire 1322 and the driven coupling wire 1328 are placed under an initial tension of ON or higher, and are made free from sagging, various parts of the distal end working unit are prevented from having play, and the distal end working unit can grip the object with high responsiveness.

As shown in FIG. 36, when the trigger lever 1032 is fully pulled by the hand, the drive link 1326*a* pulls the driven wire 1252*a* in order to move the driven pulley 1156*a* and the rod 1152 in the Z2 direction, thereby closing the end effector 1104. In other words, the end effector 1104 is closed by pulling the transmitting members, including the drive link 1326*a*, the driven wire 1252*a*, and the driven pulley 1156*a*.

In the second end effective driving mechanism 1320*b*, since the drive link 1326*b* is disposed such that it is pushed outward, the drive link 1326*b* does not obstruct the operation of the rod 1152. Since the driven wire 1252*b* produces only tensile forces (i.e., the driven wire 1252*b* does not transmit compressive forces), the driven wire 1252*b* basically does not contribute to the transmission of power.

At this time, when the end effector 1104 grips the object W, the driven wire 1252, the drive link 1326, and the trigger lever 1032 are unable to move further in the Z2 direction, thereby allowing the operator to feel, with the fingertip, that the end effector 1104 has gripped the object W. The operator also can sense the hardness of the object W. These actions can easily be understood by referring to FIGS. 36 and 24, because the distal end working unit 1012*a*, as shown in FIG. 24, is essentially equivalent to the distal end working unit 1012*d* shown in FIG. 36, although the second end effector driving mechanism 1320*b* is dispensed with.

As shown in FIG. 37, when the trigger lever 1032 is fully pushed out by the hand, the drive coupling wire 1322 is moved counterclockwise in FIG. 37, and the drive link 1326*b* pulls the driven wire 1252*b* in order to move the driven pulley 1156*b* in the Z2 direction. The driven coupling wire 1328 moves in a counterclockwise direction, and the rod 1152 and the driven pulley 1156*a* move in the Z1 direction toward the distal end, thereby opening the end effector 1104.

Since the forces for pushing out the trigger lever 1032 by hand are mechanically and directly transmitted to the end effector 1104 by the second end effector driving mechanism 1320*b*, the end effector 1104 can be opened with a desired strong force, rather than given forces such as from an elastic body. Therefore, using an outer side surface of the end effector 1104, the distal end working unit can appropriately be used to perform techniques for peeling off living tissue or for opening a hole.

When the object W is brought into contact with the outer side surface of the end effector 1104, the driven wire 1252*b*, the drive link 1326*b*, and the trigger lever 1032 are no longer moved further in the Z1 direction, thereby allowing the operator to feel, with the fingertip, that the outer side surface of the end effector 1104 has contacted the object W. The operator also can sense the hardness of the object W.

The distal end working unit 1012*d* can operate about the yaw axis and the roll axis, in the same manner as the distal end working unit 1012*a*. Although not shown, when the distal end working unit 1012*d* operates about the yaw axis, the composite mechanism 1102 and the end effector 1104, which are closer to the distal end than the shafts (see FIG. 38) of the guide pulleys 1142*a* and 1042*b*, swing in yawing directions about the shafts of the guide pulleys 1142*a* and 1042*b*. Since the distal end working unit 1012*d* makes up a non-interference mechanism, similar to the distal end working unit 1012*a*, when the distal end working unit 1012*d* operates about the yaw axis, the degree at which the end effector 1104 is opened remains unchanged. Conversely, when the degree of opening of the end effector 1104 is changed, the yaw axis is not operated. The end effector 1104 and the roll axis are related to each other in the same manner.

The distal end working unit 1012*d* (as well as the distal end working unit 1012*e*) does not require the spring 1150. Depending on design conditions, the spring 1150 may be provided to bias the rod 1152 to move toward either the distal end or the proximal end. This arrangement makes it possible to hold the end effector open or closed when the trigger lever 1032 is not operated. If sufficient space is not available in the distal end working unit 1012*d*, then the spring 1150 may also be disposed in the trigger lever 1032.

As shown in FIG. 38, in the distal end working unit 1012*d*, the idle pulleys 1140*a*, 1140*b* have respective outer first layer idle pulleys 1232*a*, 1232*b*, which are coaxial with each other, and respective inner second layer idle pulleys 1234*a*, 1234*b*, which also are coaxial with each other. The guide pulleys 1142*a*, 1142*b* have respective outer first layer guide pulleys 1236*a*, 1236*b*, which are coaxial with each other, and respective inner second layer guide pulleys 1238*a*, 1238*b*, which also are coaxial with each other. This structure is similar to the structure shown in FIG. 21, allowing the paired pulleys to rotate in opposite directions for enabling smooth operation.

Figure 39:
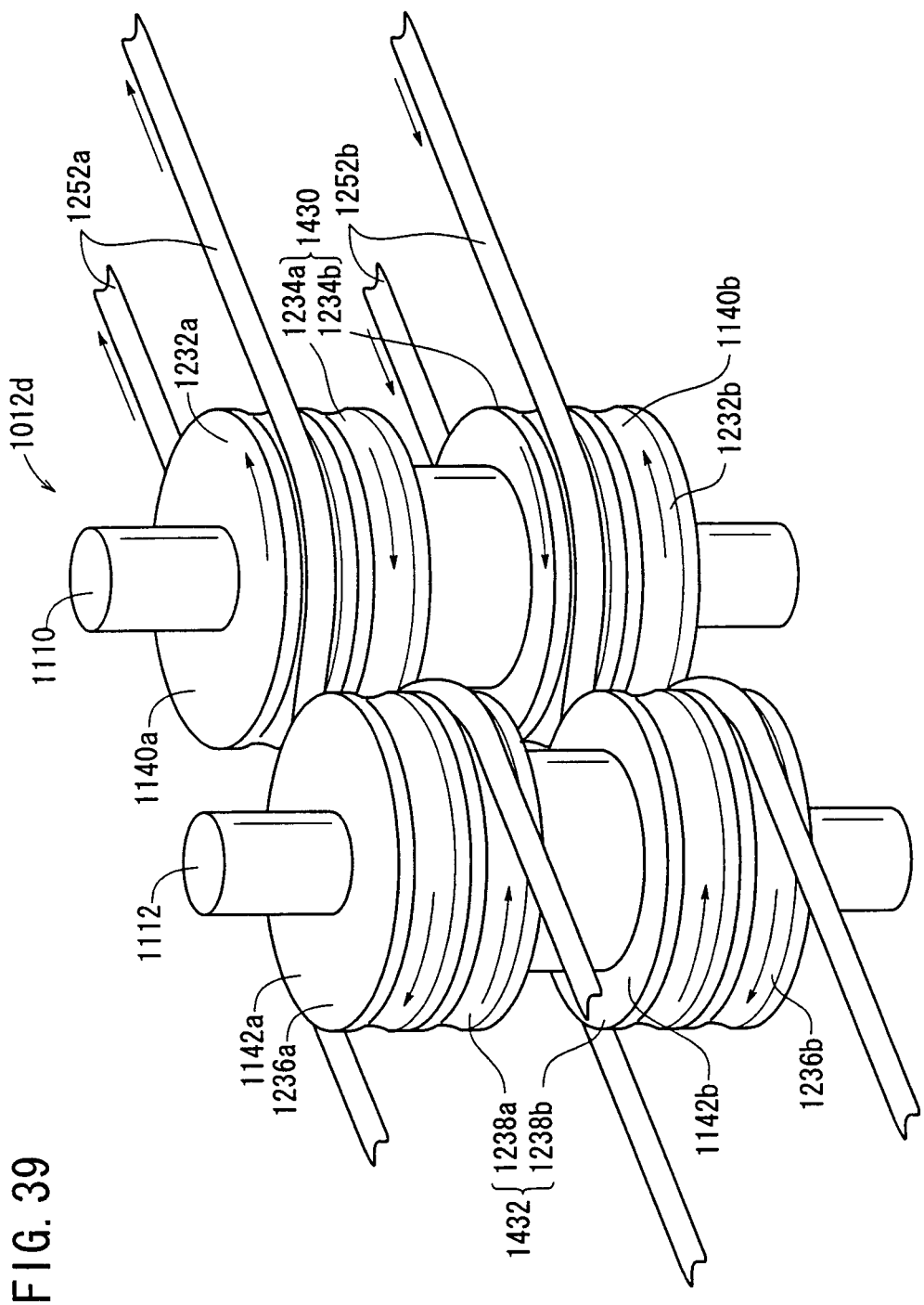
FIG. 39 is an enlarged perspective view of an idle pulley and a guide pulley of the distal end working unit according to the fourth structural example.

As shown in FIG. 39, the inner two second layer idle pulleys 1234*a*, 1234*b* may be formed integrally with each other, jointly making up a central common idle pulley 1430. The inner two second layer guide pulleys 1238*a*, 1238*b* may be formed integrally with each other, jointly making up a central common guide pulley 1432.

Specifically, since the drive links 1326*a* and 1326*b* move the same distance in opposite directions, the wires move as indicated by the arrows in FIG. 39, thereby rotating the second layer idle pulley 1234*a* and the second layer idle pulley 1234*b* through the same angle and in the same direction (clockwise in FIG. 39), while also rotating the second layer guide pulley 1238*a* and the second layer guide pulley 1238*b* through the same angle and in the same direction (counterclockwise in FIG. 39). Therefore, such members do not need to be disposed separately, but may make up an integral central common idle pulley 1430 and an integral central common guide pulley 1432, which are of a simple structure. In FIG. 39, the second layer guide pulley 1238*a* and the second layer guide pulley 1238*b* are shown as being slightly spaced from each other, whereas the second layer idle pulley 1234*a* and the second layer idle pulley 1234*b* also are shown as being slightly spaced from each other, for facilitating understanding. However, the distance between them may essentially be nil.

Drive member advancing and retracting mechanisms 1440*a* through 1440*d*, according to first through fourth examples, for moving the first end effector driving mechanism 1320*a* and the second end effector driving mechanism 1320*b* over substantially the same distance and in opposite directions, shall be described below with reference to FIGS. 40 to 43.

Figure 40:
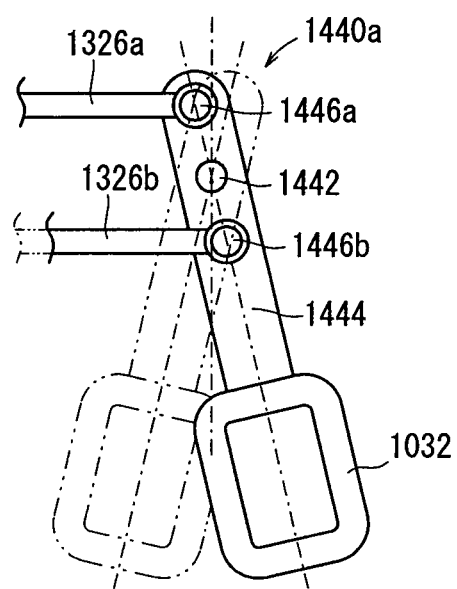
FIG. 40 is a schematic view of a drive member advancing and retracting mechanism according to a first example.

As shown in FIG. 40, the drive member advancing and retracting mechanism 1440*a* according to the first example comprises an arm 1444 rotatable about a pivot 1442, a rotational engaging member 1446*a*, which is slightly spaced from the pivot 1442 in the Y1 direction, and a rotational engaging member 1446*b*, which is slightly spaced from the pivot 1442 in the Y2 direction. The distances from the pivot 1442 to the two rotational engaging members 1446*a*, 1446*b* are substantially equal to each other. The drive link 1326*a* has a proximal end thereof that rotatably engages with the rotational engaging member 1446*a*. The drive link 1326*b* has a proximal end thereof that rotatably engages with the rotational engaging member 1446*b*.

The arm 1444 corresponds to the first link 1064 described above. The trigger lever 1032 is mounted on the lower end of the arm 1444.

Figure 41:
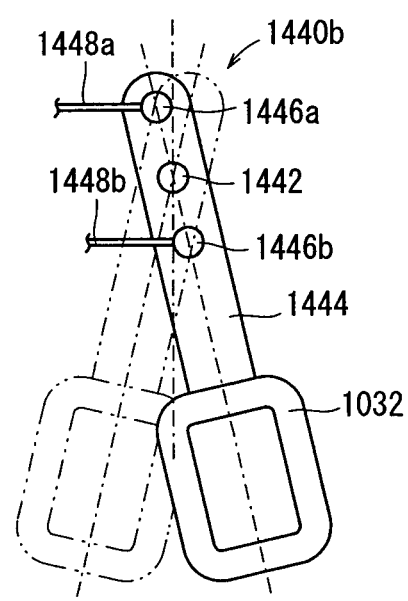
FIG. 41 is a schematic view of a drive member advancing and retracting mechanism according to a second example.

As shown in FIG. 41, as with the drive member advancing and retracting mechanism 1440*a*, the drive member advancing and retracting mechanism 1440*b* according to the second example comprises the arm 1444, the pivot 1442, and the rotational engaging members 1446*a*, 1446*b*. A wire 1448*a* is connected to the rotational engaging member 1446*a*, and a wire 1448*b* is connected to the rotational engaging member 1446*b*. The other end of the wire 1448*a* is connected to the driven wire 1252*a* (see FIG. 36) by the terminal 1250*a*, whereas the other end of the wire 1448*b* is connected to the driven wire 1252*b* (see FIG. 36) by the terminal 1250*b*.

Figure 42:
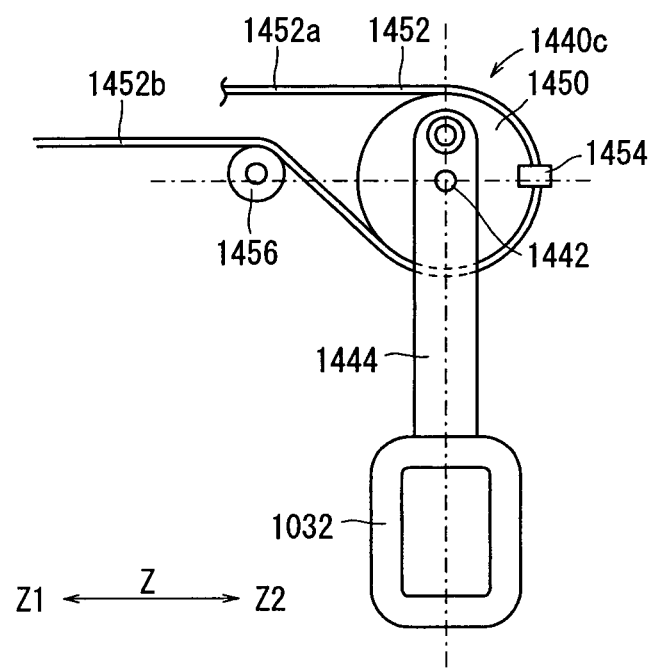
FIG. 42 is a schematic view of a drive member advancing and retracting mechanism according to a third example.

As shown in FIG. 42, the drive member advancing and retracting mechanism 1440*c* according to the third example comprises the arm 1444, a rotary operating member 1450 fixed to the arm 1444, a wire 1452 wound around the rotary operating member 1450, a securing member 1454 securing a portion of the wire 1452 to the rotary operating member 1450, and an idler 1456 that is held against a portion of the wire 1452 near to the rotary operating member 1450. The rotary operating member 1450 is in the form of a thin cylindrical body and operates as a pulley. Specifically, the wire 1452 has a portion 1452*a* thereof that is held in contact with an upper portion of the rotary operating member 1450, and another portion 1452*b* thereof held in contact with a portion of the rotary operating member 1450, which faces in the Y2 direction.

The rotary operating member 1450 rotates in unison with the arm 1444 about the pivot 1442. The portion 1452*a* of the wire 1452 from the securing member 1454 is connected to the driven wire 1252*a* (see FIG. 36) by the terminal 1250*a*. The other portion 1452*b* of the wire 1452 is connected to the driven wire 1252*b* (see FIG. 36) by the terminal 1250*b*.

The rotary operating member 1450 has an appropriate large diameter, so as to be capable of fully pulling the driven wire 1252*a* and the driven wire 1252*b*. The securing member 1454 is disposed in a position such that it does not prevent the wire 1452 from being drawn in and fed out.

The idler 1456 is held against the wire 1452, thereby defining the layout and path of the wire 1452 through the hollow region 1048*a* in the connector shaft 1048 to hold the portions 1452*a*, 1452*b* of the wire 1452 closely to each other. The idler 1456 may double as a tensioner for the wire 1452.

Figure 43:
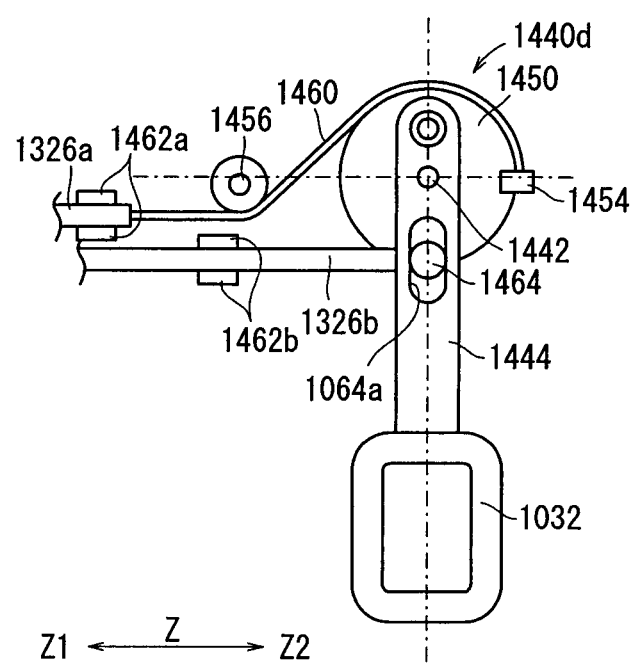
FIG. 43 is a schematic view of a drive member advancing and retracting mechanism according to a fourth example.
Figure 44:
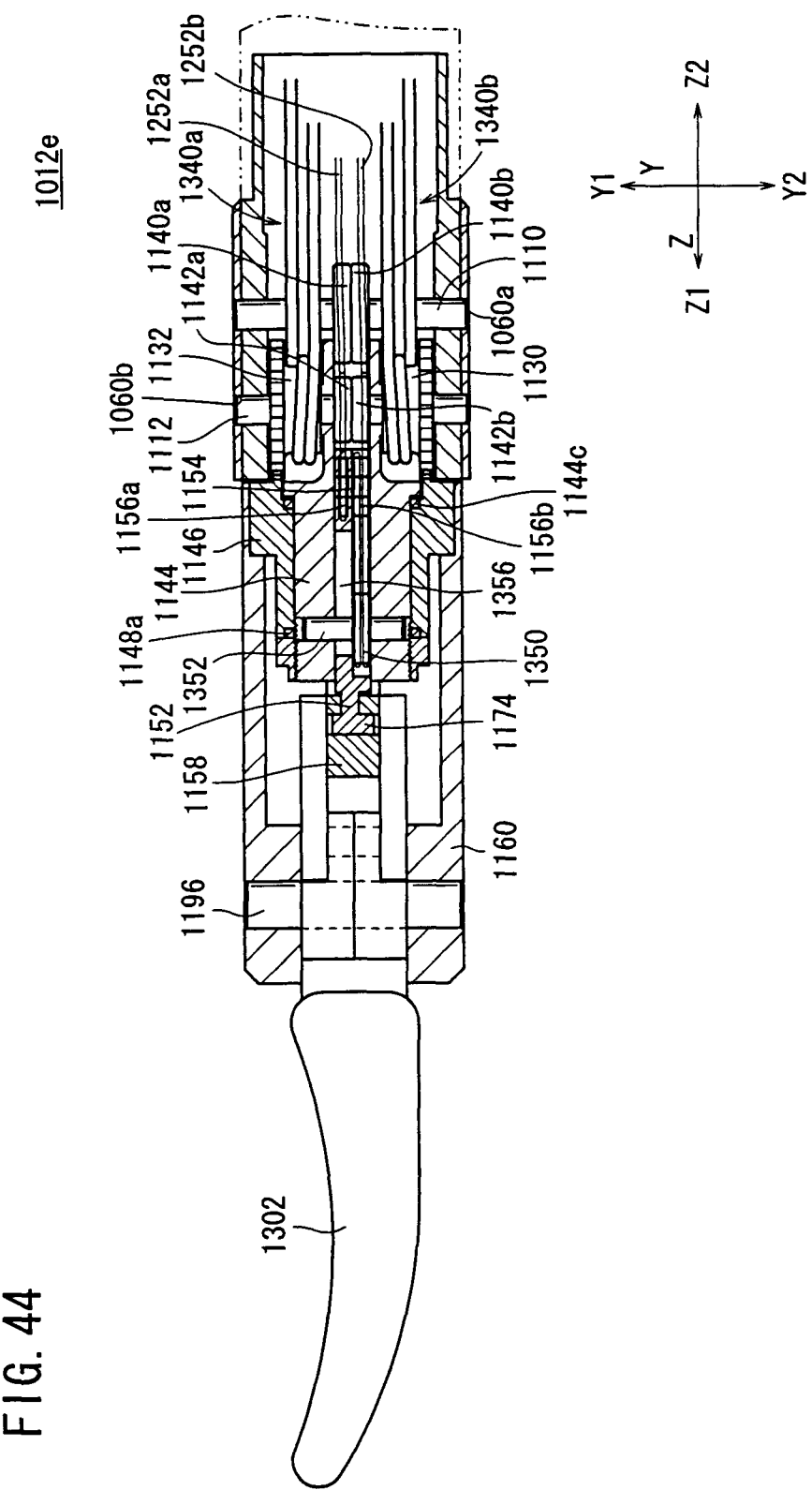
FIG. 44 is a sectional side elevational view of a distal end working unit according to a fifth structural example.
Figure 45:
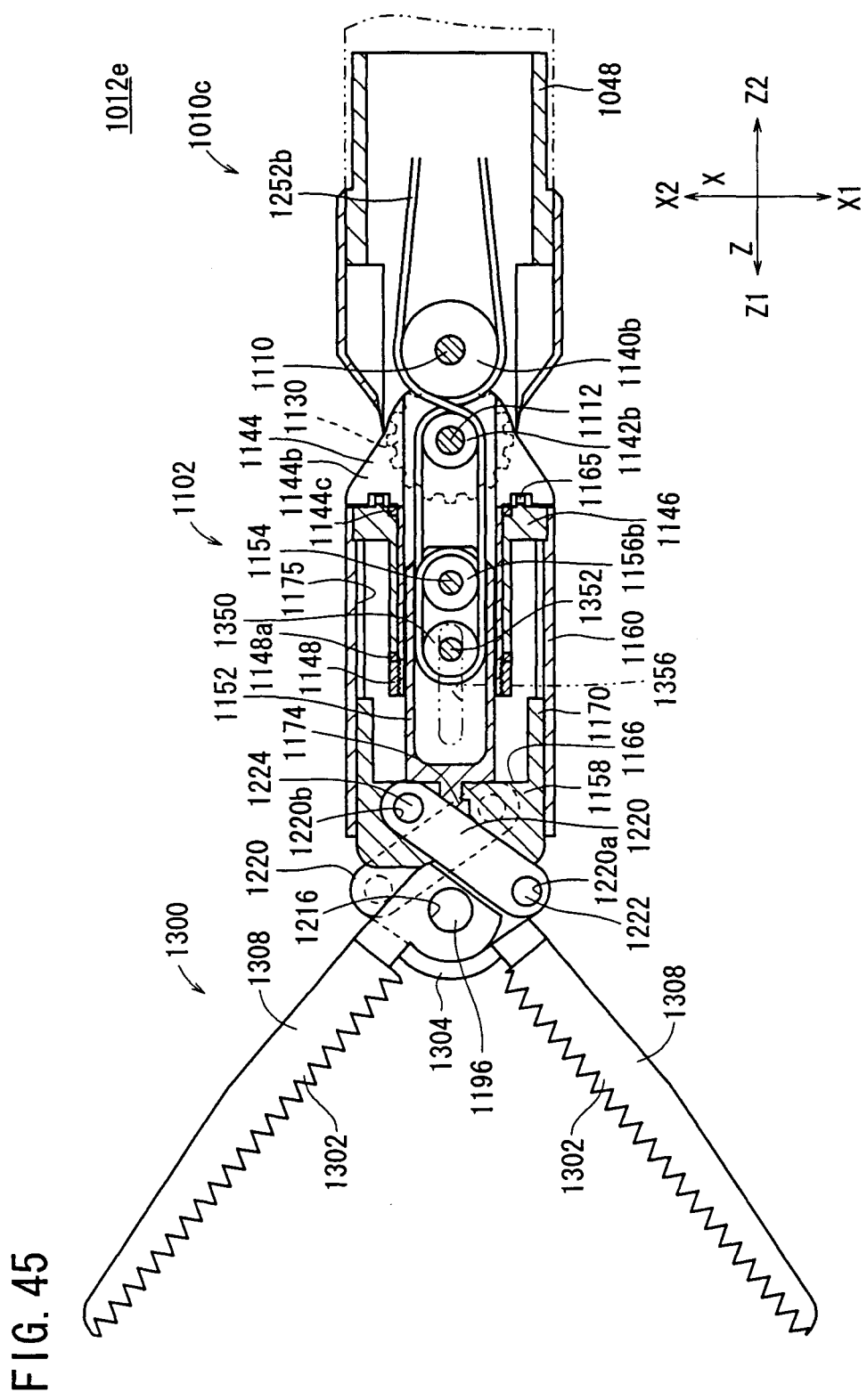
FIG. 45 is a sectional plan view of the distal end working unit according to the fifth structural example.
Figure 46:
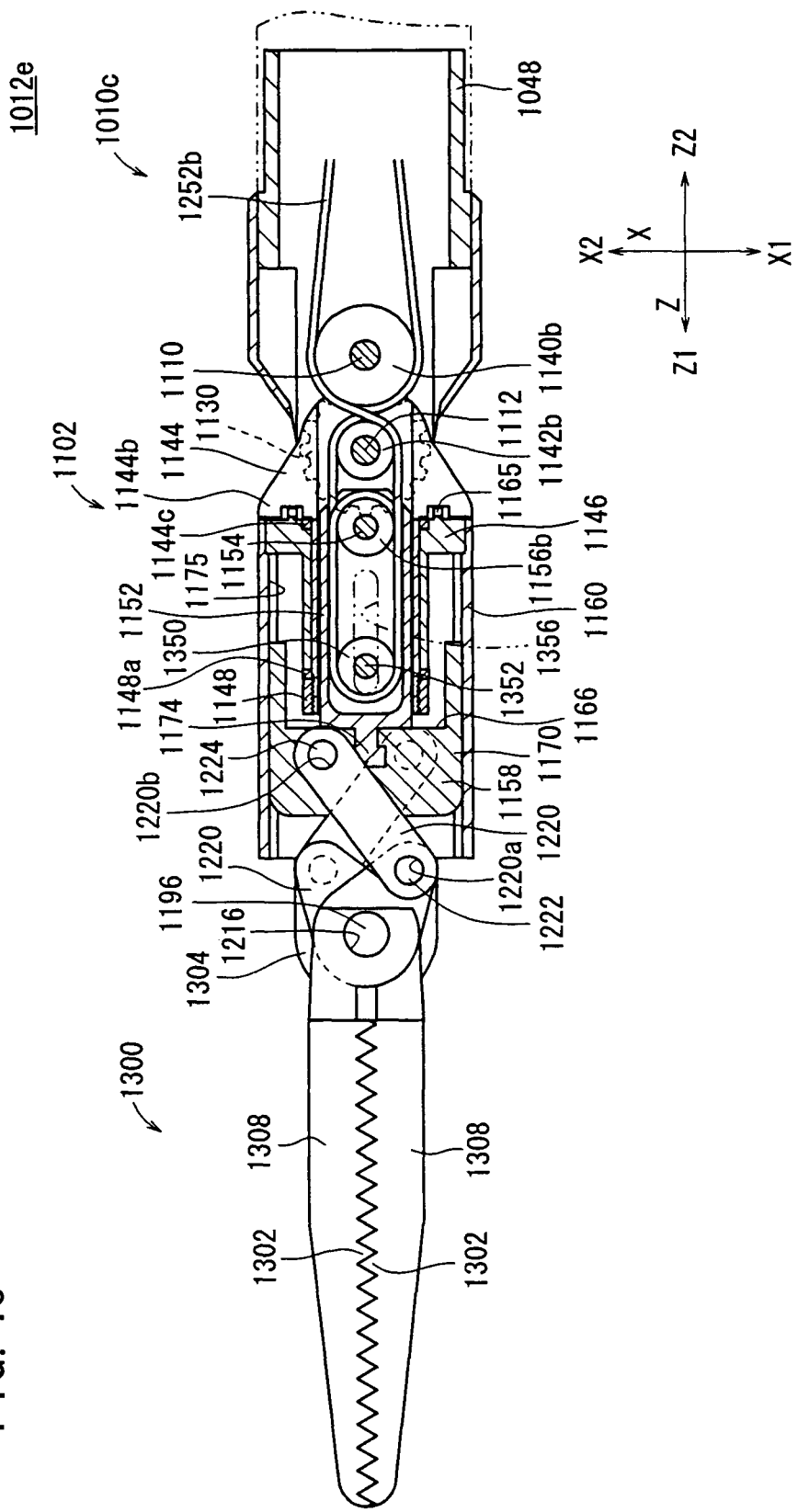
FIG. 46 is a sectional side elevational view of the distal end working unit according to the fifth structural example, with a gripper being closed.
Figure 47:
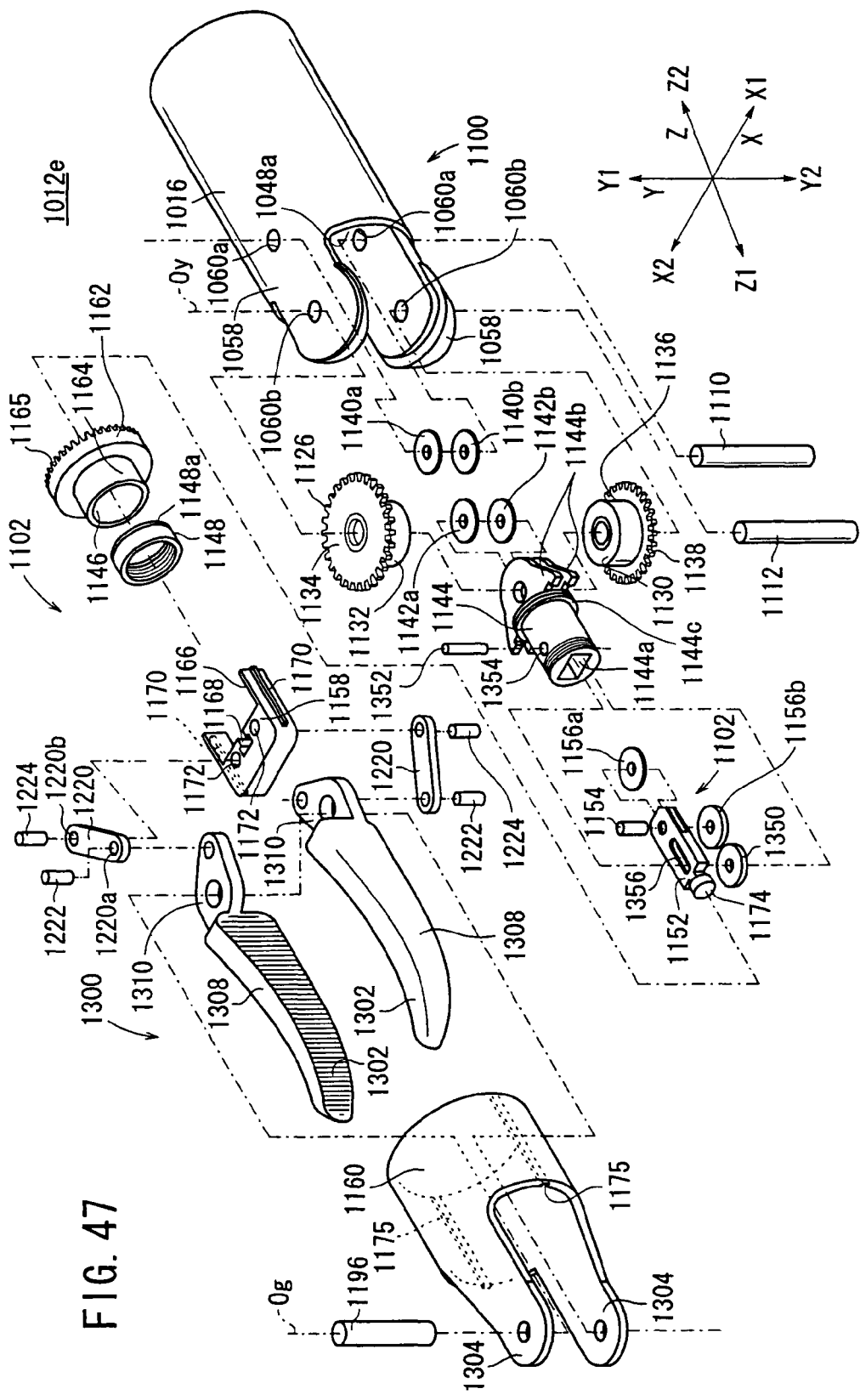
FIG. 47 is an exploded perspective view of the distal end working unit according to the fifth structural example.

As shown in FIG. 43, the drive member advancing and retracting mechanism 1440*d* according to the fourth example comprises the arm 1444, the rotary operating member 1450, a wire 1460, the securing member 1454, and the idler 1456. The wire 1460 has a distal end thereof connected to the proximal end of the drive link 1326*a*, and a proximal end portion wound around the upper portion of the rotary operating member 1450. The proximal end is fixed to the rotary operating member 1450 by the securing member 1454. The idler 1456 is disposed in engagement with the wire 1460, for defining the layout and path of the wire 1460 and the drive link 1326*a*.

The proximal end of the drive link 1326*b* is rotatably supported on a lower engaging member 1464 of the rotary operating member 1450. The arm 1444 has an oblong hole 1064*a* formed therein for guiding the lower engaging member 1464. The drive link 1326*a* and the drive link 1326*b* are supported for back and forth movement in the Z direction by means of guides 1462*a*, 1462*b*.

The drive member advancing and retracting mechanisms 1440a through 1440d make it possible to move the first end effector driving mechanism 1320a and the second end effector driving mechanism 1320b over substantially the same distance in opposite directions. The drive member advancing and retracting mechanisms 1440a through 1440d may also be applied to the distal end working unit 1012e, as shall be described below.

The distal end working unit 1012e according to the fifth structural example will be described below. The distal end working unit 1012e includes a first end effector driving mechanism 1340a and a second end effector driving mechanism 1340b.

As shown in FIGS. 44, 45, 46 and 47, the first end effector driving mechanism 1340a is essentially the same as the above-described first end effector driving mechanism 1320a (see FIG. 36). The second end effector driving mechanism 1340b differs from the second end effector driving mechanism 1320b (see FIG. 36) described above, in that a return pulley (a cylindrical member, a transmitting member) 1350 is added thereto, and the driven coupling wire 1328 and the driven coupling pulley 1330 are dispensed with. The driven pulley 1156a and the driven pulley 1156b are disposed coaxially.

The main shaft 1144 has a diametrical hole 1354 formed therein, with a pin 1352 inserted and fixed therein. The hole 1354 extends through the sleeve of the main shaft 1144 across the hole 1144a.

The rod (transmitting member) 1152 has an oblong hole 1356 formed therein, which extends axially and has a width large enough to allow the pin 1352 to be inserted therethrough. The rod 1152 is disposed at a position that is slightly offset from the axis of the working unit 1016 in the Y1 direction. The knob 1174 on the distal end is disposed on the axis (see FIG. 22). However, the rod 1152 may also be positioned centrally.

As with the driven pulley 1156 (see FIG. 20), the driven pulley 1156a is rotatably supported by the pin 1154 on the end of the rod 1152, in the Z2 direction. The pin 1154 extends through the rod 1152 and projects in the Y2 direction, with the driven pulley 1156b being supported on the projecting end thereof. The driven pulley 1156b has a width large enough to support two turns of the driven wire 1252b. The hole 1144a has a height large enough so that the driven pulleys 1156a, 1156b and the rod 1152 may be inserted therein. The driven pulleys 1156a, 1156b are coaxially supported by the pin 1154 in the hole 1144a for independent rotation.

Within the hole 1144a, the pin 1352 is inserted into the oblong hole 1356 and the central hole in the return pulley 1350 from the Y1 direction and toward the Y2 direction, thus allowing the rod 1152 and the driven pulleys 1156a, 1156b to move axially back and forth. The return pulley 1350 is supported rotatably by the pin 1352, is fixed in position, and has a width large enough to support two turns of the driven wire 1252b. If the return pulley 1350 is of a two-layer structure, then the return pulley 1350 can be rotated in opposite directions when the end effector is opened and closed, thereby reducing friction between the wire and the pulley.

Figure 48:
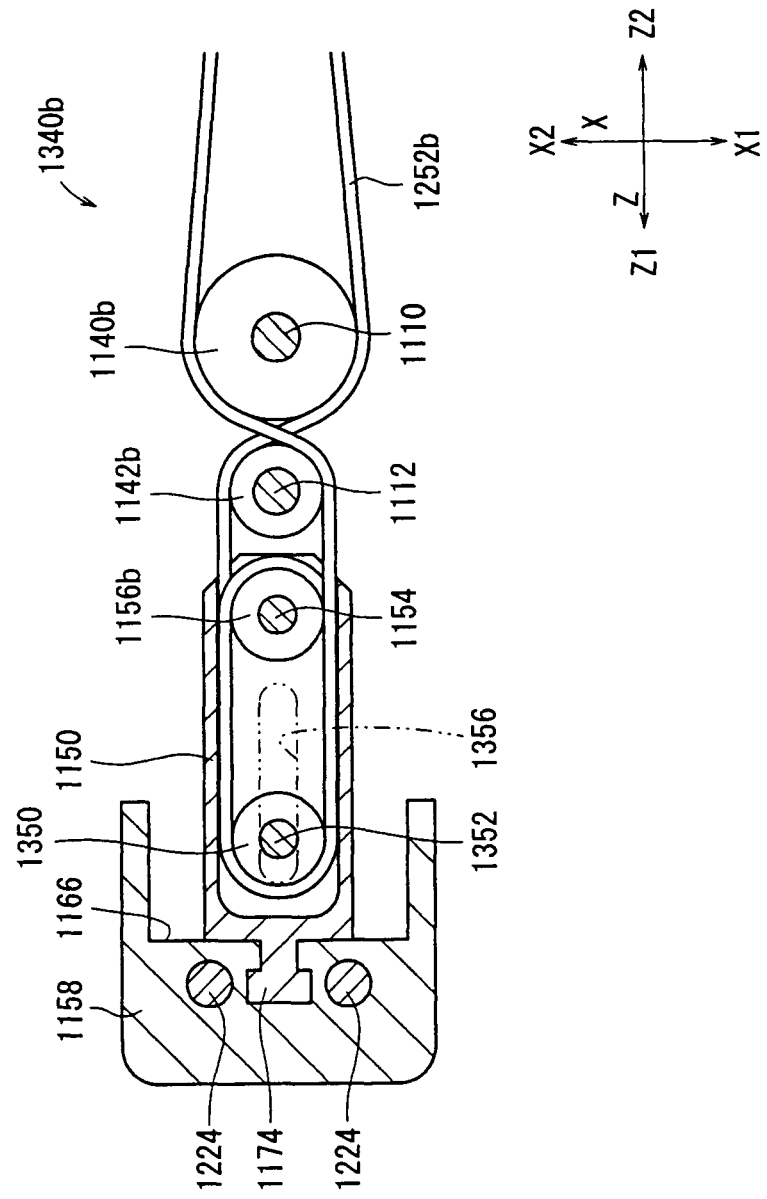
FIG. 48 is a plan view, partly in cross section, of a second end effector drive mechanism with a trigger lever being pushed out.
Figure 49:
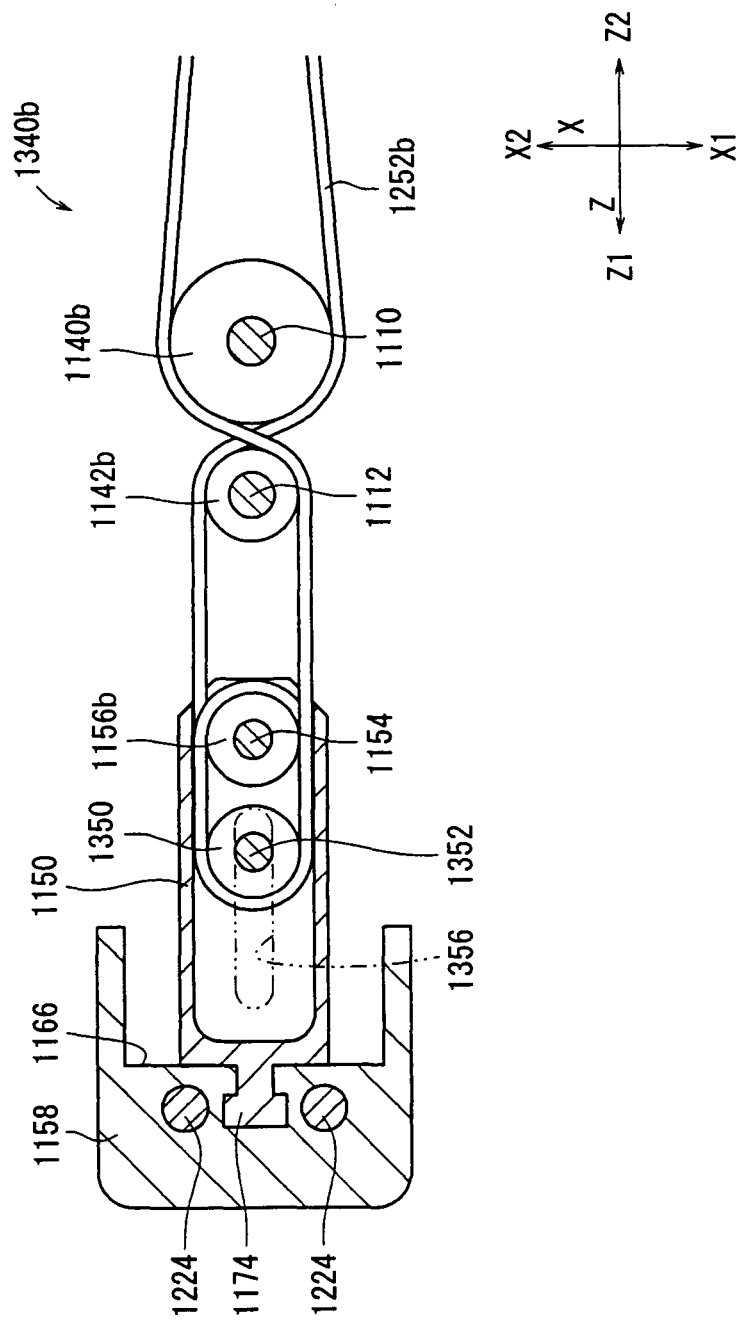
FIG. 49 is a plan view, partly in cross section, of the second end effector drive mechanism with the trigger lever being fully pulled.
Figure 50:
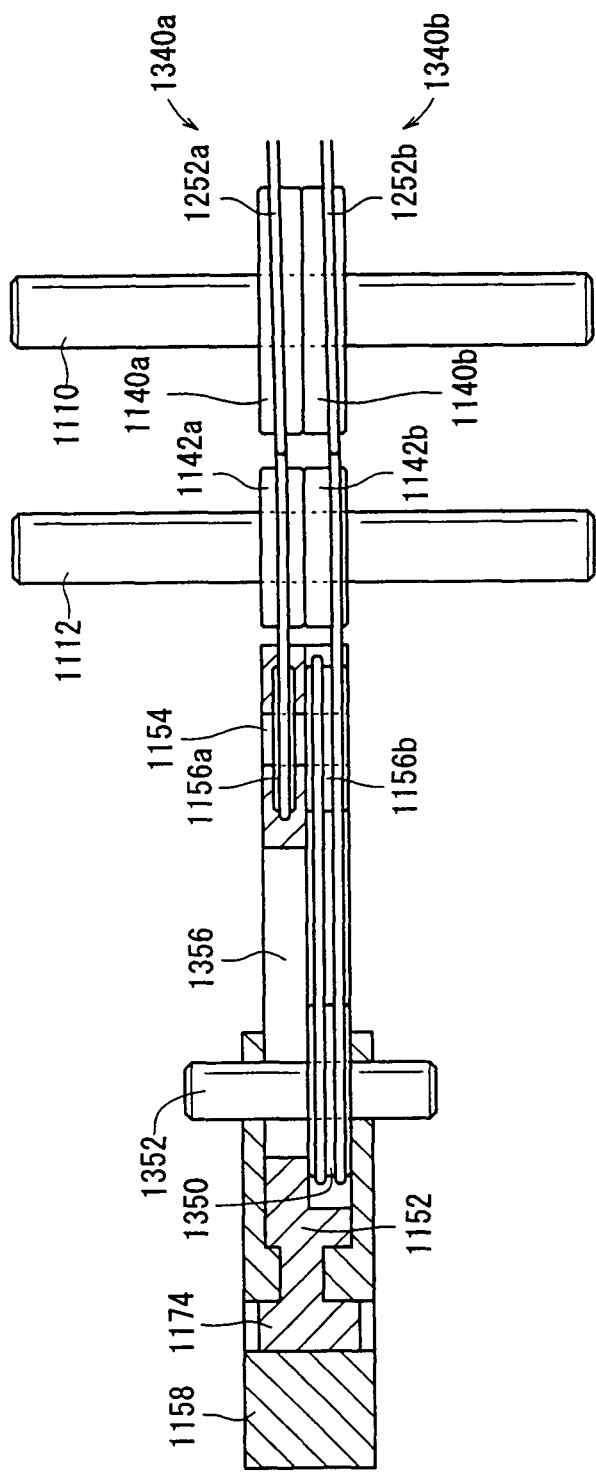
FIG. 50 is a side elevational view, partly in cross section, of the second end effector drive mechanism with the trigger lever being pushed out.

As shown in FIGS. 48, 49, and 50, in the second end effector driving mechanism 1340b, the return pulley 1350 is disposed more closely to the distal end than the driven pulley 1156b, and the driven wire 1252b is wound around the driven pulley 1156b and the return pulley 1350. In other words, the driven wire 1252b passes from the terminal 1250b of the drive link 1326b of the driving member, through the side of the idle pulley 1140b that faces in the X1 direction, and then extends in the X2 direction, passing through the side of the guide pulley 1142b that faces in the X2 direction, and extends to the surface of the driven pulley 1156b, which faces in the X2 direction. The driven wire 1252b extends in the Z1 direction to the surface of the return pulley 1350 that faces the X2 direction, is wound in a half turn around the surface of the return pulley 1350 that faces the X1 direction, and then returns in the Z2 direction.

The driven wire 1252b is wound in a half turn around the surface of the driven pulley 1156b, which faces the Z2 direction. The driven wire 1252b passes through the side thereof, which faces in the X2 direction, and extends again toward the return pulley 1350. The driven wire 1252b is wound in a half turn around the surface of the return pulley 1350, which faces the Z1 direction, and returns toward the X2 direction. Thereafter, the driven wire 1252b extends from the side of the guide pulley 1142b, which faces in the X1 direction, to the side of the idle pulley 1140b, which faces in the X2 direction, and is connected to the terminal 1250b of the drive link 1326b. The terminal 1250 and the driven wire 1252b are mechanically connected to the trigger lever 1032 by the drive link 1326b.

The idle pulley 1140b is greater in diameter than the guide pulley 1142b in FIGS. 48, 49, and 50, for preventing the gears 1134, 1138 (see FIG. 20) disposed adjacent to the guide pulley 1142b from interfering with the shaft 1110, and for holding the idle pulley 1140b and the guide pulley 1142b close to each other.

Figure 51:
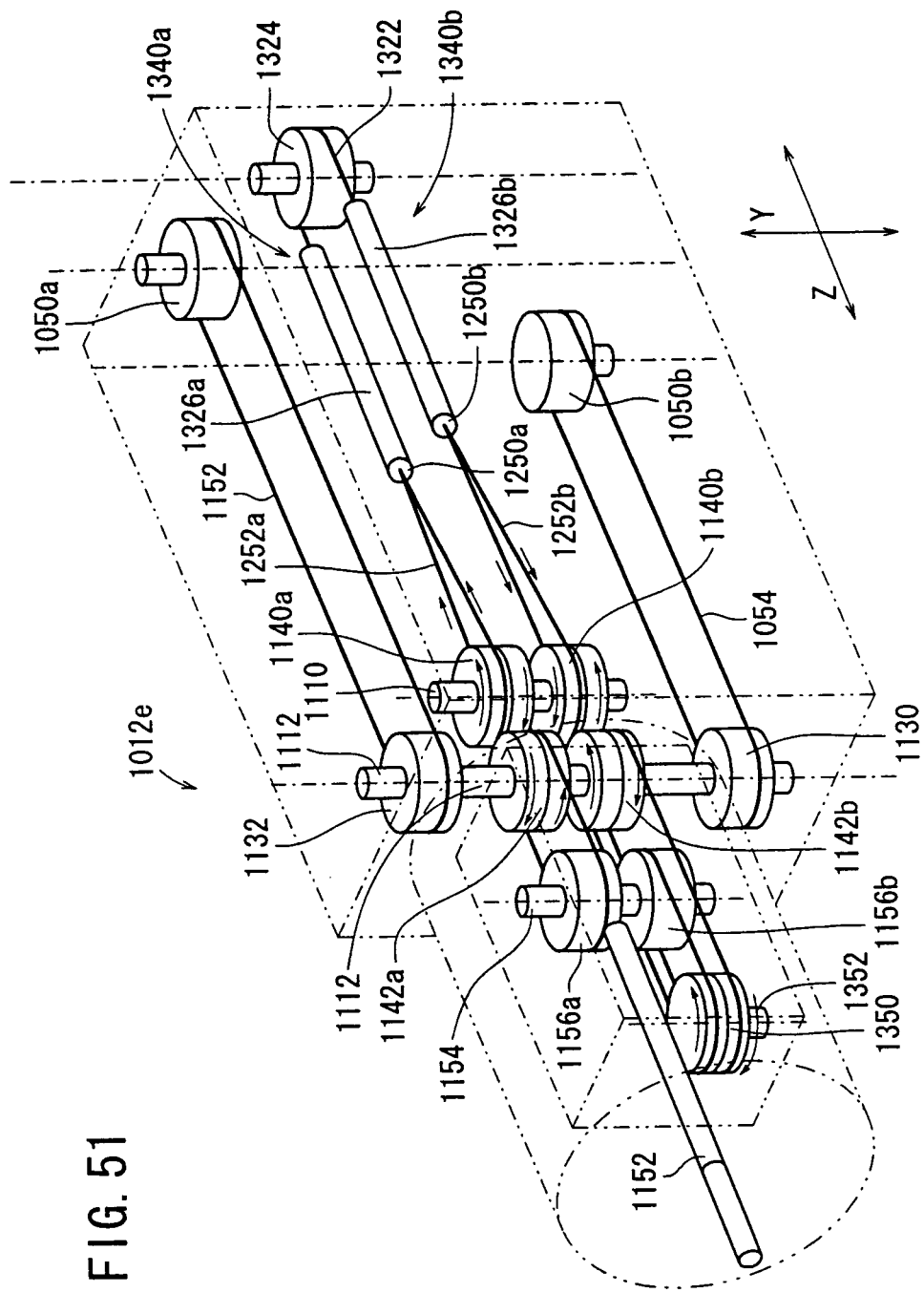
FIG. 51 is a schematic structural view of the distal end working unit according to the fifth structural example.

FIG. 51 schematically shows the distal end working unit 1012e, for facilitating understanding of the structure thereof.

Figure 52:
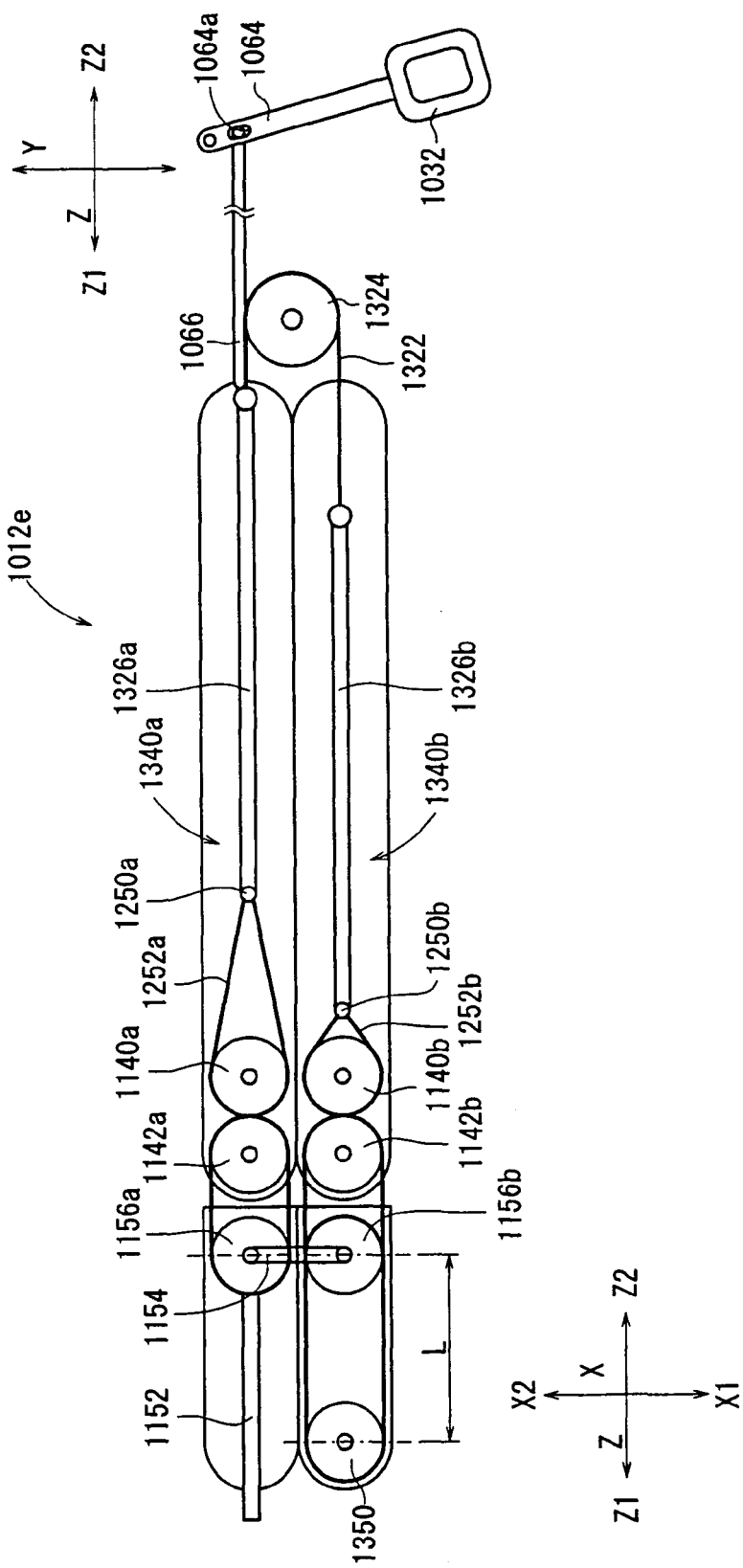
FIG. 52 is a schematic side elevational view of the distal end working unit according to the fifth structural example, with the trigger lever being fully pulled.

As shown in FIG. 52, when the trigger lever 1032 is fully pulled by the hand, the rod 1152 moves in the Z2 direction to close the end effector 1300. At this time, the operations and advantages of the distal end working unit 1012e are the same as those of the distal end working units shown in FIGS. 23 and 36, and such features will not be described in detail below.

Since the driven pulley 1156b is arranged coaxially with the driven pulley 1156a, the driven pulley 1156b is displaced in unison with the driven pulley 1156a in the Z2 direction. Since the drive link 1326b is displaced and pushed out, the driven wire 1252b and the drive coupling wire 1322 do not sag. The distance between the driven pulley 1156b and the return pulley 1350 is represented by L.

Figure 53:
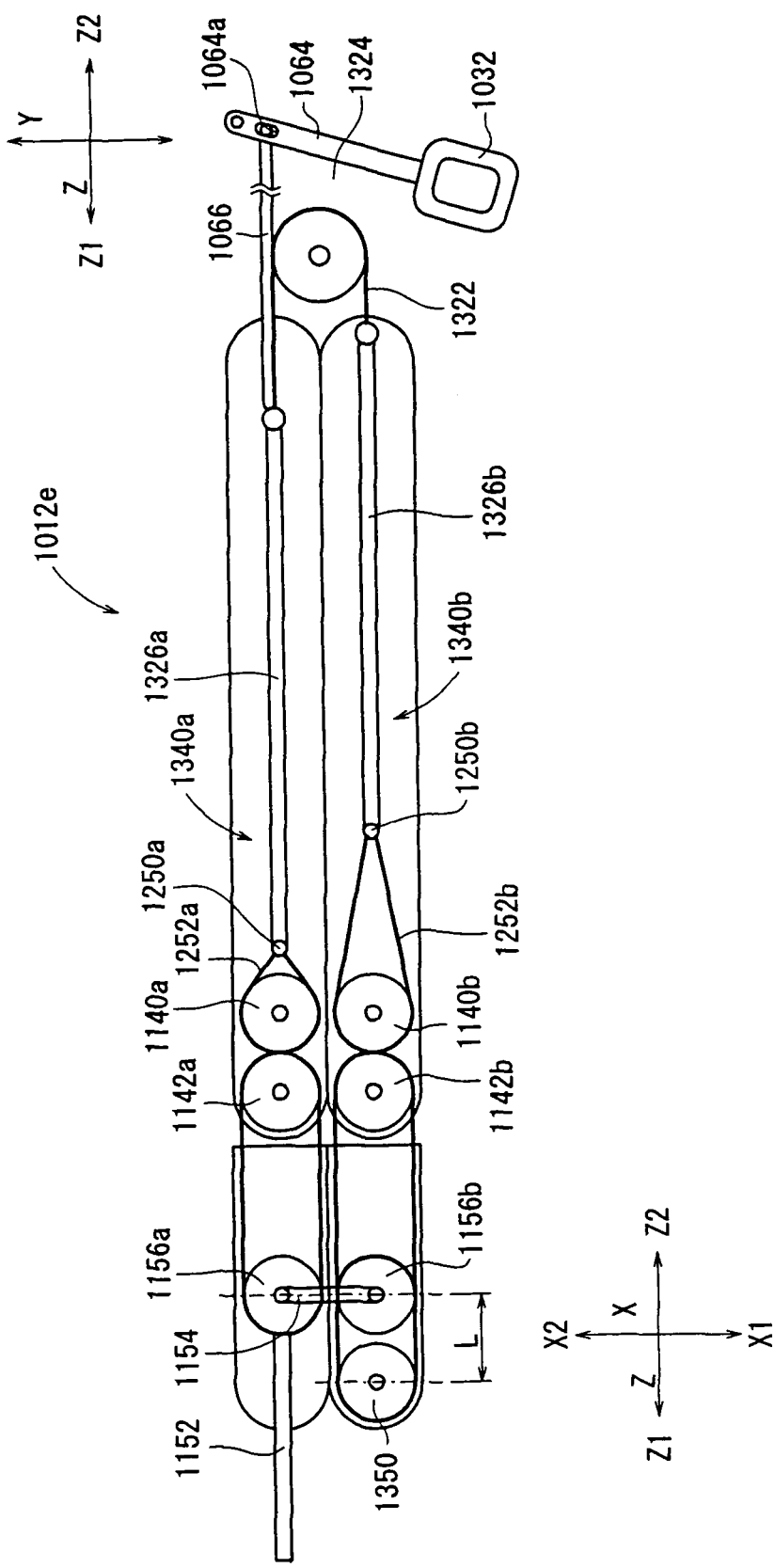
FIG. 53 is a schematic side elevational view of the distal end working unit according to the fifth structural example, with the trigger lever being pushed out.

As shown in FIG. 53, when the trigger lever 1032 is fully pushed out by hand, the drive coupling wire 1322 moves counterclockwise in FIG. 53, and the drive link 1326b acts to pull the driven wire 1252b. Since the distal end portion of the driven wire 1252a is wound around the return pulley 1350, which is fixed in position, the driven wire 1252a does not move in its entirety, and the driven pulley 1156b moves in the Z1 direction depending on the distance that the drive link 1326b moves, thereby reducing the distance L. Since the distance L is reduced, the driven wire 1252a is fed out accordingly toward the drive link 1326b, which is allowed to move. The driven pulley 1156b thus acts as a movable pulley, whereas the return pulley 1350 acts as a fixed pulley.

Since the driven pulley 1156a is coaxial with the driven pulley 1156b, the driven pulley 1156a is displaced in unison with the driven pulley 1156b in the Z1 direction, thereby pushing the rod 1152 in the Z1 direction to open the end effector 1300.

Since the forces for pushing out the trigger lever 1032 by hand are transmitted directly and mechanically to the end effector 1300 by the second end effector driving mechanism 1320b, the end effector 1300 can be opened with a desired strong force, rather than by given forces such as from an elastic body. Therefore, the distal end working unit can appropriately be used to perform techniques for peeling off living tissue or for opening a hole using an outer side surface of the end effector 1300.

When the object W is brought into contact with the outer side surface of the end effector 1300, the driven wire 1252*b*, the drive link 1326*b*, and the trigger lever 1032 are no longer moved further in the Z1 direction, thus allowing the operator to feel, with the fingertip, that the outer side surface of the end effector 1300 has contacted the object W. The operator also can feel the hardness of the object W.

The distal end working units 1012*d*, 1012*e* can operate about the yaw axis and the roll axis in the same manner as the distal end working unit 1012*a*. Although not shown, when the distal end working unit 1012*e* operates about the yaw axis, the composite mechanism 1102 and the end effector 1300, which are positioned more closely to the distal end than the shafts (see FIG. 51) of the guide pulley 1142*a* and the guide pulley 1042*b*, swing in the yawing direction about the shafts of the guide pulley 1142*a* and the guide pulley 1042*b*. Since the distal end working unit 1012*e* is a non-interference mechanism, as with the distal end working unit 1012*a*, when the distal end working unit 1012*e* operates about the yaw axis, the degree at which the end effector 1300 is opened remains unchanged. Conversely, when the degree of opening of the end effector 1300 is changed, the yaw axis is not operated. The end effector 1300 and the roll axis are related to each other in the same manner.

Since the driven pulleys 1156*a*, 1156*b* slide over the same distance and in the same direction, they can be disposed coaxially with each other, such that the distal end working unit 1012*e* enables increased housing and space efficiency. Further, the distal end working unit 1012*e* is made up of a reduced number of parts, and can easily be assembled and serviced for maintenance. Since the driven pulleys 1156*a*, 1156*b* slide in unison with each other, only one sliding movement assembly is sufficient. With the distal end working unit 1012*d*, however, since the driven pulleys 1156*a*, 1156*b* slide in opposite directions, two sliding movement assemblies are required.

All the pulleys of the distal end working unit 1012*e*, i.e., the idle pulleys 1140*a*, 1140*b*, the guide pulleys 1142*a*, 1142*b*, the driven pulleys 1156*a*, 1156*b*, and the return pulley 1350, have their rotational shafts positioned parallel to each other (in the Y directions), and the pulleys are laid out efficiently without dead spaces. The driven coupling pulley 1330 of the distal end working unit 1012*d*, however, has an axis that extends perpendicularly to the other pulleys.

The distal end working unit 1012*e* does not require the driven coupling wire 1328 or the wire fastening means thereof, which are provided in the distal end working unit 1012*d*. The distal end working unit 1012*e* is simpler in structure, since it does not require the driven coupling pulley 1330 in the distal end working unit 1012*d*.

The wire drive ratio of the distal end working unit 1012*e* at the time the end effector 1300 is operated to grip and open is 1:1, as with the distal end working unit 1012*d*, and is well balanced.

Figure 54:
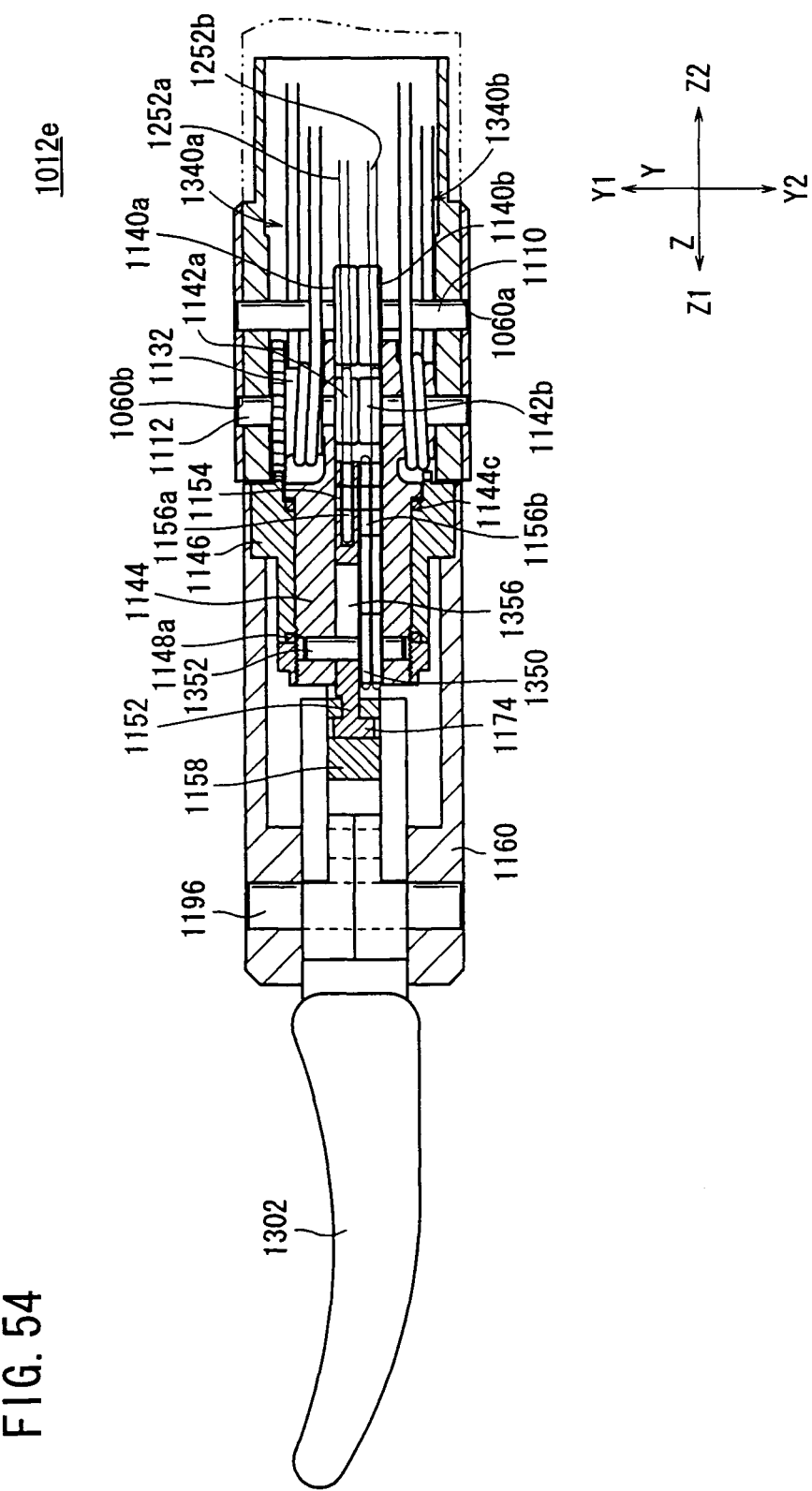
FIG. 54 is a sectional side elevational view of a distal end working unit according to a first modification of the fifth structural example.

In the distal end working unit 1012*e*, the face gear 1165 together with the gears 1134, 1138 make up a differential gear. According to a first modification, as shown in FIG. 54, the face gear 1165 is held in mesh with the gear 1134 only, and portions thereof corresponding to the main shaft 1144 and the gear body 1130 (see FIG. 20) may be of an integral structure. The distal end working unit thus operates about the roll axis based on the action of the wire 1052 via the gear 1134, and operates about the yaw axis by swinging the main shaft 1144, based on a coordinated operation of the wires 1052, 1054.

Figure 55:
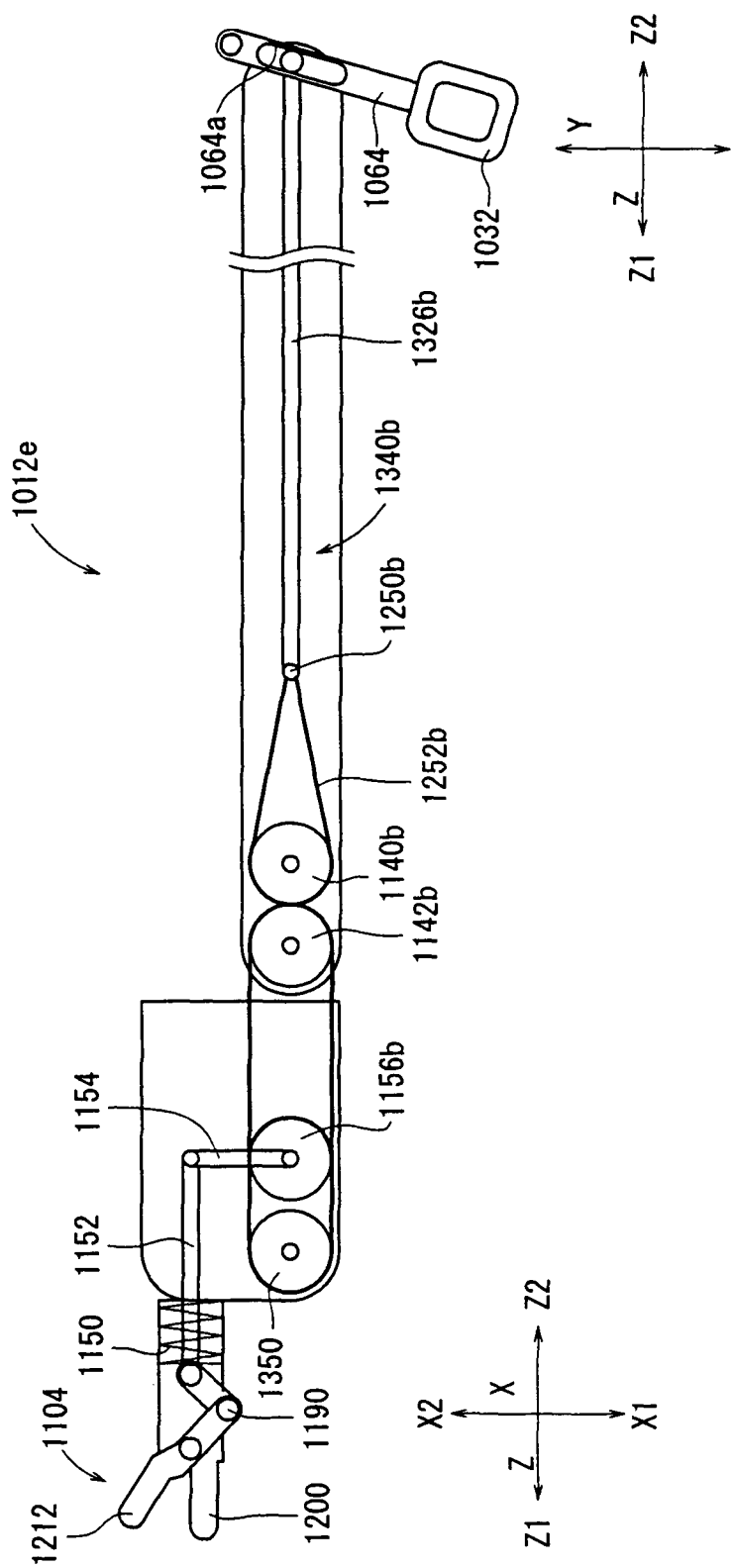
FIG. 55 is a sectional side elevational view of a distal end working unit according to a second modification of the fifth structural example.

As shown in FIG. 55, according to a second modification of the distal end working unit 1012*e*, the second end effector driving mechanism 1340*b* having the return pulley 1350 is employed, and the first end effector driving mechanism 1340*a* is dispensed with. According to this modification, the spring 1150 may be provided to make up for the action of the first end effector driving mechanism 1340*a*, which is dispensed with. While the spring 1150 is a compression spring in the distal end working unit 1012*a* (see FIG. 22) according to the first structural example, according to the second modification, the spring 1150 comprises a tension spring for resiliently biasing the end effector to close itself. The trigger lever 1032 is connected to the drive link 1326*a*. According to the modification shown in FIG. 55, the idle pulley 1140*b* may be dispensed with. As with the distal end working unit 1012*b* (see FIG. 32), according to the second structural example, the driven wire 1252 may be wound in one turn or more around the guide pulley 1142*b* from at least one direction. If two distal end working units 1012*e* according to the second embodiment shown in FIG. 55 are combined in parallel with each other, then manual forces work actively when the trigger lever 1032 is pulled and returned, and forces are produced in both directions. Hence, the spring 1150 for producing forces may be dispensed with. The distal end working unit may be used as a gripping forceps as well as a peeling forceps.

Although the distal end working unit 1012*e* comprises a double-sided-open-type of end effector 1300, the distal end working unit 1012*e* may also incorporate a single-sided-open-type of end effector 1104 (see FIG. 19), or another type of end effector.

The distal end working units 1012*a* through 1012*e* are not limited to the above structures, but may consist of various other structures as well.

Figure 56A:
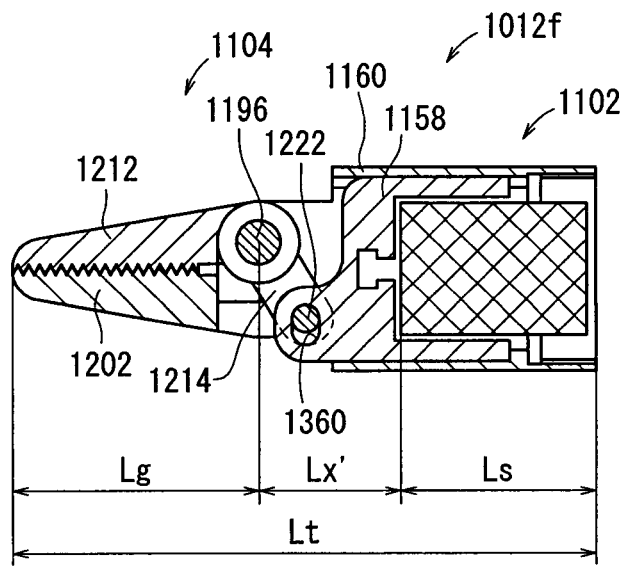
FIG. 56A is a schematic sectional side elevational view of a distal end working unit, with a gripper link portion thereof being omitted from illustration.
Figure 56B:
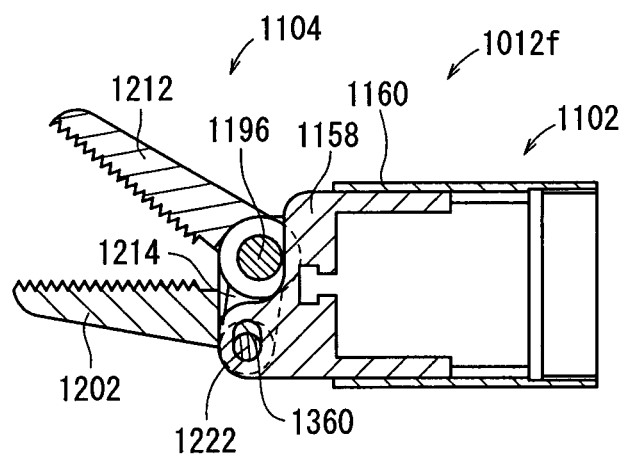
FIG. 56B is a schematic sectional side elevational view of the distal end working unit, with the gripper link portion thereof being omitted from illustration, and with a gripper being opened.

For example, as shown in FIG. 56A, a distal end working unit 1012*f* according to a modification does not include the gripper links 1220 (see FIG. 19), but rather, the driven plate 1158 and the lever 1214 are connected to each other by the pin 1222 and an oblong hole 1360. The pin 1222 is fixed to the lever 1214. According to this modification, with the distal end working unit 1012*f*, when the pin 1222 slides inside the oblong hole 1360, the second gripper 1212 is turned so as to open and close the end effector (see FIG. 56B). The distal end working unit 1012*f* can be made up of a reduced number of parts, since the gripper link 1220 and the pin 1224 (see FIG. 19) are dispensed with.

The distal end working unit 1012*f* includes a wire-and-pulley non-interference mechanism (i.e., composite mechanism 1102), which is basically of the same structure as the distal end working unit 1012*f*, and has the same length Ls. The length Lg from the pin 1196 forming the gripper axis to the distal end can be of the same dimension as the distal end working unit 1012*a* shown in FIG. 19. The connector length Lx' from the front surface of the driven plate 1158 to the pin 1196 can be considerably smaller than the connector length Lx (see FIG. 19) of the distal end working unit 1012*a*, thus resulting in a reduction in the overall length Lt of the distal end working unit 1012*f*.

Accordingly, the distal end working unit 1012*f* can easily be operated by bending the yaw-axis joint in the body cavity 1022, even if the body cavity 1022 is small, and makes it possible to perform operations in deeper and smaller spaces. The distal end working unit 1012*f* may be applied to a structure in which two grippers, such as gripping forceps, are opened and closed. Furthermore, linear motion of the rod 1152 may be converted into rotary motion by gears for gripping objects. The end effector is not limited to being a gripper type, but may comprise rotary electrodes or the like having scissors, or an opening and closing unit.

The wire-and-pulley non-interference mechanism according to the present embodiment has a wider operable range (e.g., of +90°) and a more compact structure than the conventional type (e.g., a soft mirror type) including a curved portion corresponding to the connector shaft 1048 and other non-interference mechanisms. Therefore, the distance from the curved or bent portion, corresponding to a joint, to the distal end may be reduced, thereby allowing the end effector to approach the living body freely and without limitations, and to operate in small spaces.

As described above, the end effector driving mechanisms 1260, 1320a, 1320b, 1340a and 1340b of the medical manipulator 1010 according to the present embodiment have structures that are kept out of interference with the other operating axes, thereby making it possible to easily construct the distal end working unit with high degrees of freedom, and to realize strong gripping forces (or peeling forces). The transmitting members (drive members, the wire 1056, etc.), which are mechanically connected to the manually operated input unit, allow the operator to feel the external forces that are applied to the distal end working unit 1012 reliably and easily. Moreover, the end effector driving mechanisms 1260, 1320a, 1320b, 1340a, 1340b are made up of a simple structure that is free of gears.

Specifically, with the medical manipulator 1010 according to the present embodiment, the transmitting members involved in opening and closing the gripper include the driven wire 1252, which comprises a flexible member, together with the guide pulley 1142 and the driven pulley 1156, which form cylindrical members around which the driven wire 1252 is wound. The cylindrical members around which the flexible member is wound are made up of a simple and lightweight structure, and can change the attitude of the attitude changing mechanism so as not to interfere with the state of the end effector.

Stated otherwise, with the medical manipulator 1010 according to the present embodiment, the guide pulley 1142, forming a cylindrical member, is provided as a rotational shaft in the attitude changing mechanism, and the transmitting members include the driven wire 1252, making up a flexible member that is partially wound around the guide pulley 1142, and the end effector that is operable through the driven wire 1252. Since a flexible member is used, which is wound around the cylindrical member, the medical manipulator is simple and lightweight in structure, and the end effector can be actuated through the flexible member. The attitude of the attitude changing mechanism can be changed so as not to interfere with the state of the end effector, using the cylindrical member as a rotational shaft.

Figure 57:
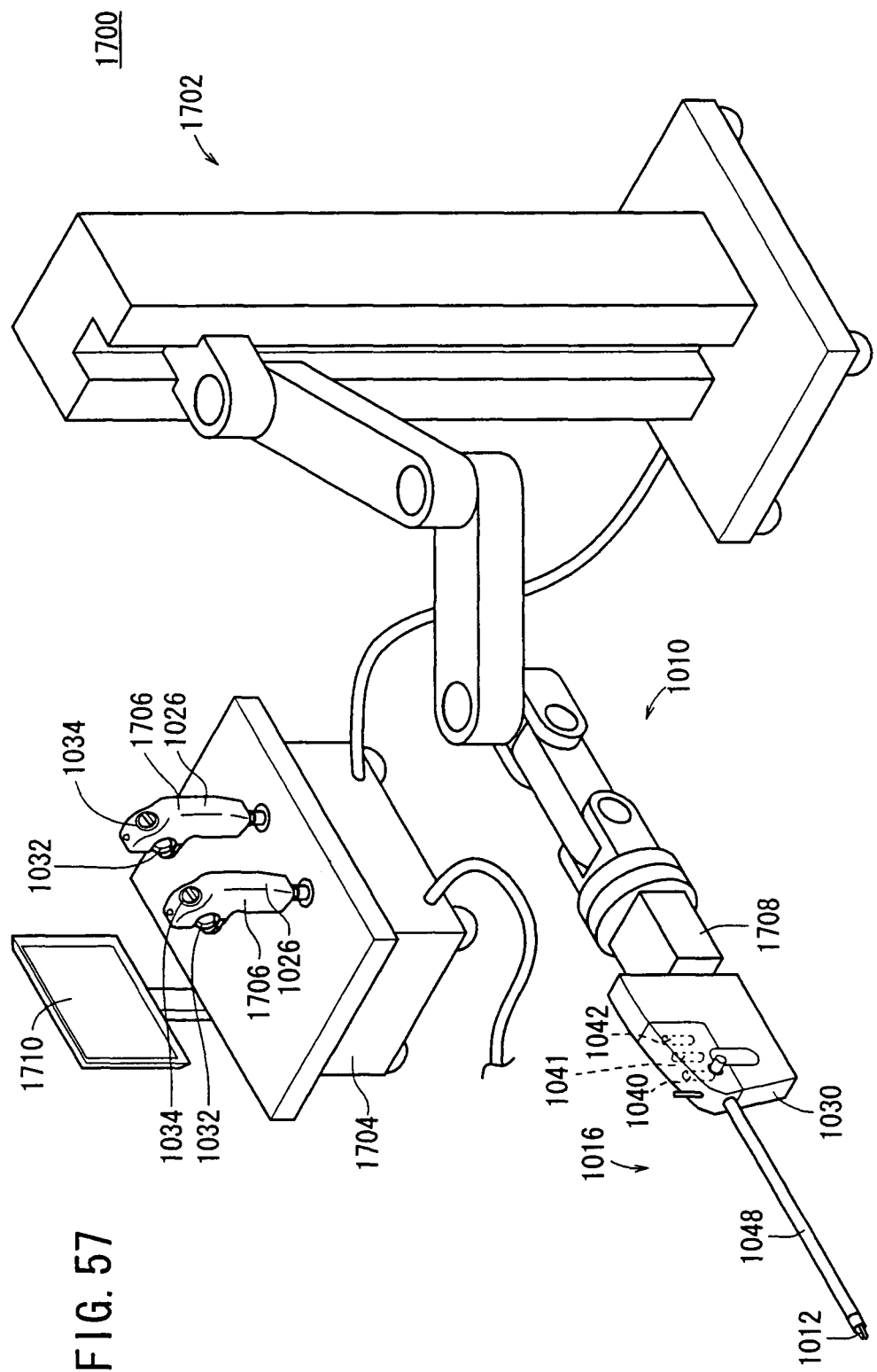
FIG. 57 is a schematic perspective view of a surgical robot system with a working unit connected to the distal end of a robot arm.

The above embodiment may be applied to the surgical robot system 1700 shown in FIG. 57, for example.

The surgical robot system 1700 includes an articulated robot arm 1702, and a console 1704 with the working unit 1016 connected to the distal end of the robot arm 1702. The distal end of the robot arm 1702 incorporates therein a mechanism, which operates the same as the medical manipulator 1010. The robot arm 1702 may be any means for moving the working unit 1016, and is not limited to an installed type, but may also be of an autonomous movable type. The console 1704 may be of a table type, a control panel type, or the like.

The robot arm 1702 preferably has six or more independent joints (rotary shafts, slide shafts, etc.) for setting the position and orientation of the working unit 1016 as desired. The medical manipulator 1010 is integrally combined with the distal end 1708 of the robot arm 1702. The medical manipulator 1010 includes a motor 1042 (an actuator ganged with the manually operable input unit) instead of the trigger lever 1032 (see FIG. 22). The motor 1042 actuates the wire 1056 (see FIG. 22) or the drive coupling pulley 1324 (see FIG. 36).

The robot arm 1702 operates under control of the console 1704, and may be automatically actuatable according to a program, or actuated by joysticks 1706 mounted on the console 1704, or by a combination of the program and the joysticks 1706. The console 1704 includes functions of the controller 1045. The working unit 1016 includes the distal end working unit 1012 (1012a through 1012f).

The console 1704 includes the two joysticks 1706 serving as an operation commander, and a monitor 1710. Although not shown, the two joysticks 1706 are capable of individually operating two robot arms 1702. The two joysticks 1706 are disposed in respective positions where they can easily be operated by both hands of the operator. The monitor 1710 displays information such as an image produced by a soft mirror.

The joysticks 1706 can be moved vertically and horizontally, twisted, and tilted. The robot arm 1702 can be moved depending on movements of the joysticks 1706. The joysticks 1706 may be master arms. A communication means between the robot arm 1702 and the console includes a wired system, a wireless system, a network system, and a combination thereof.

The joysticks 1706 have respective trigger levers 1032, which can be operated to energize the motor 1042.

The type of medical manipulator is not limited to a forceps, but may be scissors, a tying-knot device, a needle holder, or a knife such as an electrosurgical knife, an ultrasonic knife, a laser knife, or the like. The medical manipulator is not limited to one that is used in performing laparoscopic surgery.

The medical manipulator according to the present invention is not limited to the above-described embodiments, but may include any of various additional and/or modified structures without departing from the gist of the present invention.

What is claimed is:

1. A medical manipulator comprising:
    a distal end working unit that is disposed on a distal end of a shaft, the distal end working unit being openable and closable for a gripping operation and being movable in a rolling direction and in a yaw direction,
    the distal end working unit mechanically and manually openable and closable, without intervention of a motor, for a gripping operation through a transmitting member when an operating unit is operated by an operator,
    the operating unit having a trigger lever for mechanical and manual opening and closing of the distal end working unit for the gripping operation,
    the transmitting member including a flexible member and a cylindrical member around which said flexible member is wound, and
    the distal end working unit adapted to be operated in the rolling direction and in the yaw direction by a motor energized when said operating unit is operated by the operator.

2. The medical manipulator according to claim 1, wherein the distal end working unit comprises forceps.

3. The medical manipulator according to claim 1, wherein the medical manipulator is adapted to be used for performing laparoscopic surgery, brain surgery, thoracoscopic surgery, or urologic surgery.

4. The medical manipulator according to claim 1, wherein the medical manipulator is adapted to be used for performing brain surgery, thoracoscopic surgery, or urologic surgery.

5. The medical manipulator according to claim 1, wherein the operating unit is adapted to be detachably attached to a proximal end of the shaft for operating said distal end working unit.

* * * * *